United States Patent [19]

Curtiss, III et al.

[11] Patent Number: 5,656,488
[45] Date of Patent: Aug. 12, 1997

[54] RECOMBINANT AVIRULENT SALMONELLA ANTIFERTILITY VACCINES

[75] Inventors: Roy Curtiss, III, St. Louis, Mo.; Kenneth S. K. Tung, Charlottesville, Va.

[73] Assignee: Washington University, St. Louis, Mo.

[21] Appl. No.: 222,182

[22] Filed: Apr. 1, 1994

Related U.S. Application Data

[63] Continuation of Ser. No. 791,347, Nov. 18, 1991, abandoned, which is a continuation-in-part of Ser. No. 615,720, Nov. 21, 1990, abandoned.

[51] Int. Cl.⁶ .............................. C12N 1/21; A61K 45/00
[52] U.S. Cl. .................. 435/252.33; 424/184.1; 424/200.1; 435/252.3; 435/252.8; 435/69.3; 530/395
[58] Field of Search .................. 424/184.1, 93.48, 424/185.1; 435/69.3, 252.3, 252.8, 352.33; 530/395

[56] References Cited

U.S. PATENT DOCUMENTS

| | | | |
|---|---|---|---|
| 3,992,520 | 11/1976 | Gwatkin | 424/85 |
| 4,190,495 | 2/1980 | Curtiss | 435/172 |
| 4,392,997 | 7/1983 | Goldberg | 260/112.5 R |
| 4,585,587 | 4/1986 | Goldberg | 260/112.5 R |
| 4,585,651 | 4/1986 | Beck | 424/88 |
| 4,795,634 | 1/1989 | Grimes | 424/85.9 |
| 4,888,170 | 12/1989 | Curtiss | 435/252.33 |
| 4,968,619 | 11/1990 | Curtiss | 424/93 |
| 4,996,297 | 2/1991 | Dunbar | 530/395 |

OTHER PUBLICATIONS

Curtiss, R. et al. Infect. Immun. 55(12):3035–3043. Dec. 1987, "*Salmonella typhimurium* Deletion Mutants . . . ".
Goldberg, E. et al. Fertility and Sterility 35(2):214–217. 1981. "Reduction of Fertility in Female Babboons . . . ".
W. F. Paul (ed), *Fundamental Immunology*, 3rd edition, pp. 1342–1344, Raven Press, New York (1993).

*Primary Examiner*—Thomas M. Cunningham
*Attorney, Agent, or Firm*—Howell & Haferkamp, L.C.

[57] ABSTRACT

Avirulent microbes which include a recombinant expression system encoding a gamete-specific antigen, are disclosed. The microbes can be used in compositions to immunize a vertebrate subject against the gamete-specific antigen, thereby preventing or reducing conception rates in the subject to which they are administered.

50 Claims, 20 Drawing Sheets

*FIG. 1A*

```
                                                                          BclI                                       EcoRI
     CTTATATGAATGATCAAGGAAAAATGTCTTCGTGGAGAGGGAACCTGCATCACTCAGAATTCCCAGCAGTGCATGTTAAAG
641  ---------+---------+---------+---------+---------+---------+---------+---------+ 720
        Y  M  N  D  Q  G  K  C  L  R  G  E  G  T  C  I  T  Q  N  S  Q  Q  C  M  L  K

AAGATCTTTGAAGGTGGAAAACTCCAATTCATGGTTCAAGGGTGTGAGAACATGTGCCCATCTATGAACCTCTTCTCCCA
721  ---------+---------+---------+---------+---------+---------+---------+---------+ 800
      K  I  F  E  G  G  K  L  Q  F  M  V  Q  G  C  E  N  M  C  P  S  M  N  L  F  S  H
                                                                XbaI
     TGGAACGAGGATGCAAATTATATGCTGTCGAAATCAATCTTTCTGCAATAAGATCTAGAAGCCTGGGCCCTTGCTTGTTT
801  ---------+---------+---------+---------+---------+---------+---------+---------+ 880
       G  T  R  M  Q  I  I  C  C  R  N  Q  S  F  C  N  K  I  *

TGACTCAGGCAGTAAAAAGCCTCCATCACTCTATTTGGCTCATTTTATATTAGTTCCTTCCCCAGTCAACAACTGACCA
881  ---------+---------+---------+---------+---------+---------+---------+---------+ 960

CATCTGCCTCTGCCTGAGCATTAGGATGCTCAAACATCCTATCTTCTCTTCTATTCATGCTTTTATCCATTCTTCTCT
961  ---------+---------+---------+---------+---------+---------+---------+---------+ 1040
                                           SP-10-10                    SP-10-5
     GTCCTGTCTTCCCTGCTCCAACTCTTTTCTCTCCAATATTCCTGATTTTTTTCAATAAATTTCACATGCCCGAATTC
1041 ---------+---------+---------+---------+---------+---------+---------+-------  1117
```

FIG. 1B pYA810 MCS

```
              -35                          -10
ATTCTGAAATGAGCTGTTGACAATTAATCATCCGGCTCGTATAATGTGTGGAATTGTGAGC

SD                                EcoRI              SmaI
GGATAACAATTTCACACAGGAAACAGACC ATG CCG GAA TTC GCA ATT CCC GGG
                              Met Pro Glu Phe Ala Ile Pro Gly

BamHI  SalI       PstI                HindIII
GAT CCG TCG ACC TGC AGC CAA GCT CCC AAG CTT
Asp Pro Ser Thr Cys Ser Gln Ala Pro Lys Leu
```

```
                         BamHI     MluI  ApaLI
                         ‾‾‾‾‾     ‾‾‾‾  ‾‾‾‾‾
AAC TAC GCG CCG G|T GAT CCG| |ACG C|G|T GCA C|TG TAA CTAG|CT GCAG|CCAAGCTCCC|AAGCTT|
Asn Tyr Ala Pro Val Asp Pro Thr Arg Ala Leu *            ‾‾‾‾         *     ‾‾‾‾‾‾
                                               *         PstI               HindIII
```

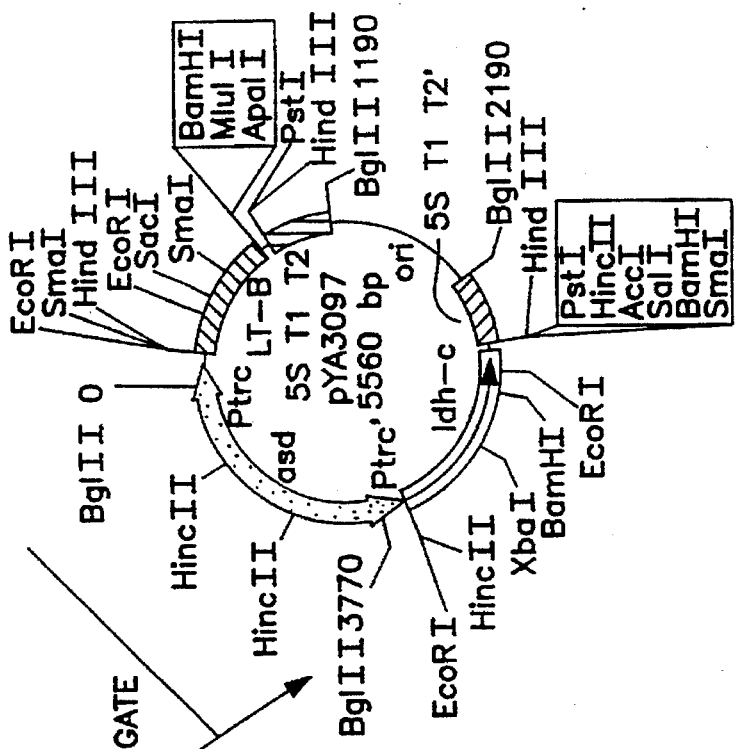
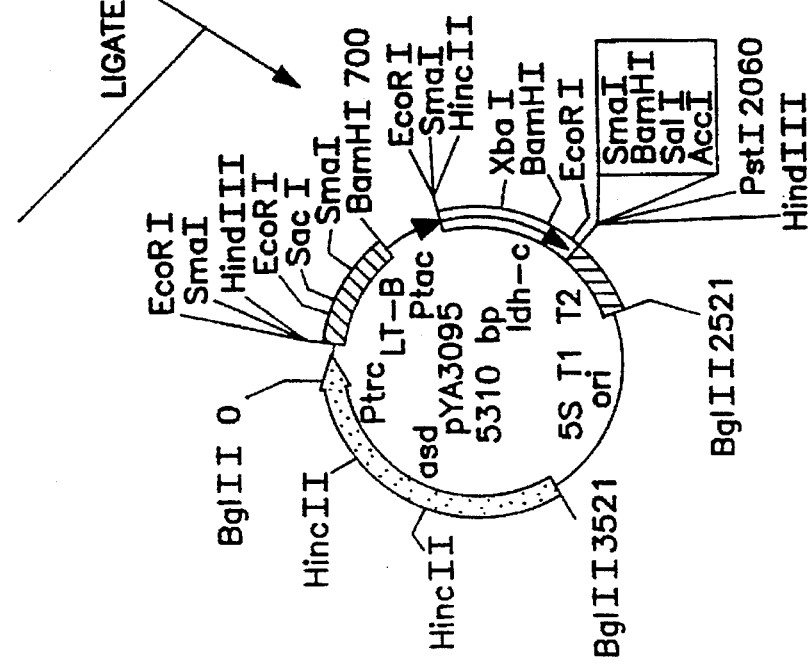
FIG. 10B

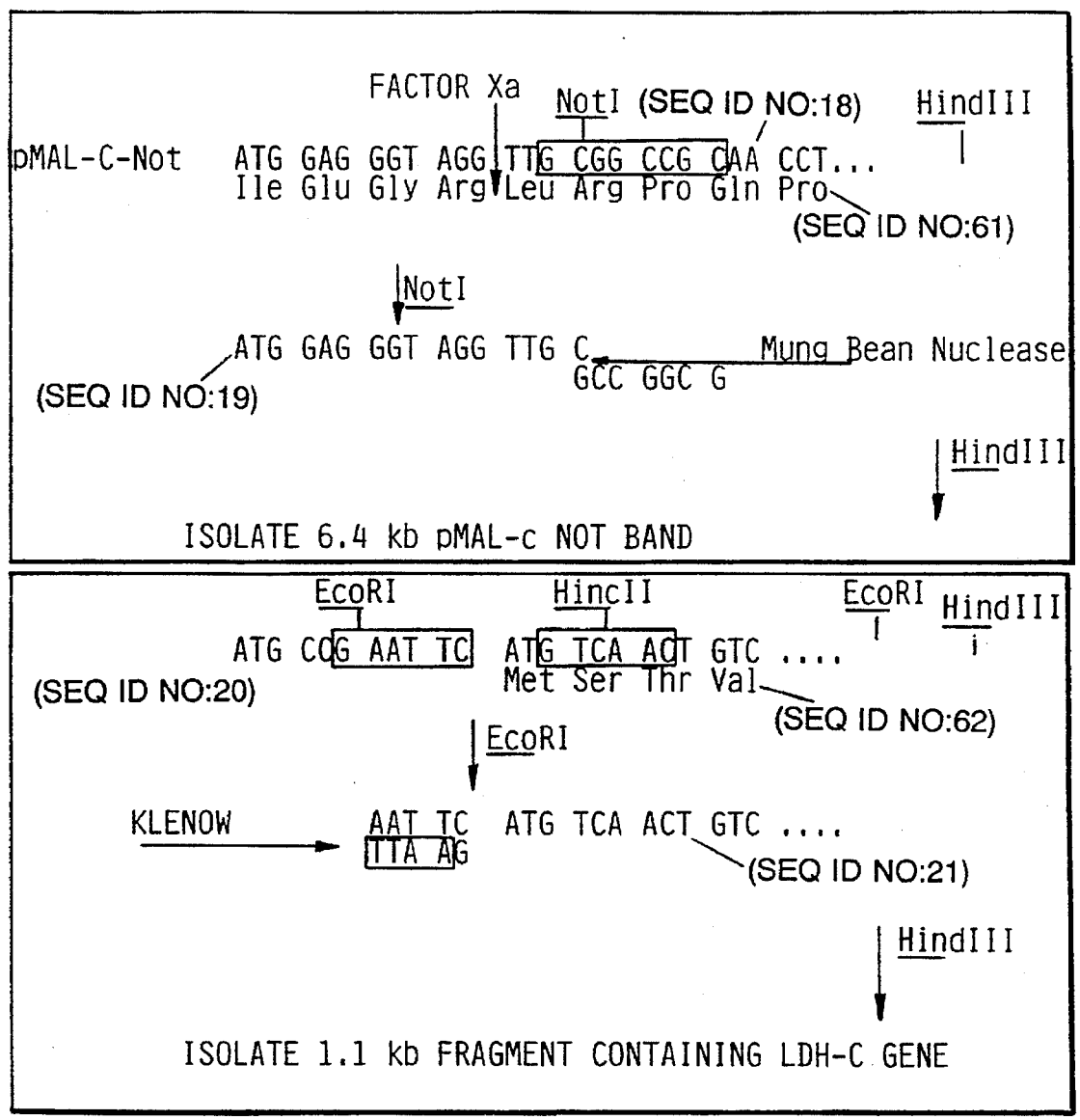
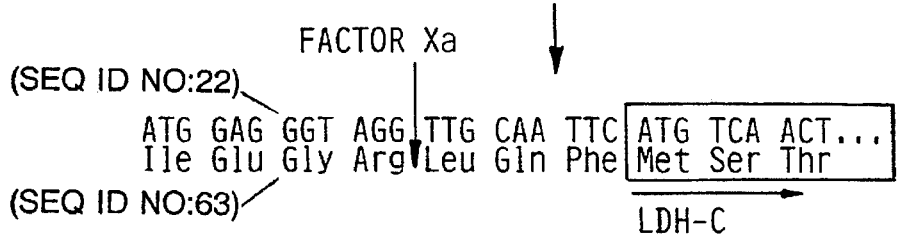
FIG. 12 pYASP-10-5+    Digest to completion with EcoRI and SmaI

```
            EcoRI                    SmaI
(SEQ ID NO:32) ...CAG ATT ACT ........TTC CCG GGG... (SEQ ID NO:33)
                   purify vector component
```

λgt11SP-10-10  → digest with EcoRI and XbaI → Recover 162 base pair fragment (SEQ ID NO:34) ....AAT TCC CAG ......AAG AT (SEQ ID NO:35)
                   Asn Ser Gln        Lys Ligate, add Klenow to fill in XbaI (SEQ ID NO:36) ...CAG AAT TCC CAG ......AAG ATC TAG      GGG... (SEQ ID NO:37)
(SEQ ID NO:68)    Gln Asn Ser Gln      Lys Ile Ter       Gly Blunt end ligate (SEQ ID NO:38) ...CAG AAT TCC CAG ......AAG ATC TAG GGG (SEQ ID NO:39)
                  Gln Asn Ser Glu      Lys Ile Ter pYASP-10ter

FIG. 15 pYASP-10ter    Digest with AlwI

AlwI (SEQ ID NO:40)...CTT GGA TCT GCG↓        AGA GAA...
                     A CGCT          ↑CT CCT
(SEQ ID NO:69)   Leu Gly Ser Ala          Arg Gly

Add Klenow to fill in; digest with PstI

PstI (SEQ ID NO:41)  AGA GGA ......TCG ACC TGC A  (SEQ ID NO:42)
                TCT CCT

Recover 769 bast pair AlwI to PstI fragment pYA2906    Digest with ApaLI

ApaLI
(SEQ ID NO:43)...ATC ACG CG       T GCA CTA
               Ile The

Fill in with Klenow, cut with PstI
                   ↓

(SEQ ID NO:44)...ATC ACG CGT GCA         GCCAAGC...
(SEQ ID NO:70)   Ile Thr Arg Ala

Ligate to 769 base pair AlwI to PstI SP-10 sequence
                              (SEQ ID NO:46)
                    ↓
(SEQ ID NO:45)...CGT GCA TCT CCT.....ACC TGC AGC CAA GC...
(SEQ ID NO:71)   Arg Ala Arg Glu pYALT-B-SP-10

*FIG. 16* pYA3098 MCS

ATTCTGAAATGAGCTGTTGACAATTAATCATCCGGCTCGTATAATGTGTGGAATTGTGAGC
                   -35                      -10

SD          NcoI      EcoRI
GGATAACAATTTCACACAGGAAACAGACC ATG G GG AAT TCG CAA
                            Met Gly Asn Ser Gln

SmaI  BamHI    SalI        PstI              HindIII
TT C CCG GGG ATC C GT CGA CCT GCA G CC AAG CTC CCA AGC TT  (SEQ ID NO:51)
  Phe Pro Gly Ile Arg Arg Pro Ala Ala Lys Leu Pro Ser (SEQ ID NO:75)

RECOMBINANT AVIRULENT SALMONELLA ANTIFERTILITY VACCINES

CROSS-REFERENCE TO RELATED APPLICATION

This is a continuation of application Ser. No. 07/791,347, filed on Nov. 18, 1991 (now abandoned) which is a continuation-in-part of U.S. patent application Ser. No. 07/615,720, filed on Nov. 21, 1990 (now abandoned), from which priority is claimed pursuant to 35 USC §120 and which is incorporated herein by reference in its entirety.

REFERENCE TO GOVERNMENT GRANT

This invention was made with Government support under Grant Nos. RO1 DE06669, awarded by the National Institutes of Health, and CSA-90-071, given by the Contraceptive Research and Development Program (CONRAD). The Government has certain rights in this invention.

TECHNICAL FIELD

The present invention relates generally to antifertility vaccine compositions and methods of using the same. More particularly, the instant invention pertains to the use of avirulent microbes for the delivery of gamete-specific antigens.

BACKGROUND OF THE INVENTION

It has long been known that men and women with significant antibody titers against human sperm are often infertile or have reduced fertility without other ill effects (Ingerslev and Ingerslev, 1989; Chen and Jones, 1981; Menge et al., 1982; Bronson et al., 1984). It has also been demonstrated that immunization of male and female animals with extracts of whole sperm can induce infertility (Kummerfeld and Foote, 1976; Munoz and Metz, 1978; Tung et al., 1979; Menge et al., 1979). Primakoff et al. (1988a) used a monoclonal antibody to purify a sperm-specific guinea pig surface antigen, PHG-20, and were able to demonstrate that injection of this purified antigen into either male or female guinea pigs induced a long-lasting immunity against fertilization (1988b). In previous studies it was shown that this monoclonal antibody reacted with a sperm adhesin to block its interaction with the zona pellucida of the egg, an essential step for fertilization (Primakoff et al., 1985).

A number of other monoclonal antibodies, prepared to ejaculated human sperm, or prepared to sperm of other species, have been found to cross react with human sperm. Some react with components of seminal plasma and others recognize antigens of testicular origin. Monoclonal antibodies which can immobilize or agglutinate human sperm or inhibit sperm binding and penetration of zona-free hamster ova have been reported. At present, several human sperm antigens are known such as the $M_r$ 95,000 antigen of Moore (Moore et al., 1987); the 55 kDa antigen recognized by the S36-37 mAbs (HSA-63) of Lee (Liu et al., 1990); and human homologs of 95 kDa and 56 kDa sperm receptors for ZP-3 (defined in mice by Saling and Bliel and Wassarman (Bliel, 1990; Leyton and Saling, 1989)). Also of interest is the FA-1 antigen of mouse and humans, partially characterized by Naz (Naz, 1988) and the 24 kD antigen from rat and human testis characterized by Shaha (Shaha et al., 1990). The antigens of Moore and Lee, as well as the SP-10 immunogen, (described below) were designated "primary vaccine candidates" (Anderson et al., 1987) by the World Health Organization Taskforce on Vaccines for Fertility Regulation.

The sperm-specific antigen, lactic dehydrogenase-C (LDH-C), has been purified, characterized, and used to immunize and inhibit fertility in rabbits (Goldberg, 1973), mice (Lerum and Goldberg, 1974) and baboons (Goldberg et al., 1981). The sperm-specific LDH-C has a substrate specificity different than for muscle and heart LDH and is capable of using branched chain ketoacids as substrates such as a-ketoisovalerate (Blanco et al., 1976) as well as using lactate as substrate. The LDH-C is present in the cytosol and mitochondria of sperm (Montamat et al., 1988) but is also present on the surface of spermatozoa (Erickson et al., 1975) thus providing a basis for the effectiveness of immunization against LDH-C in blocking fertility. More recently, Goldberg and colleagues have cloned the cDNA for the human testes-specific lactate dehydrogenase and characterized its antigenic sites (Millan et al., 1987; Hogrefe et al., 1987; Goldberg, 1987; Hogrefe et al., 1989).

LDH-X, an isozyme of LDH found only in male germ cells, is one of the best characterized human sperm antigens. It has been crystallized and amino acid sequence data is available (Goldberg, 1972). Both auto and iso-immunogenic responses to LDH-X have been noted in mice and rabbits (Goldberg, 1972), although it does not appear to be a potent autoantigen in humans (Goldberg, 1973). Infertility has been seen in baboons inoculated both systemically or locally (intrauterine) with LDH-X (Samuel et al., 1978).

Wright et al. (1989) have identified λgt11 clones that express the human sperm-specific intra-acrosomal protein antigen SP-10. This antigen is present in the sperm of higher primates and pigs (Herr et al., 1989b). As identified by reactivity with a monoclonal antibody MES-10 (Homyk et al., 1989), the SP-10 antigen has a molecular mass of 28.3 kDa. The SP-10 antigen is not localized to the surface of sperm until after the acrosome reaction but it may be at this point that an antibody interaction with the exposed SP-10 would inhibit sperm-zona pellucida interaction leading to fertilization (Herr et al., 1989b).

An SP-10 fusion protein encoded by 640 nucleotides spanning an immunogenic portion of the SP-10 molecule linked as a fusion protein to a portion of bacterial beta galactosidase has been tested for immunogenicity in rabbits. Rabbits produced polyclonal antibodies which reacted with native SP-10 extracted from human sperm. These antibodies stained the human sperm acrosome. The rabbits did not suffer any ill effects from vaccination (Benjamin, D. C., et al., 1985).

Additionally, production of immunoglobulin A, presumably secretory IgA (sIgA), will block the ability of sperm to penetrate cervical mucus (Kremer and Jager, 1980) as well as inhibit sperm-zona pellucida interactions involved in the fertilization process (Dor et al., 1981; Bronson et al., 1982a, 1982b). A method of immunization that would stimulate a sIgA response, in addition to humoral and cellular immune responses, would therefore be most desirable.

The ovum-specific zona pellucida antigen, ZP-3, is one such antigen that could induce an sIgA response that would result in coating of the zona pellucida with sIgA, thus preventing fertilization by sperm. ZP-3 is unique to the maturing and mature oocytes and is important in sperm binding and induction of the acrosome reaction (Wasserman, 1987). Rabbits, dogs and monkeys immunized with porcine zona pellucida or ZP-3 had abnormal ovarian function and loss of follicles (Wood et al., 1981; Mahi-Brown et al., 1982). However, parenteral immunization of mice (Miller et al., 1989) with a ZP-3 B cell epitope fused to keyhole limpet hemocyanin, induces complete and reversible infertility in Swiss mice, but ovarian autoimmune disease and complete nonreversible infertility of B6AF1 female mice (Tung et al., 1991). Recently it has been possible to separate the epitopes on murine ZP-3 that induce the reversible infertility immune response from the one that induces autoimmune oophoritis (Tung et al., 1991). The use of such a peptide in a vaccine could provide an effective method for blocking fertilization without adverse consequences.

None of the above antigens, however, has been administered to a subject using avirulent carrier microbes. Certain avirulent carrier microbes which include foreign antigens have been shown to induce secretory, humoral and cellular immunities. These strains are developed by the introduction of mutations that cause the bacteria to be substantially incapable of producing functional proteins which are necessary for survival in a host. That is, these avirulent strains do not survive in a manner or for a duration that would cause impairment or a disease state in the host. Such mutants are disclosed in EPO Pub. No. 315,682 (published 17 May 1989), PCT Pub. No. WO 88/09669 (published 15 Dec. 1988) and in Curtiss and Kelly, 1987. Representative are mutants of Salmonella spp. which carry deletion mutations that impair the ability of the bacterium to synthesize adenylate cyclase (ATP pyrophosphate lyase (cyclizing) EC 4.6.1.1) (cya) and the cyclic AMP receptor protein (crp). In addition, removal of the S. typhimurium 91 kb virulence plasmid (Jones et al., 1982) effectively eliminates virulence and lethality following oral inoculation.

Mutants carrying either a point mutation or deletion of the gene encoding beta-aspartic semialdehyde dehydrogenase (asd) have also been developed. This enzyme is found in the mesodiamino-pimelic acid (DAP)-synthesis pathway. DAP is an essential component of peptidoglycan which imparts shape and rigidity to the bacterial cell wall. Bacteria carrying asd mutations can only survive in carefully controlled laboratory environments. Thus, a recombinant vector encoding both asd (an Asd$^+$ vector) and the antigen of interest, can be placed into an Asd$^-$ carrier cell. Only those cells encoding the desired antigen will survive. The use of such a carrier microbe to deliver a sperm specific antigen could result in an effective method of birth control.

DISCLOSURE OF THE INVENTION

The present invention is based on the discovery that certain avirulent microbes can serve as carriers of sperm-specific and ovum-specific antigens. Such microbes are useful in antifertility vaccines. These vaccines provide an effective method for preventing conception in a subject to which they are administered.

Accordingly, one embodiment of the invention is an avirulent microbe which includes a recombinant expression system which encodes at least one gamete-specific antigen.

Another embodiment of the invention is a vaccine composition comprising a therapeutically effective amount of the avirulent microbe in combination with a pharmaceutically acceptable vehicle.

In particularly preferred embodiments, the avirulent microbe lacks a functioning native chromosomal gene encoding beta-aspartate semialdehyde dehydrogenase (asd), and further comprises a recombinant gene encoding a functional asd polypeptide. The recombinant gene is linked to one or more genes encoding one or more gamete-specific antigens, particularly LDH-C, SP-10 and/or ZP-3, or epitopes thereof. The avirulent microbe also includes a mutated cya gene such that the microbe is substantially incapable of producing functional adenylate cyclase, as well as a mutated crp gene, rendering the microbe substantially incapable of producing functional cyclic AMP receptor protein.

In yet another embodiment, the subject invention is directed to a method for inducing an antifertility state in a vertebrate subject. The method comprises administering to the subject an effective amount of the above vaccine composition.

These and other embodiments of the present invention will readily occur to those of ordinary skill in the art in view of the disclosure herein.

BRIEF DESCRIPTION OF THE FIGURES

FIG. 1 depicts the cDNA sequence of the SP-10 coding region (and encoded protein, SEQ ID NO:56) and flanking sequences in the λgt11 clones SP-10-5 and SP-10-10 (Wright et al., 1989) (SEQ ID NO:1). 5' to the start of the SP-10-5 sequence at nucleotide 61 is an EcoRI hexanucleotide sequence and 3' to the SP-10-10 sequence at base pair 1091 is an EcoRI GAATTC hexanucleotide recognition sequence. The SP-10-10 sequence has an internal 57 base pair in-frame deletion indicated by brackets. Sites recognized by restriction enzymes used in the construction are identified. The arrow denotes the site for cleavage of the signal sequence.

FIG. 4 depicts the nucleotide sequence of Ptrc (SEQ ID NO:12) and the multiple cloning site in pYA810, which contains the coding sequence for the amino acid sequence, SEQ ID NO:57.

FIG. 12 depicts the construction of the MBP-LDH-C fusion and shows the N-terminal regions of the pMAL-cNOT vector and the pKKHC4 LDH-C gene with the addition of three amino acids to LDH-C following cleavage with Factor Xa.

FIG. 15 shows the construction of pYASP-10ter.

FIG. 16 shows the construction of pYALT-B-SP-10.

DETAILED DESCRIPTION OF THE INVENTION

Figure 2:
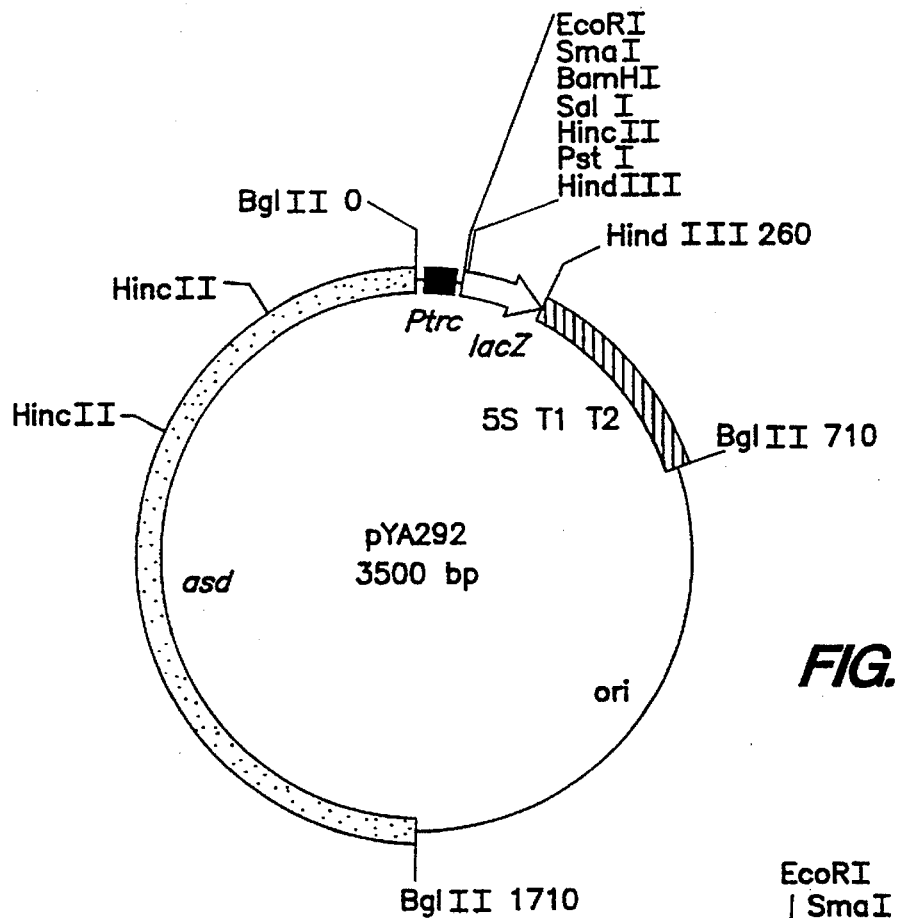
FIG. 2 is a diagram of the Asd$^+$ cloning vector pYA292.

The practice of the present invention will employ, unless otherwise indicated, conventional techniques of cell culture, molecular biology, microbiology, recombinant DNA, and immunology, which are within the skill of the art. Such techniques are explained fully in the literature. See, e.g., Sambrook, et al., Molecular Cloning: A Laboratory Manual, Second Edition (1989) Vols. 1–3; DNA Cloning (1985) Vols. I and II, D. N. Glover (ed.); Nucleic Acid Hybridization (1984), B. D. Hames, et al. (eds.); Perbal, B., A Practical Guide to Molecular Cloning (1984); Methods in Enzymology (the series), Academic Press, Inc.; Vectors: A Survey of Molecular Cloning Vectors and Their Uses (1987), R. L. Rodriguez, et al., (eds.), Butterworths; and Miller, J. H., et al., Experiments in Molecular Genetics (1972) Cold Spring Harbor Laboratory.

All patents, patent applications, and publications mentioned herein, whether supra or infra, are hereby incorporated by reference.

A. Definitions

An "antigen" refers to a molecule containing one or more epitopes that will stimulate a host's immune system to make a secretory, humoral and/or cellular antigen-specific response. The term is also used inter-changeably with "immunogen."

A "gamete-specific antigen" is one which elicits an immune response, as herein defined, directed against either ova or sperm. A "sperm-specific antigen" will elicit an immune response directed against sperm whereas an "ovum-specific antigen" will elicit an immune response directed against ova. Such gamete-specific antigens need not be derived from the species in which they are used so long as they are capable of eliciting the desired immune response. Examples of gamete-specific antigens are given below.

By "inducing an antifertility state" is meant creating an immune response in a subject such that fertilization is either hampered relative to fertilization rates normally found in a particular species, or prevented. Such an antifertility state need not be permanent, but may be reversible. However, the present invention also contemplates irreversible antifertility states (i.e. sterility).

A "hapten" is a molecule containing one or more epitopes that does not itself stimulate a host's immune system to make a secretory, humoral or cellular response.

The term "epitope" refers to the site on an antigen or hapten to which a specific antibody molecule binds. The term is also used interchangeably with "antigenic determinant" or "antigenic determinant site." An epitope will normally include 3 amino acids necessary for recognition in spatial confirmation, more usually 5 amino acids, and most usually 8–10 amino acids. An "epitope", as defined herein, is capable of eliciting an immune response in a subject to which it is administered.

An "immune response" to a composition or vaccine is the development in the host of a cellular and/or antibody-mediated immune response to the composition or vaccine of interest. Usually, such a response consists of the subject producing antibodies, B cells, helper T cells, suppressor T cells, and/or cytotoxic T cells directed specifically to an antigen or antigens included in the composition or vaccine of interest.

By "vaccine composition" is meant an agent used to stimulate the immune system of a living organism so that protection against future fertilization is provided. "Immunization" refers to the process of inducing a continuing high level of antibody and/or cellular immune response in which T-lymphocytes can either inactivate the antigen and/or activate other cells (e.g., phagocytes) to do so in an organism, which is directed against an antigen to which the organism has been previously exposed. Although the phrase "immune system" can encompass responses of unicellular organisms to the presence of foreign bodies, e.g., interferon production, in this application the phrase is restricted to the anatomical features and mechanisms by which a multi-cellular organism produces antibodies against an antigenic material which invades the cells of the organism or the extra-cellular fluid of the organism. The antibody so produced may belong to any of the immunological classes, such as immunoglobulins A, D, E, G or M.

Of particular interest are vaccines which stimulate production of immunoglobulin A (IgA) since this is the principle immunoglobulin produced by the secretory system of warm-blooded animals. Most pathogens colonize on or invade through a mucosal surface. The production of secretory IgA (sIgA) in various secretory glands, and appearing in secretions bathing the mucosal surfaces of the respiratory, gastrointestinal and genitourinary tracts, can serve to block the colonization and invasion of specific surface antigens that colonize on, and pass through, a mucosal surface. Immune response to antigens is well studied and widely reported. A survey of immunology is given in Barrett, James T., Textbook of Immunology: Fourth Edition, C. V. Mosby Co., St. Louis, Mo. (1983).

A "therapeutically effective amount" of a vaccine composition is a dose sufficient to either prevent or reduce fertility in a subject to which the composition is administered. The dosages of the present compositions which can prevent or reduce fertility can be determined in view of this disclosure by one of ordinary skill in the art by running routine trials with appropriate controls. Comparison of the appropriate treatment groups to the controls will indicate whether a particular dosage is effective in preventing or reducing fertility in a controlled challenge. In general, effective dosage will vary depending on the mode of administration. Appropriate doses are discussed further below.

A "vertebrate" is any member of the subphylum Vertebrata, a primary division of the phylum Chordata that includes the fishes, amphibians, reptiles, birds, and mammals, all of which are characterized by a segmented bony or cartilaginous spinal column. All vertebrates have a functional immune system and respond to antigens by producing antibodies.

An "individual" or "subject" administered a vaccine of the invention is defined herein as including all vertebrates, for example, mammals, including domestic animals and humans, various species of birds, including domestic birds, particularly those of agricultural importance.

By "avirulent derivative of a microbe" is meant an organism which is substantially incapable of causing disease in a host being treated with the particular avirulent microbe. An "avirulent microbe", as used herein, is derived from a pathogenic microbe and capable of colonizing a lymphoreticular tissue. By "pathogenic" is meant capable of causing disease or impairing normal physiological functioning. Avirulent strains are incapable of inducing a full suite of symptoms of the disease that is normally associated with its virulent pathogenic counterpart. The term "microbe" as used herein includes bacteria, protozoa, and unicellular fungi. Derivatives of avirulent microbes are also contemplated to be within the scope of this invention. By derivative is meant sexually or asexually derived progeny and mutants of the avirulent strains including single or multiple base substitutions, deletions, insertions or inversions.

A "carrier microbe" is an avirulent microbe as defined above which contains and expresses a recombinant gene encoding a protein of interest such as a gamete-specific antigen.

A "recombinant gene" is an identifiable segment of a polynucleotide within a larger polynucleotide molecule that is not found in association with the larger molecule in nature.

A "replicon" is any genetic element (e.g., plasmid, chromosome, virus) that functions as an autonomous unit of DNA replication in vivo; i.e., capable of replication under its own control.

A "vector" is a replicon, such as a plasmid, phage, or cosmid, to which another DNA segment may be attached so as to bring about the replication of the attached segment.

A DNA "coding sequence" is a DNA sequence which is transcribed and translated into a polypeptide in vivo when placed under the control of appropriate regulatory sequences. The boundaries of the coding sequence are determined by a start codon at the 5' (sunino) terminus and a translation stop codon at the 3' (carboxy) terminus. A coding sequence can include, but is not limited to, procaryotic sequences, cDNA from eucaryotic mRNA, genomic DNA sequences from eucaryotic (e.g., mammalian) DNA, and even synthetic DNA sequences. A transcription termination sequence will usually be located 3' to the coding sequence.

A "promoter sequence" is a DNA regulatory region capable of binding RNA polymerase in a cell and initiating transcription of a downstream (3' direction) coding sequence. For purposes of defining the present invention, the promoter sequence is bound at the 3' terminus by the translation start codon (ATG) of a coding sequence and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eucaryotic promoters will often, but not always, contain "TATA" boxes and "CAT" boxes. Procaryotic promoters contain Shine-Dalgarno sequences in addition to the −10 and −35 consensus sequences.

DNA "control sequences" refers collectively to promoter sequences, ribosome binding sites, polyadenylation signals, transcription terminate on sequences, upstream regulatory domains, enhancers, and the like, which collectively provide for the transcription and translation of a coding sequence in a host cell.

A coding sequence is "operably linked to" or "under the control of" control sequences in a cell when RNA polymerase will bind the promoter sequence and transcribe the coding sequence into mRNA, which is then translated into the polypeptide encoded by the coding sequence.

"Recombinant host cells", "host cells", "cells" and other such terms denoting microorganisms are used interchangeably, and refer to cells which can be, or have been, used as recipients for recombinant vectors or other transferred DNA, and include the progeny of the original cell transfected. It is understood that the progeny of a single parental cell may not necessarily be completely identical in genomic or total DNA complement as the original parent, due to accidental or deliberate mutation. Progeny of the parental cell which are sufficiently similar to the parent to be characterized by the relevant property, for example, the substitution of a native gene encoding an essential enzyme with a cloned gene linked to a structural gene encoding a desired gene product.

A "clone" is a population of cells derived from a single cell or common ancestor by cell division. A "cell line" is a clone of a primary cell that is capable of stable growth in vitro for many generations.

A "gene library" is a collection of cloned genes, generally comprising many or all of the genes from a particular species. Libraries are made by treating DNA with selected restriction endonucleases, followed by cloning the fragments into a suitable vector. Gene libraries can be searched using a homologous sequence of DNA from a related organism in order to identify the clone within the library which represents the desired gene.

A "heterologous" region of a DNA construct is an identifiable segment of DNA within or attached to another DNA molecule that is not found in association with the other molecule in nature. Thus, when the heterologous region encodes a bacterial gene, the gene will usually be flanked by DNA that does not flank the bacterial gene in the genome of the source bacteria. Another example of the heterologous coding sequence is a construct where the coding sequence itself is not found in nature (e.g., synthetic sequences having codons different from the native gene). Allelic variation or naturally occurring mutational events do not give rise to a heterologous region of DNA, as used herein.

"Transformation", as used herein, refers to the insertion of an exogenous polynucleotide into a host cell, irrespective of the method used for the insertion, for example, direct uptake, transduction, or conjugation. The exogenous polynucleotide may be maintained as a plasmid, or alternatively, may be integrated within the host genome.

B. General Methods

Figure 1A:
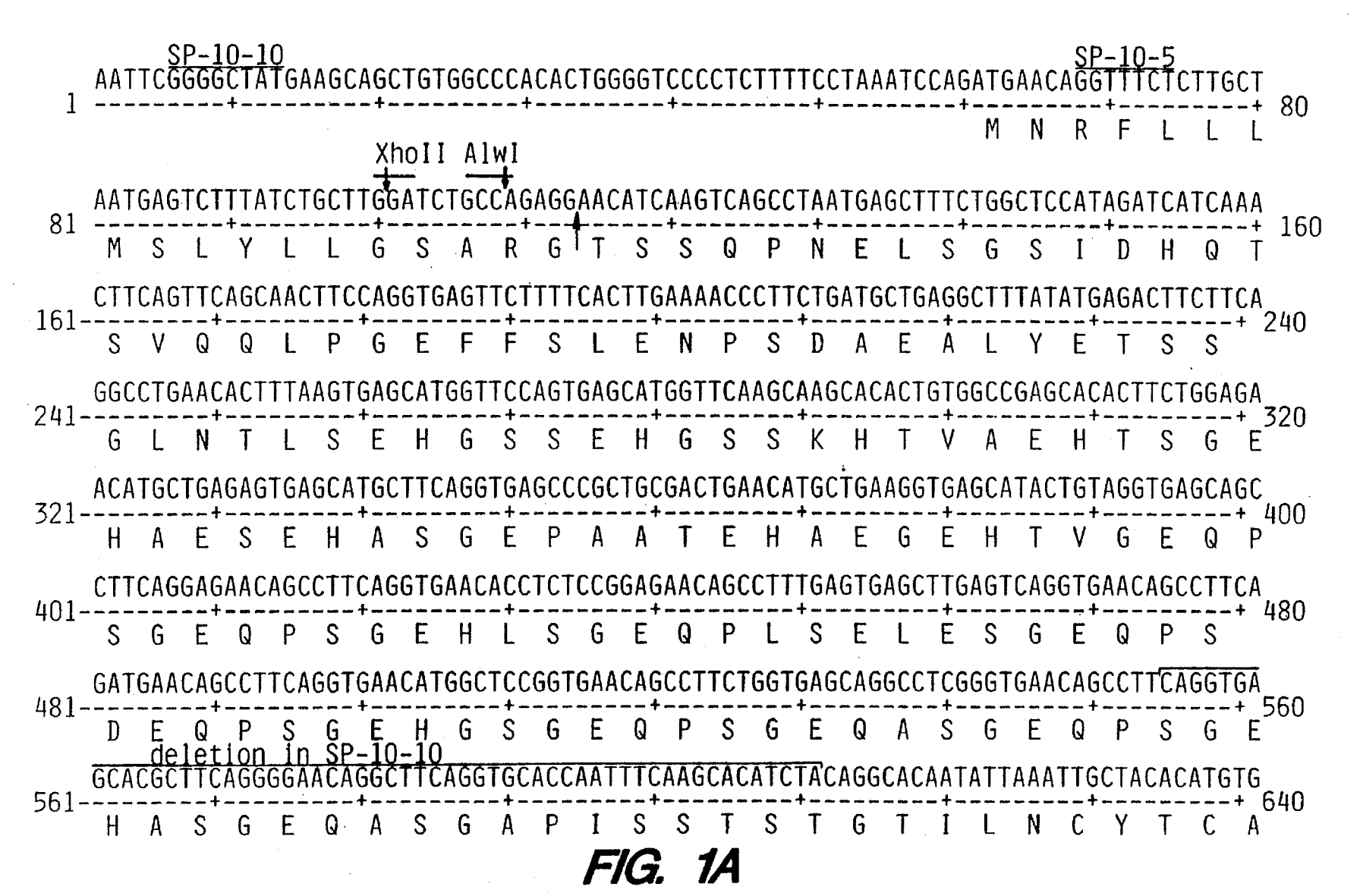

This invention relates to microbial vaccines containing gamete-specific antigens capable of reducing or eliminating fertilization in a subject to which they are administered. Several sperm-specific antigens are known, such as PHG-20, SP-10, LDH-C, LDH-X, the $M_1$ 95,000 antigen of Moore, the 55 kDa antigen recognized by the S36-37 mAbs (HSA-63), of Lee, human homologs of 95 kDa and 56 kDa sperm receptors for ZP-3, FA-1, and the 24 kDa antigen characterized by Shaha (all described above), and FA-1 (Naz 1987, 1988), and will find use with the instant invention. The nucleotide sequence for SP-10 is depicted in FIG. 1. Furthermore, the cDNA for the human testes-specific lactic dehydrogenase has been cloned and its antigenic sites characterized. (Millan et al., 1987; Hogrefe et al., 1987; Goldberg, 1987; Hogrefe et al., 1989). Similarly, ovum-specific antigens are known, such as the zona pellucida antigens, ZP-1, ZP-2 and ZP-3, and epitopes within ZP-3 identified (Tung et al., 1991).

Figure 17:
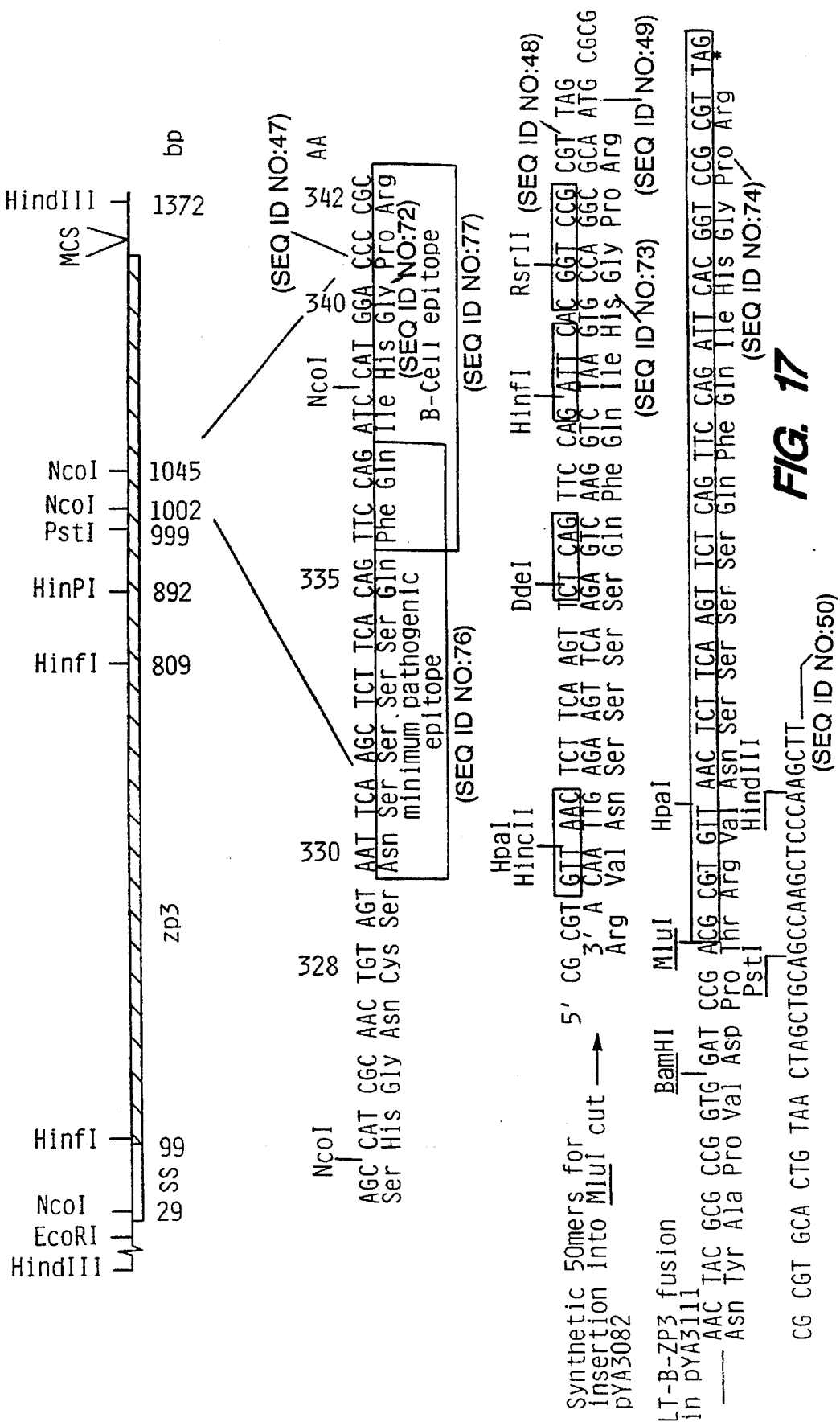
FIG. 17 depicts the construction of an LT-B-ZP3 fusion and shows the coding region of the murine ZP3 clone pZP3.3, as well as the toxic epitope region and the synthetic oligomer. The numbers below the restriction sites show the relative position in base pairs (bp) within ZP3, the numbers above the expanded region indicate the amino acid positions (AA).

One or more of the genes encoding these and other gamete-specific antigens, can be placed into avirulent microbes for delivery to an appropriate subject. The entire DNA sequence encoding the particular gamete-specific antigen need not be present in the microbial carrier, so long as a gene encoding at least one epitope is included such that an immune response is elicited in a subject administered the microbial vaccine. Indeed, with regard to ZP-3, if a reversible antifertility state is desired, it is preferable to delete the antigenic determinant responsible for inducing autoimmune pathology (the pathogenic epitope shown in FIG. 17) from the protein and immunize a subject with the remaining protein or with epitopes shown to induce the infertility immune response. Such epitopes have been identified (FIG. 17 and Tung et al., 1991). The inclusion of the pathogenic region of ZP-3 in an antifertility vaccine will find use when permanent sterilization is desired.

Other gamete-specific antigens will also find use with the instant invention and can be readily identified using techniques well known in the art. The genes encoding these antigens can be inserted into a carrier microbe, as described further below, and the transformed microbe used in a vaccine to reduce or eliminate fertilization in a recipient host.

Specifically, gamete-specific antigens can be identified and prepared and the genes specifying them cloned. First, cDNA libraries can be prepared using cDNA generated from mRNA isolated from testicular or ovarian tissues and crude preparations can be used to raise antibodies which can in turn be used for recombinant expression screening. Thus, clones expressing proteins reactive with these antibodies can be identified and these proteins further characterized.

The individual cDNA recombinant clones expressing proteins that react with antisera against human gamete-specific antigens can be subcloned into a suitable plasmid expression vector to overproduce the protein antigen. The antigen can then be purified using conventional protein purification methods following release of the protein antigen from recombinant E. coli cells. Antisera against the protein can be prepared by injection of antigen into a mouse for efficiency or into a rabbit where larger amounts of antisera might be desired. In initial screens, these antisera are used to identify protein antigens by Western blot analysis in human gametes after separation on SDS polyacrylamide gels. In this way, it is possible to determine whether the cDNA cloned specifies the entire coding sequence for the antigen and produces a product of a size as isolated from gametes. Of course, adjustments for glycosylation of the protein present in the gamete will be necessitated. This analysis will also reveal the number of independent clones specifying individual antigens and will enable grouping of cDNA clones specifying parts of the same protein antigen.

An important and essential analysis involves the determination of whether the antisera raised against the antigen produced by the recombinant organism does or does not react with other human tissue. This is important since the presence of an antigen in any human tissues other than gametes, and especially in embryonic tissue, would be unacceptable. In other words, it is of extreme importance that the gamete-specific antigen to be expressed in the recombinant avirulent vaccine construct for oral immunization of the human not induce antibodies that would interact with human tissues and especially would not react with any tissues in a fertilized egg or in the embryo.

It is possible that the cDNA libraries produced above would not be derived from mRNAs involved in specifying all of the unique antigenic components present in human gametes. For this reason, a different approach to obtaining DNA sequences encoding these gamete-specific antigens can be taken. This involves the biochemical purification of individual antigens.

The isolated proteins can be sequenced by any of the various methods known to those skilled in the art. For example, the amino acid sequences of the subject proteins can be determined from the purified proteins by repetitive cycles of Edman degradation, followed by amino acid analysis by HPLC. Other methods of amino acid sequencing are also known in the art.

The amino acid sequences determined by the above method may be used to design oligonucleotide probes which contain the codons for a portion of the determined amino acid sequences which can be used to screen DNA libraries for genes encoding the subject proteins. The basic strategies for preparing oligonucleotide probes and DNA libraries, as well as their screening by nucleic acid hybridization, are well known to those of ordinary skill in the art. See, e.g., DNA Cloning: Vol. I, supra; Nucleic Acid Hybridization, supra; Oligonucleotide Synthesis, supra; Sambrook, et al., supra.

First, a DNA library is prepared. Once the library is constructed, oligonucleotides to probe the library are prepared and used to isolate the gene encoding the gamete-specific antigen. The oligonucleotides are synthesized by any appropriate method. The particular nucleotide sequences selected are chosen so as to correspond to the codons encoding a known amino acid sequence from the desired gamete-specific antigen. Since the genetic code is degenerate, it will often be necessary to synthesize several oligonucleotides to cover all, or a reasonable number, of the possible nucleotide sequences which encode a particular region of the protein. Thus, it is generally preferred in selecting a region upon which to base the probes, that the region not contain amino acids whose codons are highly degenerate. In certain circumstances, one of skill in the art may find it desirable to prepare probes that are fairly long, and/or encompass regions of the amino acid sequence which would have a high degree of redundancy in corresponding nucleic acid sequences, particularly if this lengthy and/or redundant region is highly characteristic of the protein of interest. It may also be desirable to use two probes (or sets of probes), each to different regions of the gene, in a single hybridization experiment. Automated oligonucleotide synthesis has made the preparation of large families of probes relatively straight-forward. While the exact length of the probe employed is not critical, generally it is recognized in the art that probes from about 14 to about 20 base pairs are usually effective. Longer probes of about 25 to about 60 base pairs are also used.

The selected oligonucleotide probes are labeled with a marker, such as a radionucleotide or biotin using standard procedures. The labeled set of probes is then used in the screening step, which consists of allowing the single-stranded (ss) probe to hybridize to isolated ssDNA from the library, according to standard techniques. Either stringent or permissive hybridization conditions could be appropriate, depending upon several factors, such as the length of the probe and whether the probe is derived from the same species as the library, or an evolutionarily close or distant species. The selection of the appropriate conditions is within the skill of the art. See generally, Nucleic Acid Hybridization, supra. The basic requirement is that hybridization conditions be of sufficient stringency so that selective hybridization occurs; i.e., hybridization is due to a sufficient degree of nucleic acid homology (e.g., at least about 75%), as opposed to nonspecific binding. Once a clone from the screened library has been identified by positive hybridization, it can be confirmed by restriction enzyme analysis and DNA sequencing that the particular library insert contains a gene for the desired protein.

Alternatively, DNA sequences encoding the antigen of interest can be prepared synthetically rather than cloned. The DNA sequence can be designed with the appropriate codons for the particular gamete-specific amino acid sequence. In general, one will select preferred codons for the intended host if the sequence will be used for expression. The complete sequence is assembled from overlapping oligonucleotides prepared by standard methods and assembled into a complete coding sequence. See, e.g., Edge, Nature (1981) 292:756; Nambair et al., Science (1984) 223:1299; Jay et al., J Biol Chem (1984) 259:6311.

Once a coding sequence for the desired protein has been prepared or isolated, it can be cloned into any suitable vector or replicon. Numerous cloning vectors are known to those of skill in the art, and the selection of an appropriate cloning vector is a matter of choice. Examples of recombinant DNA vectors for cloning and host cells which they can transform include the bacteriophage lambda (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (Bacillus), pIJ61 (Streptomyces), pUC6 (Streptomyces), YIp5 (Saccharomyces), YCp19 (Saccharomyces) and bovine papilloma virus (mammalian cells). See, generally, DNA Cloning: Vols. I & II, supra; Sambrook, et al., supra; Perbal, B., supra.

The coding sequence for the gamete-specific protein of interest can be placed under the control of a promoter, ribosome binding site (for bacterial expression) and, optionally, an operator (collectively referred to herein as "control" elements), so that the DNA sequence encoding the protein is transcribed into RNA in the host cell transformed by a vector containing this expression construction. The coding sequence may or may not contain a signal peptide or leader sequence. The gamete-specific antigens of the present invention can be expressed using, for example, a native promoter or other well known promoters that function in gram negative bacteria such as the tac or trc promoters.

The gamete-specific antigens, when present in a carrier microbe, may be expressed under the control of a promoter that only allows expression in vivo in the immunized host. However, if production of the protein is desired in bulk, outside of the intended recipient, in addition to control sequences, it may be desirable to add regulatory sequences which allow for regulation of the expression of the antigen sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

Figure 9A:
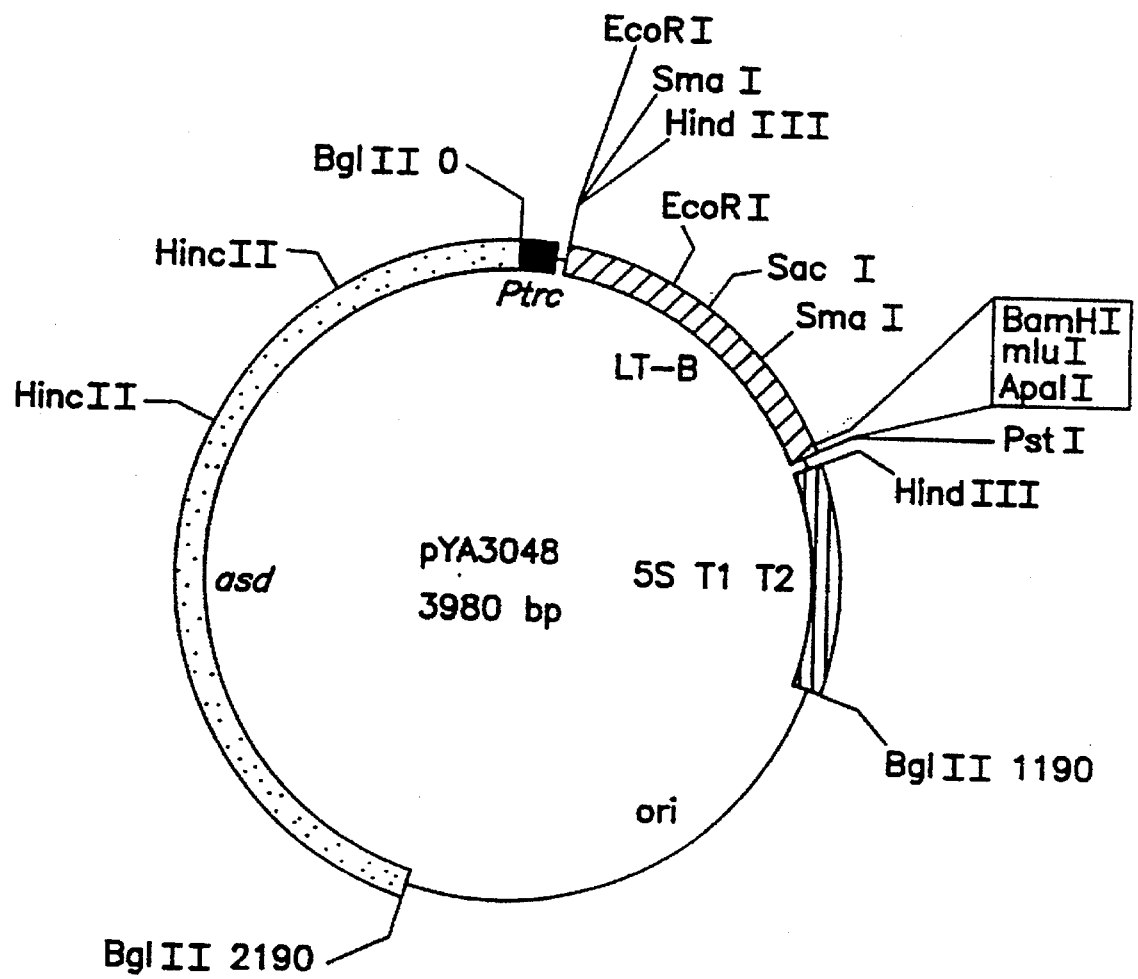
FIG. 9 is a diagram of plasmid pYA3048. 9A shows the LT-B gene cloned into the BamHi to PstI site of pYA810. A 38 bp linker is present at the 3' end of the LT-B gene to give unique BamHI, MluI and ApaLI sites. 9B shows the multiple cloning sites in the nucleotide sequence (SEQ ID NO:14) encoding amino acid sequence, SEQ ID NO:59 at the C-terminal end of the LT-B sequence in pYA3048. Asn is the C-terminal amino acid in LT-B. The * denote the two stop codons, each in different reading frame.
Figure 10A:
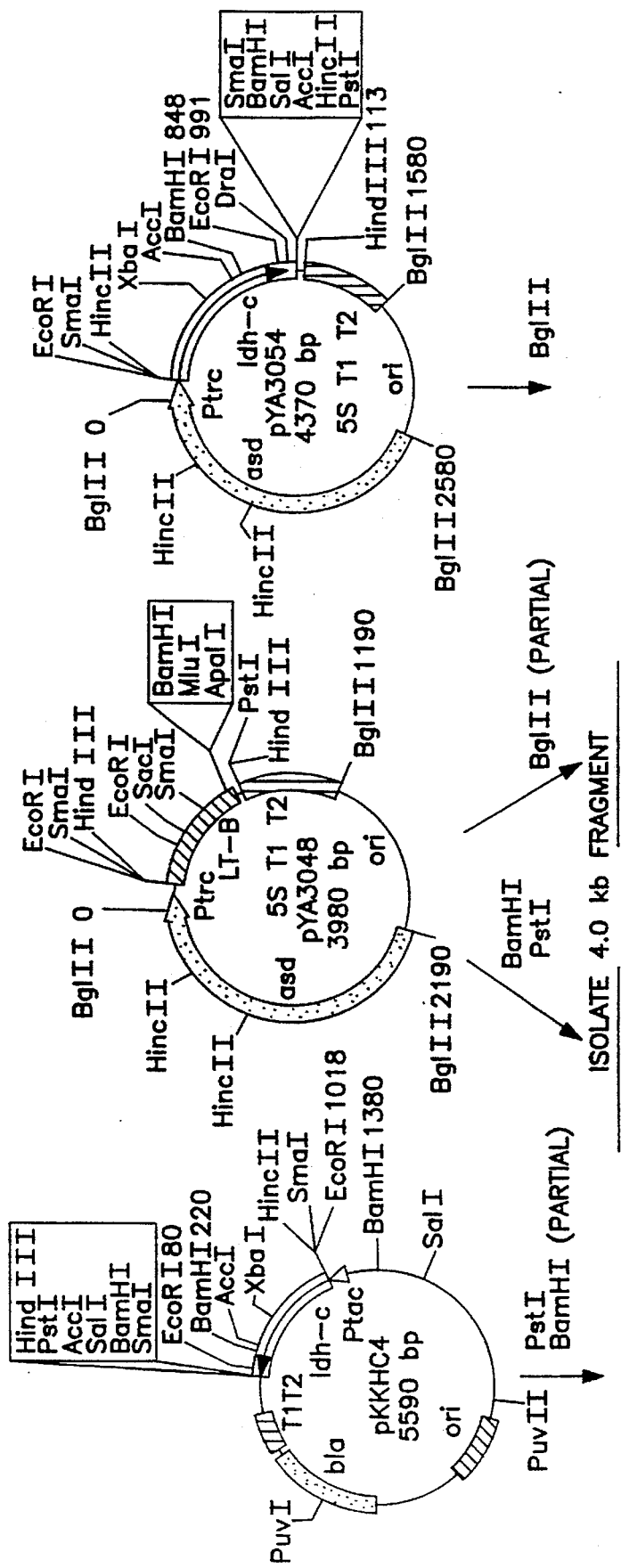
FIG. 10 depicts the pYA3095 and pYA3097 LT-B and LDH-C coexpression constructs and the construction thereof.
Figure 11:
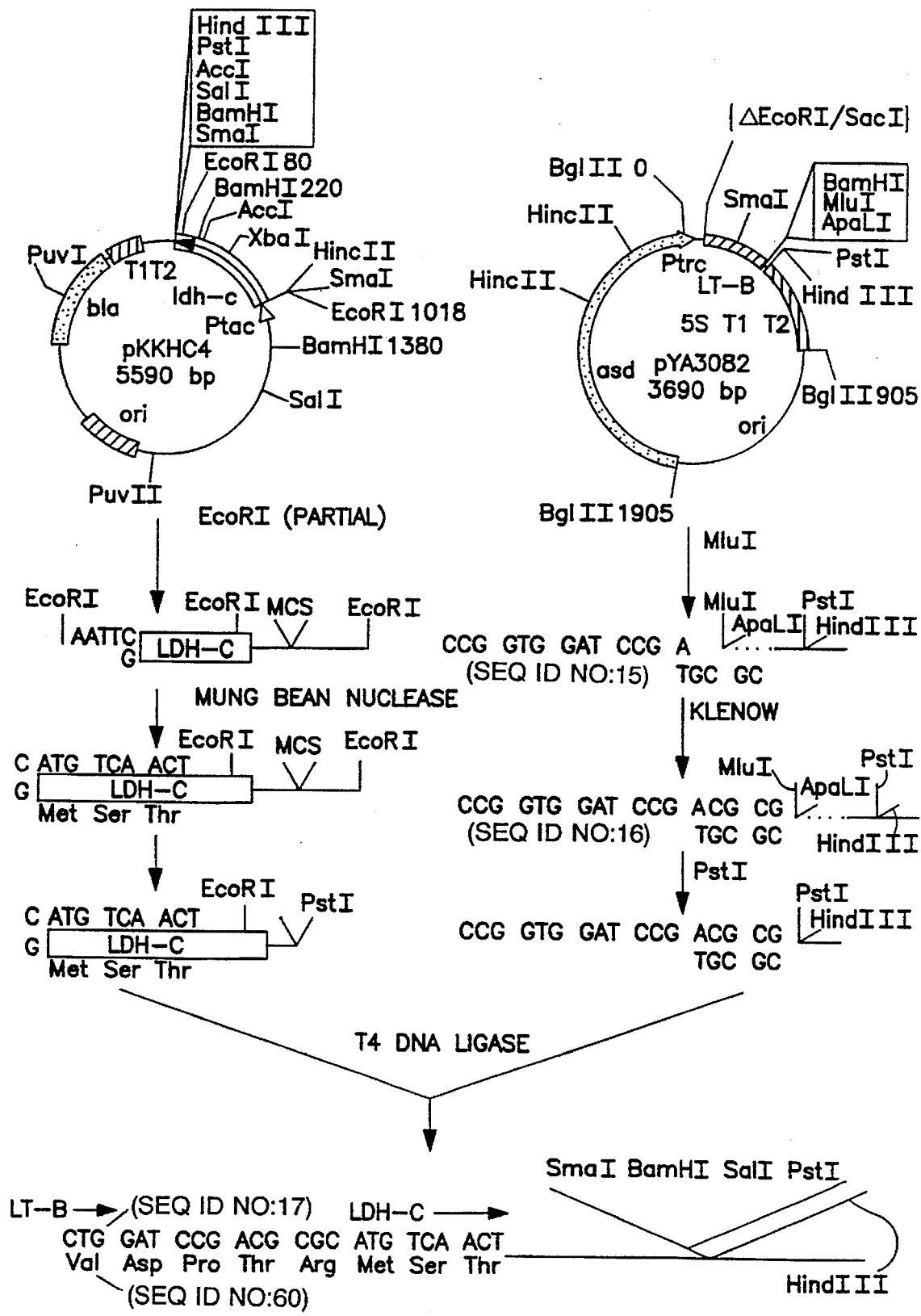
FIG. 11 shows the construction of a LT-B-human LDH-C fusion plasmid using pKKHC4 and pYA3082.

The subject proteins can also be expressed in the form of fusion proteins, wherein a heterologous amino acid sequence is expressed at either the C-terminal or the N-terminal end of the fusion protein. See, e.g., U.S. Pat. Nos. 4,431,739; 4,425,437. For example, the sequence encoding the desired antigen can be fused with sequences specifying an adjuvant peptide that contains suitable antigenic determinants to enhance the secretory immune response against the antigen of interest. Specific examples of such adjuvant peptides include the B-subunit of the heat labile toxin produced by enterotoxogenic *E. coli* (LT-B) and the cholera toxin B subunit (CT-B) (Elson, 1988; Holmgren et al., 1988). Vectors have been designed which constitutively express these peptides and possess multiple cloning sites to permit fusion of nucleotide sequences encoding desired antigens at either the C-terminal or N-terminal end of the adjuvant sequences (see FIGS. 9A, 9B and 11).

An expression vector is constructed so that the particular coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). Modification of the sequences encoding the particular antigen of interest may be desirable to achieve this end. For example, in some cases it may be necessary to modify the sequence so that it may be attached to the control sequences with the appropriate orientation; i.e., to maintain the reading frame. The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

In some cases, it may be desirable to add leader sequences which cause the secretion of the polypeptide from the host organism, with subsequent cleavage of the secretory signal, if any. Leader sequences can be removed by the bacterial host in post-translational processing. See, e.g., U.S. Pat. Nos. 4,431,739; 4,425,437; 4,338,397. It may also be desirable to produce mutants or analogs of the antigen of interest. Mutants or analogs may be prepared by the deletion of a portion of the sequence encoding the antigen, by insertion of a sequence, and/or by substitution of one or more nucleotides within the sequence. For example, proteins used to immunize a host may contain epitopes that stimulate helper cells as well as epitopes that stimulate suppressor cells. Thus, deletion or modification of these latter nucleotides would be desirable. Techniques for modifying nucleotide sequences, such as site-directed mutagenesis, are well known to those skilled in the art. See, e.g., Sambrook, et al., supra; DNA Cloning, Vols. I and II, supra; Nucleic Acid Hybridization, supra.

A number of procaryotic expression vectors are known in the art. See, e.g., U.S. Pat. Nos. 4,440,859; 4,436,815; 4,431,740; 4,431,739; 4,428,941; 4,425,437; 4,418,149; 4,411,994; 4,366,246; 4,342,832; see also U.K. Patent Applications GB 2,121,054; GB 2,008,123; GB 2,007,675; and European Patent Application 103,395.

Depending on the expression system and host selected, the gamete-specific antigens of the present invention are produced by growing host cells transformed by an expression vector described above under conditions whereby the protein of interest is expressed. The particular protein can be isolated from the host cells and purified in order to monitor the immune response of immunized animals. If the expression system secretes the protein into growth media, the protein can be purified directly from the media. If the protein is transported to the periplasmic space, it can be released to the medium by cold osmotic shock, a technique well known in the art. If the protein is not secreted or transported to the periplasmic space, it is isolated from cell lysates. The selection of the appropriate growth conditions and recovery methods are within the skill of the art.

The proteins of the present invention or their fragments can be used to produce antibodies, both polyclonal and monoclonal. If polyclonal antibodies are desired, a selected bird or mammal, (e.g., chicken, turkey, mouse, rabbit, goat, horse, etc.) is immunized with an antigen of the present invention, or its fragment, or a mutated antigen. Serum from the immunized animal is collected and treated according to known procedures. If serum containing polyclonal antibodies to the protein of interest contains antibodies to other antigens, the polyclonal antibodies can be purified by immunoaffinity chromatography, using known procedures.

Monoclonal antibodies to the proteins of the present invention, and to the fragments thereof, can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. See, e.g., Schreier, M., et al., Hybridoma Techniques (1980); Hammerling et al., Monoclonal Antibodies and T-cell Hybridomas (1981); Kennett et al., Monoclonal Antibodies (1980); See also U.S. Pat. Nos. 4,341,761; 4,399,121; 4,427,783; 4,444,887; 4,452,570; 4,466,917; 4,472,500, 4,491,632; and 4,493,890. Panels of monoclonal antibodies produced against the antigen of interest, or fragment thereof, can be screened for various properties; i.e., for isotype or epitope affinity, etc. Monoclonal antibodies are useful in purification, using immunoaffinity techniques, of the antigens which they are directed against.

The gamete-specific antigens of the present invention, produced as described above, can be used to immunize subjects to produce an antifertility state. Avirulent carrier microbes are used to administer the present antigens. This method of administration is particularly suitable since appropriate carrier microbes can stimulate production of sIgA. The production of sIgA in various secretory glands and appearing in secretions bathing the mucosal surfaces of the respiratory, gastrointestinal and genitourinary tracts can serve to block the colonization and invasion of specific surface antigens that colonize on, and pass through, a mucosal surface. Anti-gamete sIgA production in the genital tract blocks the ability of sperm to penetrate cervical mucous (Kramer and Jager, 1980) as well as inhibits sperm-zona pellucida interactions involved in the fertilization process (Dor et al., 1981; Broson et al., 1982ab).

Recombinant plasmids containing one or more genes for the gamete-specific antigens can be introduced into one of several avirulent strains of bacteria containing mutations for genes necessary for long-term survival in the targeted host. Useful avirulent microbes include, but are not limited to, mutant derivatives of Salmonella and E. coli-Salmonella hybrids. Preferred microbes are members of the genus Salmonella such as S. typhimurium, S. typhi, S. paratyphi, S. gallinarum, S. pullorum, S. enteritidis, S. choleraesuis, S. arizona, or S. dublin. Avirulent derivatives of S. typhimurium and S. enteritidis find broad use among many hosts. Avirulent derivatives of S. gallinarum, S. pullorum and S. arizona may be particularly useful for immunizing avian species whereas S. typhimurium, S. typhi and S. paratyphi are preferred for use in humans. S. choleraesuis is preferably used to immunize swine while S. dublin finds use in cattle. The creation of such mutants is described in copending patent application Ser. No. 251,304 and in Curtiss and Kelly, 1987.

Particularly useful are the cya, crp and asd mutants described above which are substantially incapable of producing the corresponding functional protein in a host, such that growth is impaired. However, other avirulent microbes will also find use with the present invention. Such avirulent microbes would include those with aroA, aroC, aroD, galE, phoP, cdt, ompR and htrA mutations. If Asd$^-$ mutants are used, the gamete-specific antigen of interest is transferred to the carrier microbe using a vector encoding both the gamete-specific antigen and asd. Thus, only those carrier microbes containing the desired gamete-specific antigen will survive and these microbes can be selected for further use. FIG. 2 depicts a map of pYA292 Asd$^+$, a vector into which a gene encoding the desired gamete-specific antigen can be cloned. This vector can then be transferred into an Asd$^-$ carrier microbe. Expression of the recombinant gene encoding the desired antigen may be dependent on a control sequence linked to the asd gene. This linkage may result from the orientation of the two genes in the vector so that both genes could be, for example, under the control of the same control elements, i.e., the same promoter and operator.

The cya mutants and/or crp mutants can be further mutated, preferably by a deletion, in a gene adjacent to the crp gene which governs virulence of Salmonella. Mutation in this gene, the cdt gene, diminishes the ability of the bacteria to effectively colonize deep tissues, e.g., the spleen. When a plasmid having the crp$^+$ gene is placed in a strain with the Δ(crp-cdt), it retains its avirulence and immunogenicity thus having a phenotype similar to cya and crp mutants. Mutants with the Δ(crp-cdt) mutation containing a crp$^+$ gene on a plasmid retain the normal ability to colonize the intestinal tract and GALT, but have a diminished ability to colonize deeper tissues. In the Examples, the original Δ(crp-cdt) mutation as isolated in χ3622 which also has deleted the argD and cysG genes imposing requirements for arginine and cysteine for growth; this mutant allele has been named Δ(crp-cysG)-10. A second mutant containing a shorter deletion was isolated that did not impose an arginine requirement; it is present in χ3931 and has been named Δ(crp-cysG)-14.

Introduction of the described mutations into a particular microbe can be accomplished by use of transposons, to transfer the mutations from other mutated strains into the strain of interest. Transposons can be added to a bacterial chromosome at many points. The characteristics of transposon insertion and deletion have been reviewed in Kleckner et al. (1977), J. Mol. Biol. 116:125. For example, the transposon Tn10, which confers resistance to tetracycline (and sensitivity to fusaric acid) can be used to create Δcya and ΔCrp mutations in a variety of bacterial species, including, for example, *E. coli* and *S. typhimurium*. Methods for the creation and detection of these mutants in *S. typhimurium* are described in EPO Pub. No. 315,682, and a method is also provided in the Examples, infra. Utilizing Tn10, these mutations can be transposed into various isolates of Salmonella, preferably those which are highly pathogenic.

The creation of bacterial mutants can also be accomplished using other techniques known in the art. These techniques include for example, standard techniques of mutagenesis and/or the use of recombinant DNA techniques. The desired mutants are then selected on the basis of phenotypic characteristics, some of which are described infra., in the Examples. Methods of constructing vectors with these characteristics are discussed more fully in copending patent application Ser. No. 251,304 and commonly owned, copending patent application Ser. No. 07/612,001, filed 9 Nov. 1990.

In order to stimulate a preferred immune response, introduction of the microbe or gene product directly into the gut or bronchus is preferred, such as by oral administration, intranasal administration, gastric intubation or in the form of aerosols, as well as air sac inoculation (in birds only), and intratracheal inoculation. Other suitable methods include administration via the conjuctiva to reach the Harder gland and intramammary inoculation. Other methods of administering the vaccine, such as intravenous, intramuscular, or subcutaneous injection are also possible, and used principally to stimulate a secondary immune response, as described further below.

Generally, when carrier microbes expressing the gamete-specific antigens are administered to humans or other mammals, they will be present in a pharmaceutically acceptable vehicle. For example, the carrier microbes can be enteric-coated or encapsulated with a suitable gelatin-like substance, known in the art (Cryz and Glück, 1990, in G. Woodrow and Mr. Levine, New Generation Vaccines, Marcel Dekker, New York, pp. 921–932).

Once the carrier microbe is present in the animal, the antigen needs to become available to the animal's immune system. This may be accomplished when the carrier microbe dies so that the antigen molecules are released. Of course, the use of "leaky" avirulent mutants that release the contents of the periplasm without lysis is also possible. Alternatively, a gene may be selected that controls the production of an antigen that will be made available by the carrier cell to the outside environment prior to the death of the cell.

The antigens may also be administered as aerosols or intranasally. Intranasal formulations for human subjects will usually include vehicles that neither cause irritation to the nasal mucosa nor significantly disturb ciliary function. Diluents such as water, aqueous saline or other known substances can be employed with the subject invention. The nasal formulations may also contain preservatives such as but not limited to chlorobutanol and benzalkonium chloride. A surfactant may be present to enhance absorption of the subject proteins by the nasal mucosa.

Injection of the gamete-specific antigen can also be done in conjunction with prior oral, intranasal, gastric or aerosol immunization. Such parenteral immunization can serve as a booster to enhance expression of the secretory immune response once the secretory immune system to the gamete-specific gene product has been primed by immunization with the carrier microbe expressing the gamete-specific gene product. The enhanced response is known as a secondary, booster, or anamnestic response and results in prolonged immune protection of the host. Booster immunizations may be repeated numerous times with beneficial results.

When the vaccines are prepared as injectables, such as for boosters, they can be made either as liquid solutions or suspensions; solid forms suitable for solution in, or suspension in, liquid vehicles prior to injection may also be prepared. The preparation may also be emulsified or the active ingredient encapsulated in liposome vehicles. The active immunogenic ingredient is often mixed with vehicles containing excipients which are pharmaceutically acceptable and compatible with the active ingredient. Suitable vehicles are, for example, water, saline, dextrose, glycerol, ethanol, or the like, and combinations thereof. In addition, if desired, the vehicle may contain minor amounts of auxiliary substances such as wetting or emulsifying agents, pH buffering agents, or adjuvants which enhance the effectiveness of the vaccine. Adjuvants may include for example, muramyl dipeptides, avridine, aluminum hydroxide, oils, saponins and other substances known in the art. Actual methods of preparing such dosage forms are known, or will be apparent, to those skilled in the art. See, e.g., Remington's Pharmaceutical Sciences, Mack Publishing Company, Easton, Pa., 15th ed., 1975. The composition or formulation to be administered will, in any event, contain a quantity of the protein adequate to achieve the desired immunized state in the individual being treated.

The quantity of antigen to be administered depends on the subject to be treated, the capacity of the subject's immune system to synthesize antibodies, and the degree of protection desired. Effective dosages can be readily established by one of ordinary skill in the art through routine trials establishing dose response curves. The subject is immunized by administration of the particular antigen or fragment thereof, or analog thereof, in at least one dose. Typical doses using the carrier microbe are on the order of $1\times10^6$–$1\times10^{10}$ recombinant avirulent bacteria/immunized subject. The subject may be administered increasing amounts or multiple dosages as required to maintain a state of immunity to the gamete-specific antigen.

It may be desireable to administer more than one gamete-specific antigen simultaneously or consecutively. This can be accomplished either by administering an avirulent carrier containing genes encoding for more than one gamete-specific antigen or by administering different carrier organisms.

The above disclosure generally describes the present invention. A more complete understanding can be obtained by reference to the following specific examples, which are offered for illustrative purposes only, and are not intended to limit the scope of the present invention in any way.

Deposits of Strains Useful in Practicing the Invention

A deposit of biologically pure cultures of the following strains were made with the American Type Culture Collection, 12301 Parklawn Drive, Rockville, Md. The accession number indicated was assigned after successful viability testing, and the requisite fees were paid. Access to said cultures will be available during pendency of the patent application to one determined by the Commissioner to be entitled thereto under 37 CFR 1.14 and 35 USC 122. All restriction on availability of said cultures to the public will be irrevocably removed upon the granting of a patent based upon the application. Moreover, the designated deposits will be maintained for a period of thirty (30) years from the date of deposit, or for five (5) years after the last request for the deposit; or for the enforceable life of the U.S. patent, whichever is longer. Should a culture become nonviable or be inadvertently destroyed, or, in the case of plasmid-containing strains, loose its plasmid, it will be replaced with a viable culture(s) of the same taxonomic description. The deposited materials mentioned herein are intended for convenience only, and are not required to practice the present invention in view of the description herein, and in addition, these materials are incorporated herein by reference.

| Strain | Deposit Date | ATCC No. |
|---|---|---|
| χ4072 | Oct. 6, 1987 | 67538 |
| pYA292 Asd+ in χ6097 | Sept. 26, 1988 | 67813 |
| pYA3042 in χ3987 | Nov. 16, 1990 | 68479 |
| 3958 | Nov. 2, 1990 | 55110 |
| χ4323 | Nov. 2, 1990 | 55115 |
| χ3926 | Nov. 2, 1990 | 55112 |
| χ3927 | Nov. 2, 1990 | 55117 |
| χ4297 | Nov. 2, 1990 | 55111 |
| χ4346 | Nov. 2, 1990 | 55113 |
| χ3940 | Nov. 2, 1990 | 55119 |
| χ4073 | Nov. 2, 1990 | 55118 |
| ISP2822 | Nov. 2, 1990 | 55114 |
| ISP1820 pYA3054 in χ3987 pYA3111 in χ3987 pYA3112 + pYA232 in χ3987 | Nov. 2, 1990 | 55116 |

EXAMPLES

EXAMPLE 1

This example describes the isolation of avirulent microbes by the introduction of deletion mutations affecting cAMP synthesis and utilization and the identification of strains with mutations conferring stability of phenotype, complete avirulence and high immunogenicity.

Bacterial strains. The *Escherichia coli* and *Salmonella typhimurium* strains used are listed in Table 1.A. and B. They were maintained as frozen cultures suspended in 1% Bacto-peptone containing 5% glycerol and fast-frozen in dry ice-ethanol for storage in duplicate at −70° C. and also suspended in 1% Bacto-peptone containing 50% glycerol for storage at −20° C. for routine use.

Media. Complex media for routine cultivation were n broth (Lennox, *Virology* 1:190–206, (1965)) and Luria broth (Luria and Burrous, *J. Bacteriol.* 74:461–476 (1957)). Difco agar was added to Luria broth at 1.2% for base agar and 0.65% for soft agar. Penassay agar was used for routine enumeration of bacteria. Fermentation was evaluated by supplementing MacConkey base agar or Eosin methylene blue agar (Curtiss, *Genetics* 58:9–54 (1968)) with 1% final concentration of an appropriate carbohydrate.

Synthetic media were minimal liquid (ML) and minimal agar (MA) supplemented with nutrients at optimal levels as previously described (Curtiss, *J. Bacteriol.* 89:28–40, (1965)). Buffered saline with gelatin (BSG) (Curtiss, 1965 supra) was used routinely as a diluent.

Transduction. Bacteriophage P22HTint was routinely used for transduction using standard methods (Davis et al., "A Man. for Genet. Eng.-Adv. Bacterial Genetics". Cold Spring Harbor Laboratory, Cold Spring Harbor, N.Y., (1979)). An overnight culture of the donor strain was diluted 1:20 into prewarmed Luria broth, grown for 60 minutes with shaking at 37° C. and then infected with P22HTint at a multiplicity of 0.01. The infection mixture was shaken overnight for approximately 15 h, chloroform added and allowed to shake an additional 10 min at 37° C., and the suspension centrifuged (Sorvall RC5C, SS-34 rotor, 7,000 rpm, 10 min) to remove bacterial debris. The supernatant fluid containing the phage (ca. $10^{10}$/ml) was stored at 4° C. over chloroform. Tetracycline to a concentration of 12.5 µg/ml was used to select for transduction of Tn10 insertions and Tn10-induced mutations.

Fusaric acid selection for loss of Tn10. The media and methods described by Maloy and Nunn (*J. Bacteriol.* 145:1110–1112, (1981)) were used. Strains with Tn10-induced mutations were grown overnight in L broth containing 12.5 mg tetracycline/ml at 37° C. to approximately $5 \times 10^8$ CFU/ml. Cultures were then diluted 1:40 into prewarmed L broth without tetracycline and aerated at 37° C. to a titer of about $2 \times 10^9$ CFU/ml. Suitable numbers of cells (i.e. $10^7$–$10^8$) diluted in BSG were plated on fusaric acid-containing medium and incubated 48 h at 37° C. Fusaric acid-resistant isolates were purified on the same selective medium. Single isolates were picked, grown and tested for tetracycline sensitivity on Penassay agar with and without 12.5 µg tetracycline/ml.

Mice. Female BALB/c mice (6 to 8 weeks old) (Sasco, Omaha, Nebr.) were used for infectivity and/or immunization experiments. Animals were held for one week in a quarantined room prior to being used in experiments. Experimental mice were placed in Nalgene filter-covered cages with wire floors. Food and water were given ad libitum. The animal room was maintained at 22°–23° C. with a period of 12 h illumination.

Animal infectivity. The virulence of *S. typhimurium* strains was determined following peroral (p.o.) or intraperitoneal (j.p.) inoculation. Bacteria for inoculation in mice were grown overnight as standing cultures at 37° C. in L broth. These cultures were diluted 1:50 into prewarmed L broth and aerated at 37° C. for approximately 4 h to an $OD_{600}$ of about 0.8–1.0. The cells were concentrated 50-fold by centrifugation in a GSA rotor at 7,000 rpm for 10 min at 4° C. in a Sorvall RC5C centrifuge followed by suspension in BSG. Suitable dilutions were plated on Penassay agar for titer determination and on MacConkey agar with 1% maltose to verify the Cya/Crp phenotype. For all p.o. inoculations with *S. typhimurium*, mice were deprived of food and water for 4 h prior to infection. They were then given 30 ml of 10% (w/v) sodium bicarbonate using a Piperman P200 10–15 min prior to p.o. feeding of 20 µl of *S. typhimurium* suspended in BSG using a Pipetman P20. Food and water were returned 30 min after oral inoculation. Morbidity and mortality of mice were observed over a 30-day period. Intraperitoneal inoculation of unfasted BALB/c mice was performed using a 26-gauge ⅜" needle to deliver 100 µl of *S. typhimurium* bacterial suspension diluted in BSG. Morbidity and mortality of mice were observed over a 30-day period.

Evaluation of protective immunity. In initial experiments, any mice that survived infection with any *S. typhimurium* mutant strain for 30 days were challenged on day 31 with $10^3$–$10^4$ times the $LD_{50}$ dose of the wild-type mouse-virulent *S. typhimurium* parent strain by the p.o. route.

Subsequently, groups of mice were perorally immunized with various doses of a virulent mutants and then challenged with various doses of virulent wild-type parent cells at various times after the initial immunization. Morbidity and mortality were observed throughout the experiment and for a least 30 days after challenge with the wild-type parent.

Isolation of *S. typhimurium* strains with Δcya-12 and Δcrp-11 mutations. The wild-type, mouse-passaged virulent *S. typhimurium* SL1344 strain χ3339 were genetically modified as described below, using classical genetic methods similar to those described in Curtiss and Kelly, 1987. The strategy consisted of transducing the original crp-773::Tn10 mutation from PP1037 and the original cya::Tn10 mutation from PP1002 into the highly virulent and invasive *S. typhimurium* SL1344 strain χ3339 and screening numerous independent fusaric acid resistant, tetracycline sensitive deletion mutants for complete avirulence and highest immunogenicity in mice, as well as for greatest genotypic stability.

Transduction of the Tn10 insertions in the crp and cya genes was facilitated by first making a high-titer bacteriophage P22HTint lysate on the *S. typhimurium* strain PP1037 containing the crp-773::Tn10 mutation and another lysate on the *S. typhimurium* strain PP1002 containing the cya::Tn10 mutation. The resulting P22HTint lysates were subsequently used to infect the recipient *S. typhimurium* χ3339 at a multiplicity of 0.3 to transduce it to tetracycline resistance with screening for a maltose-negative phenotype. The phage-bacteria infection mixtures were incubated for 20 min at 37° C. before 100 μl samples were spread onto MacConkey agar (Difco Laboratories, Detroit, Mich.) containing 1% maltose (final concentration) supplemented with 12.5 μg tetracycline/ml. After approximately 26 h incubation at 37° C., a tetracycline-resistant, maltose-negative colony resulting from the P22HTint (PP1037)→χ3339 infection and a tetracycline-resistant, maltose-negative colony resulting from the P22HTint (PP1002)→χ3339 infection were picked into 0.5 ml BSG and streaked onto the same selective media. The resulting χ3339 derivatives were designated χ3604 (cya::Tn10) and χ3605 (crp-773::Tn10) (Table 1.A.).

TABLE 1

Bacterial strains

| Strain number | Relevant genotype | Derivation |
|---|---|---|
| A. *E. coli* | | |
| CA8445 | pSD110 (crp⁺ Ap^r)/Δcrp-45 Δcya-06 | Schroeder and Dobrogosz, J. Bacteriol. 167:616–622 (1986). |
| χ6060 | F' traD36 proA⁺ proB⁺ lacI^q ΔlacZM15::Tn5/araD139 Δ(ara, leu)-7697 ΔlacX74 ΔphoA20 galE galK recA rpsE argE_am rpoB thi | Goldschmidt, Thoren-Gordon and Curtiss, J. Bacteriol. 172:3988–4001 (1990). |
| B. *S. typhimurium* | | |
| 798 | wild-type prototroph | Received from R. Wood, NADC, Ames, IA, as a swine isolate. |
| #30875 | wild-type prototroph | Received from P. McDonough, Cornell Univ. NY as a horse isolate. |
| DU8802 | zhc-1431::Tn10 | Sanderson and Roth, Microbiol. Rev. 42:485–532 (1988). |
| PP1002 | cya::Tn10 | Postma, Keizer and Koolwijk, J. Bacteriol. 168:1107–1111 (1986). |
| PP1037 | crp-773::Tn10 | Postma, Keizer and Koolwijk, supra. |
| SGSC452 | leu hsdLT galE trpD2 rpsL120 metE551 metA22 hsdSA hsdSB ilv | Sanderson and Roth, 1988 supra. |
| TT172 | cysG::Tn10 | Sanderson and Roth, 1986 supra. |
| TT2104 | zid-62::Tn10 | Sanderson and Roth, supra. |
| χ3000 | LT2-Z prototroph | Gulig and Curtiss, Infect. Immun. 55:2891–2901 (1987). |
| χ3140 | SR-11 wild-type prototroph | Gulig and Curtiss, 1987 supra. |
| χ3306 | SR-11 gyrA1816 | Gulig and Curtiss, 1987 supra. |
| χ3385 | LT-2 hsdL6 galE496 trpB2 flaA66 his-6165 rpsL120 xyl-404 metE551 metA22 lamB⁺ (*E. coli*) Δ[zja::Tn10] hsdSA29 val | Tinge and Curtiss, J. Bacteriol. 172: in press (1990). |
| χ3339 | SL1344 wild type hisG rpsL | Smith et al., Am. J. Vet. Res. 43:59–66 (1984). |
| χ3520 | ΔasdA1 zhf-4::Tn10 | ATCC53681; Asd⁻ tetracycline-resistant derivative of χ3000. |
| χ3604 | hisG rpsL cya::Tn10 | P22HTint(PP1002) → χ3339 with selection for tetracycline resistance (Mal⁻). |
| χ3605 | hisG rpsL crp-773::Tn10 | P22HTint(PP1037) → χ3339 with selection for tetracycline resistance (Mal⁻). |
| χ3615 | hisG rpsL Δcya-12 | Fusaric acid-resistant, tetracycline-sensitive Mal⁻ derivative of χ3604. |
| χ3622 | hisG rpsL Δ[crp-cysG]-10 | Fusaric acid-resistant, tetracycline-sensitive Mal⁻ Cys⁻ Arg⁻ derivative of χ3605. |
| χ3623 | hisG rpsL Δcrp-11 | Fusaric acid-resistant, tetracycline-sensitive Mal⁻ derivative of χ3605. |
| χ3670 | pSD110⁺ hsdL6 galE496 trpB2 | χ3385 transformed with pSD110 from CA8445 |

TABLE 1-continued

Bacterial strains

| Strain number | Relevant genotype | Derivation |
|---|---|---|
| | flaA66 his-6165 rpsL120 xyl-404 metE551 metA22 lamB+ (E. coli) Δ[zja::Tn10 hsdSA29 val | with selection for ampicillin resistance, Mal+. |
| χ3706 | pSD110+ hisG rpsL Δ[crp-cysG]-10 | χ3622 transformed with pSD110 from CA8445 with selection for ampicillin resistance, Mal+. |
| χ3711 | hisG rpsL Δcya-12 zid-62::Tn10 | P22HTint(χ3738) → χ3615 with selection for tetracycline resistance, Mal−. |
| χ3712 | hisG rpsL Δcrp-10 zhc-1431::Tn10 | P22HTint(χ3741) χ3622 with selection for tetracycline resistance, Mal−, (Cys−, Arg−). |
| χ3722 | pSD110+ hisG rpsL Δ[crp-cysG]-10 Δcya-12 zid-62::Tn10 | P22HTint(χ3711) χ3706 with selection for tetracycline resistance (Mal−). |
| χ3723 | pSD110+ hisG rpsL Δ[crp-cysG]-10 Δcya-12 Δ[zid-62::Tn10] | Fusaric acid-resistant, tetracycline-sensitive, ampicillin-resistant, Mal−, Cys−, Arg− derivative of χ3723. |
| χ3724 | hisG rpsL Δ[crp-cysG]-10 Δcya-12 Δ[zid-62::Tn10] | Ampicillin-sensitive derivative of χ3723; pSD110 cured by serial passage in L broth at 37° C. |
| χ3730 | leu hsdLT galE trpD2 rpsL120 ΔasdA1 Δ[zhf-4::Tn10] metE551 metA22 hsdSA hsdSB ilv | Asd− Tc* derivative of SGSC452. |
| χ3731 | pSD110+ hisG rpsL crp-773::Tn10 | Spleen isolate of χ3706 from BALB/c mouse. |
| χ3738 | zid-62::Tn10 | P22HTint(TT2104) → χ3000 with selection for tetracycline resistance. |
| χ3741 | zhc-1431::Tn10 | P22HTint(DU8802) → χ3000 with selection for tetracycline resistance. |
| χ3761 | UK-1 wild-type prototroph | ATCC68169; Spleen isolate of #30875 from White leghorn chick. |
| χ3773 | hisG rpsL Δcrp-11 zhc-1431::Tn10 | P22HTint(λ3741) → χ3623 with selection for tetracycline resistance (Mal−). |
| χ3774 | pSD110+ hisG rpsL Δcrp-11 | χ3623 transformed with pSD110 from CA8445 with selection for ampicillin resistance, Mal+. |
| χ3777 | Δ[crp-cysG]-10 zhc-1431::Tn10 | P22HTint(λ3712) 798 with selection for tetracycline resistance, Mal−, (Cys−, Arg−). |
| λ3779 | Δ[crp-cysG]-10 Δ[zhc-1431::Tn10] | P22HTint(λ3712) #30875 with selection for tetracycline resistance, Mal−, (Cys−, Arg−). |
| χ3784 | Δ[crp-cysG]-10 Δ[zhc-1431::Tn10] | Fusaric acid-resistant, tetracycline-sensitive, Mal−, Cys−, Arg− derivative of λ3779. |
| χ3806 | Δ[crp-cysG]-10 Δ[zhc-1431::Tn10] | Fusaric acid-resistant, tetracycline-sensitive, ampicillin-resistant, Mal−, Cys−, Arg− derivative of χ3777. |
| χ3825 | Δcrp-11 zhc-1431::Tn10 | P22HTint(λ3773) 798 with selection for tetracycline resistance, Mal−. |
| χ3828 | Δcrp-11 zhc-1431::Tn10 | P22HTint(χ3773) UK-1 with selection for tetracycline resistance, Mal−. |
| χ3876 | Δcrp-11 Δ[zhc-1431::Tn10] | Fusaric acid-resistant, tetracycline-sensitive, Mal− derivative of χ3825. |
| χ3901 | pSD110+ Δ[crp-cysG]-10 Δ[zhc-1431::Tn10] | P22HTint(χ3670) χ3806 with selection for ampicillin resistance, Mal+, (Cys−, Arg−). |
| χ3902 | pSD110+ Δ[crp-cysG]-10 Δ[zhc-1431::Tn10] Δcya-12 zid-62::Tn10 | P22HTint(χ3711) χ3901 with selection for tetracycline resistance, Mal−, (Cys−, Arg−). |
| χ3910 | hisG rpsL cysG::Tn10 | P22HTint(TT172) λ3339 with selection for tetracycline resistance, Cys−. |
| λ3931 | hisG rpsL Δ[crp-cysG]-14 | Fusaric acid-resistant, tetracycline-sensitive, Mal−, Cys−, (Arg+) derivative of λ3910. |
| χ3936 | hisG rpsL Δcrp-11 Δcya-12 zid-62::Tn10 | P22HTint(χ3711) χ3774 with selection for tetracycline resistance, Mal−. |
| χ3937 | hisG rpsL Δcrp-11 Δcya-12 zid-62::Tn10 | Fusaric acid-resistant, tetracycline sensitive, Mal− derivative of χ3936. |
| χ3938 | pSD110+ Δcrp-11 Δ[zhc-1431::Tn10] | P22HTint(χ3670) χ3876 with selection for ampicillin resistance, Mal+. |
| χ3939 | hisG rpsL Δcrp-11 Δcya-12 Δ[zid-62::Tn10] | Ampicillin-sensitive derivative of χ3937; pSD110 cured by serial passage in L broth at 37° C. |
| χ3945 | pSD110+ Δ[crp-cysG]-10 Δ[zhc-1431::Tn10] | P22HTint(λ3670) χ3784 with selection for ampicillin resistance, Mal+. |
| χ3954 | Δcrp-11 Δ[zhc-1431::Tn10] | Fusaric acid-resistant, tetracycline-sensitive, Mal− derivative of χ3828. |
| χ3955 | hisG rpsL Δ[crp-cysG]-14 | P22HTint(χ3670) χ3931 with selection for |

TABLE 1-continued

Bacterial strains

| Strain number | Relevant genotype | Derivation |
|---|---|---|
| | | ampicillin resistance, Mal$^+$, (Cys$^-$, Arg$^+$). |
| χ3956 | pSD110$^+$ Δ[crp-cysG]-10 Δ[zhc-1431::Tn10] Δcys-12 zid-61::Tn10 | P22HTint(λ3711) χ3945 with selection for tetracycline resistance, Mal$^-$, Cys$^-$, Arg$^-$. |
| χ3957 | pSD110$^+$ Δ[crp-cysG]-10 Δ[zhc-1431::Tn10] Δcya-12 Δ[zid-61::Tn10] | Fusaric acid-resistant, tetracycline-sensitive, Mal$^-$, Cys$^-$, Arg$^-$ derivative of χ3956. |
| χ3958 | Δ[crp-cysG]-10 Δ[zhc-1431::Tn10] Δcya-12 Δ[zid-61::Tn10] | Ampicillin-sensitive derivative of χ3957; pSD110 cured by serial passage in L broth at 37° C. |
| χ3961 | pSD110$^+$ Δcrp-11 Δ[zhc-1431::Tn10] | P22HTint(χ3670) χ3954 with selection for ampicillin resistance, Mal$^+$. |
| χ3962 | pSD110$^+$ Δcrp-11 Δ[zhc-1431::Tn10] Δcya-12 zid-62::Tn10 | P22HTint(χ3711) χ3961 with selection for tetracycline resistance, Mal$^-$. |
| χ3978 | pSD110$^+$ Δcrp-11 Δ[zhc-1431::Tn10] Δcya-12 zid-62::Tn10 | P22HTint(χ3711) χ3938 with selection for tetracycline resistance, Mal$^-$. |
| χ3985 | Δcya-12 Δ[zid-62::Tn10] Δcrp-11 Δ[zhc-1431::Tn10] | ATCC68166; Fusaric acid-resistant, tetracycline-sensitive, Mal$^-$ derivative of χ3962 cured of pSD110. |
| χ4038 | Δcya-12 Δ[zid-62::Tn10] Δ[crp-cysG]-10 Δ[zhc-1431::Tn10] | Fusaric acid-resistant tetracycline-sensitive Mal$^-$, Cys$^-$, Arg$^-$ derivative of χ3902 cured of pSD110. |
| χ4039 | Δcya-12 Δ[zid-62::Tn10] Δ[crp-cysG]-10 Δ[zhc-1431::Tn10] | Fusaric acid-resistant, tetracycline-sensitive Mal$^-$ derivative of χ3978 cured of pSD110. |
| χ4063 | SR-11 arg::Tn10 | P22HTint(Tn10 library) χ3306 with selection for tetracycline resistance, Arg$^-$. |
| χ4071 | SR-11 arg::Tn10 | P22HTint(Tn10 library) χ3306 with selection for tetracycline resistance, Arg$^-$. |
| χ4246 | Δ[crp-cysG]-10 zhc-1431::Tn10 | P22HTint(χ3712) 798 with selection for tetracycline resistance, Mal$^-$, (Cys$^-$ Arg$^-$). |
| χ4247 | pSD110$^+$ Δ[crp-cysG]-10 zhc-1431::Tn10 | P22HTint(λ3670) χ4246 with selection for ampicillin resistance, Mal$^+$, (Cys$^-$ Arg$^-$). |
| χ4248 | Δ[crp-cysG]-10 zhc-1431::Tn10 | P22HTint(λ3712) ATCC68169 (UK-1) with selection for tetracycline resistance, Mal$^-$, (Cys$^-$ Arg$^-$). |
| χ4262 | pSD110$^+$ Δ[crp-cysG]-10 zhc-1431::Tn10 | P22HTint(χ3670) χ4248 with selection for ampicillin resistance, Mal$^+$, (Cys$^-$ Arg$^-$). |
| C. S. typhi | | |
| Ty2 | Type E1 Cys$^-$ Trp$^-$ wild type | Louis Baron, Walter Reed Army Institute of Research. |
| ISP1820 | Type 46 Cys$^-$ Trp$^-$ wild type | Center for Vaccine Development, Baltimore, MD; 1983 isolate from Chilean patient. |
| ISP2822 | Type E1 Cys$^-$ Trp$^-$ wild type | Center for Vaccine Development, Baltimore, MD; 1983 isolate from Chilean patient. |
| χ3791 | Δ[crp-cysG]-10 zhc-1431::Tn10 | P22HTint(λ3712) ISP2822 with selection for tetracycline resistance (Mal$^-$, Cys$^-$, Arg$^-$, Vi$^+$). |
| χ3792 | Δ[crp-cysG]-10 zhc-1431::Tn10 | P22HTint(λ3712) Ty2 with selection for tetracycline resistance (Mal$^-$, Cys$^-$, Arg$^-$ Vi$^+$). |
| χ3802 | Δ[crp-cysG]-10 Δ[zhc-1431::Tn10] | Fusaric acid-resistant, tetracycline-sensitive Mal$^-$ derivative of χ3791 (Vi$^+$). |
| χ3803 | Δ[crp-cysG]-10 Δ[zhc-1431::Tn10] | Fusaric acid-resistant, tetracycline-sensitive Mal$^-$ derivative of χ3792 (Vi$^+$). |
| χ3824 | pSD110$^+$ Δ[crp-cysG]-10 Δ[zhc-1431::Tn10] | χ3803 electro-transformed with pSD110 from χ3670 with selection for ampicillin resistance (Mal$^+$, Cys$^-$, Arg$^-$, Vi$^+$). |
| χ3845 | pSD110$^+$ Δ[crp-cysG]-10 Δ[zhc-1431::Tn10] | χ3802 electro-transformed with pSD110 from χ3670 with selection for ampicillin resistance (Mal$^+$, Cys$^-$, Arg$^-$, Vi$^+$). |
| χ3852 | Δcrp-11 zhc-1431::Tn10 | P22HTint(Δ3773) ISP2822 with selection for tetracycline resistance (Mal$^-$, Vi+). |
| χ3853 | Δcrp-11 zhc-1431::Tn10 | P22HTint(χ3773) Ty2 with selection for tetracycline resistance (Mal$^-$, Vi$^+$). |
| χ3877 | Δcrp-11 Δ[zhc-1431::Tn10] | Fusaric acid-resistant, tetracycline-sensitive Mal$^-$ derivative of χ3852 (Vi$^+$). |
| χ3878 | Δcrp-11 Δ[zhc-1431::Tn10] | Fusaric acid-resistant, tetracycline-sensitive Mal$^-$ derivative of χ3853 (Vi$^+$). |
| χ3879 | pSD110$^+$ Δcrp-11 Δ[zhc-1431::Tn10] | P22HTint(χ3670) Δ3877 with selection for ampicillin resistance (Mal$^+$, Vi$^+$). |
| χ3880 | pSD110$^+$ Δcrp-11 Δ[zhc-1431::Tn10] | P22HTint(χ3670) χ3878 with selection for ampicillin resistance (Mal$^+$, Vi$^+$). |

TABLE 1-continued

Bacterial strains

| Strain number | Relevant genotype | Derivation |
|---|---|---|
| χ3919 | pSD110+ Δ[crp-cysG]-10 Δ[zhc-1431::Tn10] Δcya-12 zid-62::Tn10 | P22HTint(χ3711) χ3824 with selection for tetracycline resistance (Mal−, Vi+). |
| χ3920 | pSD110+ Δ[crp-cysG]-10 Δ[zhc-1431::Tn10] Δcya-12 zid-62::Tn10 | P22HTint(χ3711) χ3845 with selection for tetracycline resistance (Mal−, Vi+). |
| χ3921 | pSD110+ Δcrp-11 Δ[zhc-1431::Tn10] Δcya-12 zid-62::Tn10 | P22HTint(χ3711) χ3879 with selection for tetracycline resistance (Mal−, Vi+). |
| χ3922 | pSD110+ Δcrp-11 Δ[zhc-1431::Tn10] Δcya-12 zid-62::Tn10 | P22HTint(χ3711) χ3880 with selection for tetracycline resistance (Mal−, Vi+). |
| χ3924 | Δ[crp-cysG]-10 Δ[zhc-1431::Tn10] Δcya-12 Δ[zid-62::Tn10] | Fusaric acid-resistant, tetracycline-sensitive Mal− derivative of χ3919 cured of pSD110 (Vi+). |
| χ3925 | Δ[crp-cysG]-10 Δ[zhc-1431::Tn10] Δcya-12 Δ[zid-62::Tn10] | Fusaric acid-resistant, tetracycline-sensitive Mal− derivative of χ3920 cured of pSD110 (Vi+). |
| χ3926 | Δcrp-11 Δ[zhc-1431::Tn10] Δcya-12 Δ[zid-62::Tn10] | Fusaric acid-resistant, tetracycline-sensitive Mal− derivative of χ3921 cured of pSD110 (Vi+). |
| χ3927 | Δcrp-11 Δ[zhc-1431::Tn10] Δcya-12 Δ[zid-62::Tn10] | Fusaric acid-resistant, tetracycline-sensitive Mal− derivative of χ3922 cured of pSD110 (Vi+). |
| χ3940 | Δ[crp-cysG]-10 Δ[zhc-1431::Tn10] Δcya-12 Δ[zid-62::Tn10] | Flagella-positive, motile derivative of χ3925 (Vi+). |
| χ4073 | Δ[crp-cysG]-10 Δ[zhc-1431::Tn10] Δcya-12 Δ[zid-62::Tn10] | Flagella-positive, motile derivative of χ3924 (Vi+). |
| χ4296 | Δcrp-11 Δ[zhc-1431::Tn10] Δcya-12 Δ[zid-62::Tn10] ΔasdA1 zhf-4::Tn10 | P22HTint(χ3520) χ3927 with selection for tetracycline resistance and screening for Asd−, Mal−, Vi+. |
| χ4297 | Δcrp-11 Δ[zhc-1431::Tn10] Δcya-12 Δ[zid-62::Tn10] ΔasdA1 Δ[zhf-4::Tn10] | Fusaric acid-resistant, tetracycline-sensitive Asd−, Mal− derivative of χ4296 (Vi+). |
| χ4298 | Δcrp-11 zhc-1431::Tn10 | P22HTint(λ3773) ISP1820 with selection for tetracycline resistance (Mal−, Vi+). |
| χ4299 | Δcrp-11 Δ[zhc-1431::Tn10] | Fusaric acid-resistant, tetracycline-sensitive Mal− derivative of χ4298 (Vi+). |
| χ4300 | pSD110+ Δcrp-11 Δ[zhc-1431::Tn10] | P22HTint(χ3670) Δ4299 with selection for ampicillin resistance (Mal+, Vi+). |
| χ4316 | pSD110+ Δcrp-11 Δ[zhc-1431::Tn10] Δcya-12 zid-62::Tn10 | P22HTint(χ3670) χ4300 with selection for tetracycline resistance (Mal−, Vi+). |
| χ4322 | Δcrp-11 Δ[zhc-1431::Tn10] Δcya-12 Δ[zid-62::Tn10] | Fusaric acid-resistant, tetracycline-sensitive Mal− derivative of χ4316 cured of pSD110 (Vi+). |
| χ4323 | Δcrp-11 Δ[zhc-1431::Tn10] Δcya-12 Δ[zid-62::Tn10] | Flagella-positive, motile derivative of χ4322 (Vi+) |
| χ4324 | Δ[crp-cysG]-10 zhc-1431::Tn10 | P22HTint(χ3712) ISP1820 with selection for tetracycline resistance (Mal−, Cys−, Arg−, Vi+). |
| χ4325 | Δ[crp-cysG]-10 Δ[zhc-1431::Tn10 | Fusaric acid-resistant, tetracycline-sensitive Mal− derivative of χ4324 (Vi+). |
| χ4331 | pSD110+ Δ[crp-cysG]-10 Δ[zhc-1431::Tn10] | P22HTint(χ3670) χ4325 with selection for ampicillin resistance (Mal+, Vi+). |
| χ4340 | pSD110+ Δ[crp-cysG]-10 Δ[zhc-1431::Tn10] Δcya-12 zid-62::Tn10 | P22HTint(χ3711) χ4331 with selection for tetracycline resistance (Mal−, Vi+). |
| χ4345 | Δ[crp-cysG]-10 Δ[zhc-1431::Tn10] Δcya-12 Δ[zid-62::Tn10] | Fusaric acid-resistant, tetracycline-sensitive Mal− derivative of χ4340 cured of pSD110 (Vi+). |
| χ4346 | Δ[crp-cysG]-10 Δ[zhc-1431::Tn10] Δcya-12 Δ[zid-62::Tn10] | Flagella-positive, motile derivative of χ4345 (Vi+). |

Strains χ3604 and χ3605 were grown in L broth+12.5 μg tetracycline/ml and 100 μl samples of each strain diluted 1:10 into buffered saline with gelatin (BSG) were spread onto 10 plates of fusaric acid-containing (FA) media (Maloy and Nunn, 1981). The plates were incubated approximately 36 h at 37° C. Five fusaric acid-resistant colonies from each plate were picked into 0.5 ml BSG and purified on FA media. Purified fusaric acid-resistant colonies were picked into L broth and grown at 37° C. to turbidity and checked for loss of Tn10 (tetracycline sensitivity). One tetracycline-sensitive derivative was selected from each of the ten platings on FA media and characterized for complete LPS (by P22HTint sensitivity), auxotrophy or prototrophy, stability of the gene deletion, and reversion to tetracycline resistance. This procedure resulted in ten independently isolated Δcya mutants from χ3604 and ten independently isolated Δcrp mutants from χ3605.

Genetic stability of avirulent mutants. Strains to be orally administered as live vaccines must have complete stability with regard to both their avirulence and their immunogenic attributes. When 50-fold concentrated cultures and various dilutions (~$10^9$, $10^7$, $10^5$, $10_3$ CFU/plate) of each of the ten independent Δcya mutants and each of the ten independent and further analysis of the properties of the Δcrp-10 mutation are given in Example 3.

TABLE 2

Phenotypic characteristics of *S. typhimurium* Δcya and Δcrp strains

| Strain and genotype | P22[a] | Carbohydrate fermentation and use[b] | | | | | | | | Auxotrophy | | |
|---|---|---|---|---|---|---|---|---|---|---|---|---|
| | | Mal | Mtl | Ino | Srl | Rha | Mel | Gal | Glc | His | Arg | Cys |
| χ3339 wild type | S | + | + | + | + | + | + | + | + | − | + | + |
| χ3615 Δcya-12 | S | − | − | − | − | − | − | +/− | + | − | + | + |
| χ3622 Δcrp-10 | S | − | − | − | − | − | − | +/− | + | − | − | − |
| χ3623 Δcrp-11 | S | − | − | − | − | − | − | +/− | + | − | + | + |

[a]Bacteriophage P22HTint S = Sensitive; R = Resistant
[b]Fermentation on MacConkey Base agar media and API 20E and growth on MA + 0.5% of carbon source.

Δcrp mutants were plated on minimal agar media (supplemented with 22 μg cysteine/ml and 22 μg arginine/ml) containing 0.5% maltose, melibiose, xylose, glycerol, or rhamnose that should not support their growth, revertants and mutants were not detected. One set of duplicate plates were UV-irradiated (5 joules/meter$^2$/sec) and incubated at 37° C. in the dark. The other set of plates was incubated at 37° C. with illumination. Revertants and mutants were not detected after a 48 h growth period. An investigation was also conducted as to whether tetracycline-resistant revertants/mutants could be recovered from the fusaric acid resistant Δcya and Δcrp mutants at frequencies higher than could be observed for the tetracycline-sensitive wild-type parental strain. In all cases, such tetracycline-resistant revertants/mutants were not observed.

Virulence and immunogenicity of Δcrp and Δcya mutants. The resulting ten Δcrp and ten Δcya mutants were screened in BALB/c mice by peroral inoculation to determine the lowest virulence and disease symptomology as revealed by the appearance of the coat (scruffy versus smooth), appetite, and activity (high or low). Five mice per group were p.o. inoculated with ~$10^9$ CFU of each of the independent cya or crp deletion mutants. Animals were scored based on the above criteria and on day 30 of the experiment the survivors were challenged with $10^8$ CFU of the wild-type virulent parent strain χ3339. In three of the twenty groups infected with the cya or crp deletion mutants, five of five mice survived the initial infection with the Δcya-12, Δcrp11 and Δcrp-10 mutants and were also completely protected against $10^4$ LD$_{50}$s of the wild-type challenge. One group in particular, the Δcrp-10 mutant, was unequalled in avirulence, immunogenicity and stability. After repeating these experiments, mice never appeared affected by any dose given p.o. or j.p. of the Δcrpr10 mutant (see Example 3, Table 6).

Properties of selected mutant strains. χ3615, χ3622 and χ3623 with the Δcya-12, Δcrp-10 and Δcrp-11 mutations, respectively, were judged to be least virulent, highly immunogenic and extremely stable phenotypically and genotypically. Data on the phenotypic properties of these strains is given in Table 2. Table 3 presents data on the avirulence and immunogenicity of these strains in comparison to results with the virulent wild-type parent χ3339 and strains χ3604 and χ3605 with the cya::Tn10 and crp-773::Tn10 mutations, respectively. In addition to requiring histidine, which is due to the hisG mutation in the parental χ3339, the Δcrp-10 mutation imposed on χ3622 requirements for the amino acids arginine and cysteine. The bases for this observation

TABLE 3

Virulence and immunogenicity of *S. typhimurium* cya::Tn10, crp::Tn10 Δcya-12, Δcrp-10 and Δcrp-11 mutants in BALB/c mice

| | | P.O. immunization | | Wild-type P.O. challenge | |
|---|---|---|---|---|---|
| Strain number | Relevant genotype | Dose (CFU) | Survival live/total | Dose (CFU) | Survival live/total |
| χ3339 | wild type | — | — | $6.0 \times 10^4$ | 2/5 |
| χ3604 | cya::Tn10 | $6.2 \times 10^8$ | 5/5 | $8.8 \times 10^8$ | 4/5 |
| χ3605 | crp-773::Tn10 | $6.8 \times 10^8$ | 5/5 | $8.8 \times 10^8$ | 5/5 |
| χ3615 | Δcya-12 | $2.2 \times 10^9$ | 5/5 | $3.2 \times 10^8$ | 5/5 |
| χ3622 | Δcrp-10 | $1.5 \times 10^9$ | 5/5 | $3.2 \times 10^8$ | 5/5 |
| χ3623 | Δcrp-11 | $4.6 \times 10^8$ | 5/5 | $8.8 \times 10^8$ | 5/5 |

EXAMPLE 2

This example describes the construction of avirulent microbes by the introduction of deletion mutations affecting cAMP synthesis and utilization and the characterization of strains with two deletion mutations for stability of phenotype, complete avirulence and high immunogenicity.

Bacterial strains. The *Escherichia coli* and *Salmonella typhimurium* strains used are listed in Table 1.A. and B. The maintenance and storage of these strains are as described in Example 1.

Media. Complex media for routine cultivation, enumeration and identification of bacteria are as described in Example 1.

Transduction and fusaric acid selection for loss of Tn10. The media and methods are as described in Example 1.

Animal infectivity and evaluation of protective immunity. The virulence and immunogenicity of *S. typhimurium* strains were determined as described in Example 1.

Construction of *S. typhimurium* strains with Δcya-12. and Δcrp-11 deletion mutations. The best vaccine strains in terms of efficacy are likely to result from the attenuation of highly virulent strains that display significant colonizing ability and invasiveness. The criteria for selection of these highly pathogenic *S. typhimurium* wild-type strains such as SL1344 (χ3339), UK-1 (χ3761) and 798 included low LD$_{50}$ values (see Table 4) in mouse virulence assays, antibiotic sensitivity, possession of the virulence plasmid, ease of genetic manipulation (bacteriophage P22HTint or P1 sensitivity, transformability and ease of receiving mobilized plasmids), and colicin sensitivity.

The wild-type, virulent *S. typhimurium* strains SL1344 (χ3339), 798 and UK-1 (χ3761) were genetically modified as described below, using classical genetic methods similar to those described in Curtiss and Kelly, 1987. The strategy consists of mobilizing deletions of crp and cya genes that have been isolated and characterized in *S. typhimurium* SL1344 (as described in Example 1) by placing the transposon Tn10 (encoding tetracycline resistance) nearby the Δcya-12 or Δcrp-11 mutation and transducing the linked traits into the highly virulent *S. typhimurium* strains UK-1 χ3761, 798 and SL1344 χ3339 via P22HTint-mediated transduction with selection for tetracycline resistance and screening for a maltose-negative phenotype. The zhc-1431::Tn10 linked to Δcrp-11 and zid-62::Tn10 linked to Δcya-12 were used for this purpose. Neither insertion alone affects the virulence of *S. typhimurium*.

Transduction of the gene deletions with the linked transposon was facilitated by first making a high-titer bacteriophage P22HTint lysate on the *S. typhimurium* strain χ3773 containing the Δcrp-11 and zhc-1431::Tn10 mutations and another lysate on the *S. typhimurium* strain χ3711 containing the Δcya-12 and zid-62::Tn10 mutations. The resulting P22HTint lysates were then used to transduce the genetic traits into the wild-type recipient strains χ3339, 798 and χ3761.

P22HTint propagated on *S. typhimurium* χ3773 (Δcrp-11 zhc-1431::Tn10) was used to transduce the virulent strains to tetracycline resistance with screening for Mal⁻. The phage-bacteria infection mixtures were incubated for 20 min at 37° C. before 100 μl samples were spread onto MacConkey agar (Difco Laboratories, Detroit, Mich.) containing 1% maltose (final concentration) supplemented with 12.5 μg tetracycline/ml. After approximately 26 h incubation at 37° C., tetracycline restant Mal⁻ transductants were picked and purified onto the same medium. The resulting 798 derivative was designated χ3825 and the UK-1 derivative was designated χ3828. Strains χ3773, χ3825 and χ3828 have the genotype Δcrp-11 zhc-1431::Tn10 (Table 1.B.). These strains were grown in L broth+12.5 μg tetracycline/ml and each were diluted 1:10 into buffered saline with gelatin (BSG), 100 μl of each were spread onto fusaric acid-containing (FA) media (Maloy and Nunn, 1981) and the plates were incubated approximately 36 h at 37° C. Fusaric acid-resistant colonies of each strain were picked into 0.5 ml BSG and purified onto FA media. Purified fusaric acid-resistant colonies were picked into L broth and grown at 37° C. to turbidity and checked for loss of Tn10 (tetracycline sensitivity), presence of complete LPS and auxotrophy. The new strains were designated χ3876 (798) and χ3954 (UK-1) which both have the genotype Δcrp.-11 Δ[zhc-1431::Tn10] and χ3623 (SL1344 Δcrp-11 was originally isolated as described in Example 1) (Table 1.B.).

Since the phenotype of Cya⁻ and Crp⁻ mutants are the same (Mal⁻, Stl⁻, Mtl⁻, etc.), the plasmid, pSD110, carrying the cloned crp⁺ gene and conferring ampicillin resistance (Schroeder and Dobrogosz, *J. Bacteriol* 167:616–622 (1986)), was used to temporarily complement the Δcrp mutation in the chromosome enabling the identification of the Δcya mutation when introduced via transduction. L broth grown cultures of χ3623, χ3876 and χ3954 were transduced with P22HTint propagated on *S. typhimurium* χ3670, which contains the plasmid pSD110 (Table 1.B.). Selection was made on MacConkey agar+1% maltose+100 μg ampicillin/ml. After 26 h, an ampicillin-resistant, Mal⁺ colony of each strain was picked and purified on MacConkey agar +1% maltose agar+100 μg ampicillin/ml and designated χ3938 (798) and χ3961 (UK-1) which both have the genotype Δcrp-11 Δ[zhc-1431::Tn10] pSD110⁺ and χ3774 (SL1344) which has the genotype Δcrpr-11 pSD110⁺.

Strains χ3774, χ3938 and χ3961 were grown in L broth+100 μg ampicillin/ml and were each independently transduced with P22HTint propagated on χ3711 to introduce the linked Δcya-12 and zid-62::Tn10 mutations. The transduction mixtures were plated on MacConkey agar+1% maltose+100 μg ampicillin/ml+12.5 μg tetracycline/ml. Ampicillin-resistant (pSD110⁺), tetracycline-resistant (zid-62::Tn10), Mal⁻ (Δcya) colonies were picked and purified on MacConkey agar+1% maltose+100 μg ampicillin/ml+12.5 μg tetracycline/ml. Purified colonies were picked into L broth, grown to turbidity and the strains checked for complete LPS and auxotrophy. The resulting strains were designated χ3978 (798) and χ3962 (UK-1) which both have the genotype Δcrp-11 Δ[zhc-1431::Tn10] pSD110⁺ Δcya-12 zid-62::Tn10 and χ3936 (SL1344) which has the genotype Δcrprll pSD110⁺ Δcya-12 zid-62::Tn10. Cultures of χ3936, χ3978 and χ3962 were grown in L broth+100 μg ampicillin/ml+12.5 μg tetracycline/ml to turbidity, diluted 1:10 into BSG, and 100 μl samples of each culture spread onto fusaric acid-containing media and incubated approximately 36 h at 37° C. Fusaric acid-resistant colonies of each strain were picked and purified onto FA medium. Purified FA-resistant colonies were picked into L broth, grown to turbidity and then checked for loss of Tn10. (tetracycline sensitivity), complete LPS and auxotrophy. The pSD110 plasmid was usually lost spontaneously from the strains during this process to result in ampicillin sensitivity, except for the SL1344 derivative which involved two steps to eliminate pSD110. The final strains were designated χ4039 (798) and χ3985 (UK-1) which both have the genotype Δcrp-11 Δ[zhc-1431::Tn10] Δcya-12 Δ[zid-62::Tn10] and χ3939 (SL1344) which has the genotype Δcrp-11 Δcya-12 Δ[zid-62::Tn10] (Table 1.B.).

Genotypic and phenotypic stability of avirulent mutants. Methods for determining stability of genetic traits are as described in Example 1. All genotypic and phenotypic traits due to the Δcya Δcrp mutations were completely stable except motility. Although synthesis of functional flagella and display of motility is dependent on wild-type cya and crp gene functions, a suppressor mutation in the cfs (constitutive flagellar synthesis) gene can easily be selected to cause flagella synthesis and motility to be independent of cya and crp gene functions. In *S. typhimurium* Δcya Δcrp strains, motile variants were readily selected during the strain construction process. Since immunity to flagellar antigens may be protective, motile variants of all vaccine strains were selected.

*S. typhimurium* group B O-antigen synthesis was confirmed by slide agglutination with antisera (Difco Laboratories, Detroit, Mich.) and by P22HTint bacteriophage sensitivity by the Luria soft agar overlay technique.

Fermentation of sugars and growth on various carbon sources of the double mutant strains were identical to strains with only Δcya or Δcrp as listed in Table 2. The phenotypes were as expected based on published reports of the requirement for cyclic AMP and the cyclic AMP receptor protein for catabolic activities.

At each step in the construction following selection of a fusaric acid-resistant tetracycline-sensitive derivative, an investigation as to whether tetracycline-resistant revertants/mutants could be recovered at frequencies higher than could be observed for the parental tetracycline-sensitive wild-type strain was conducted. In all cases, such tetracycline-resistant revertants/mutants were not observed.

Virulence of Mutant Strains for Mice. Preliminary information on virulence of S. typhimurium mutant strains was obtained by infecting individual mice with $10^8$ mutant cells perorally and recording morbidity and mortality. Table 4 presents data on morbidity and mortality of mice infected perorally with the S. typhimurium wild-type parent strains, and the Δcya-12 Δcrp-11 derivatives χ3985 and χ4039.

Animal infectivity and evaluation of protective immunity. The virulence and immunogenicity of S. typhimurium strains were determined as described in Example 1.

Isolation of S. typhimurium strain with the Δcrp-10 mutation. As described in Example 1, one of ten Δcrp mutations isolated in χ3605 conferred auxotrophy for arginine (due to deletion of argD) and cysteine (due to deletion of cysG). The

TABLE 4

Virulence of S. typhimurium Δcya-12, Δcrp-11, Δcya-12, and Δcrp-11 Strains
After Inoculation of BALB/c Mice with S. typhimurium Δcya-12 and/or Δcrp-11 Strains

| Strain Number | Relevant Genotype | Route of Inoculation | Inoculating Dose (CFU) | Survival live/Total | Health[a] | Approx. wild-type $LD_{50}$ | Wild-type Origin |
|---|---|---|---|---|---|---|---|
| S. typhimurium | | | | | | | |
| χ3615 | Δcya-12 | PO | $2 \times 10^9$ | 5/5 | healthy | $6 \times 10^4$ | mouse |
| χ3623 | Δcrp-11 | PO | $5 \times 10^8$ | 5/5 | healthy | $6 \times 10^4$ | mouse |
| χ3985 | Δcya-12 Δcrp-11 | PO | $2 \times 10^9$ | 8/10 | moderate | $1 \times 10^5$ | horse |
| χ4039 | Δcya-12 Δcrp-11 | PO | $1 \times 10^9$ | 10/10 | healthy | $1 \times 10^5$ | pig |
| S. typhi | | | | | | | |
| χ3926 | Δcya-12 Δcrp-11 | IP[b] | $2 \times 10^3$ | 4/6 | healthy | ~29 | human |
| χ3927 | Δcya-12 Δcrp-11 | IP | $3 \times 10^3$ | 2/4 | healthy | <20 | human |

[a]Healthy-no noticeable signs of disease; moderate-moderately ill; ill-noticeably ill.
[b]IP-cells delivered in 0.5 ml 5% hog gastric mucin.

Effectiveness of immunization with avirulent mutants. Table 5 presents data on the ability of the S. typhimurium Δcya Δcyp mutants χ3985 and χ4039 to induce immunity to subsequent peroral challenge with $10^4$ times the $LD_{50}$ doses of fully virulent wild-type S. typhimurium cells. Under these high-dose challenges, many of the mice displayed moderate illness with decreased food consumption except mice immunized with χ4039 which remained healthy and ate and grew normally.

TABLE 5

Effectiveness of Immunization with Avirulent S. typhimurium
Δcya-12 and/or Δcrp-11 Mutants in Protecting Against
Challenge with Wild-type Virulent Parent Strains

| Strain Number | Relevant Genotype | Dose (CFU) of Immunizing Strain | Dose (CFU) of Wild-type Challenge Strain | Survival live/total |
|---|---|---|---|---|
| χ3615 | Δcya-12 | $2 \times 10^9$ | $3 \times 10^8$ | 5/5 |
| χ3623 | Δcrp-11 | $5 \times 10^8$ | $3 \times 10^8$ | 5/5 |
| χ3985 | Δcya-12 Δcrp-11 | $2 \times 10^9$ | $7 \times 10^8$ | 8/8 |
| χ4039 | Δcya-12 Δcrp-11 | $1 \times 10^9$ | $6 \times 10^8$ | 10/10 |

EXAMPLE 3

This Example demonstrates the isolation of an avirulent microbe that possesses a deletion mutation encompassing the crp gene and an adjacent gene which also governs virulence of Salmonella.

Bacterial strains. The Escherichia coli and Salmonella typhimurium strains used are listed in Table 1A and B. The maintenance and storage of these strains are as described in Example 1.

Media. Complex media for routine cultivation, enumeration and identification of bacteria are as described in Example 1.

Transduction and fusaric acid selection for loss of Tn10. The media and methods are as described in Example 1.

mutation in the S. typhimurium SL1344 strain χ3622 was originally referred to as Δcrp-10 but is now designated Δ[crp-cysG]-10 because of the auxotrophy for cysteine. A group of five BALB/c mice orally infected with $10^9$ χ3622 cells remained healthy and was totally unaffected (Table 3). Furthermore, these mice gained high-level immunity to oral challenge with $10^8$ parental χ3339 cells (Table 3).

A series of strains was constructed to independently evaluate each of the phenotypic characteristics of χ3622. The plasmid, pSD110, carrying the cloned crp$^+$ gene and conferring ampicillin resistance (Schroder and Dobrogosz, J. Bacteriol. 167:616–622 (1986)), was used to complement the Δcrp mutation in the chromosome. An L broth culture of χ3622 was transduced with P22HTint propagated on S. typhimurium χ3670, which contains the plasmid pSD110. Selection was made on MacConkey agar+1% maltose+100 μg ampicillin/ml. After 26 h, an ampicillin-resistant, Mal$^+$ colony was picked and purified on MacConkey agar+1% maltose agar+100 μg ampicillin/ml and designated χ3706. χ3706 was administered perorally to mice and reisolated from the spleen. The animal-passaged strain was designated χ3737. Two other crp mutants, χ3605(crp-773::Tn10) and χ3623 (Δcrp-11) that do not confer the Arg$^-$ or Cys$^-$ auxotrophic traits were also complemented with the pSD110 plasmid by transduction and designated χ3731 and χ3774, respectively. S. typhimurium strains independently carrying cysG and arg mutations were constructed and designated χ3910 (cysG::Tn10), χ4063 and χ4071 (arg::Tn10).

Two other highly pathogenic S. typhimurium strains were selected for attenuation by introduction of the Δcrp-10 mutation. χ3761 (UK-1) and 798 are virulent, invasive strains isolated from a moribund horse and pig, respectively, with $LD_{50}$s in mice of approximately $1\times10^5$ CFU. Transduction of Δcrp-10 with the linked transposon Zhc-1431::Tn10 was facilitated by first making a high-titer bacteriophage P22HTint lysate on the S. typhimurium strain χ3712 (see Table 1.B.). The phage lysate was then used to transduce the genetic traits into the wild-type recipient strains χ3761 and 798. Tetracycline-resistant colonies were selected and screened for the Mal⁻, Arg⁻ and Cys⁻ phenotypes and the resulting 798 derivative designated χ4246 and the χ3761 (UK-1) derivative designated χ4248 (Table 1).

The crp mutation was complemented by introducing pSD110, carrying the crp⁺ wild-type allele, into χ4246 and χ4248. L broth grown cultures of χ4246 and χ4248 were transduced with P22HTint propagated on *S. typhimurium* χ3670, which contains the plasmid pSD110 (Table 1). Selection was made on MacConkey agar+1% maltose+100 μg ampicillin/ml+12.5 μg tetracycline/ml. After 26 h, an ampicillin, Mal⁺ colony of each strain was picked and purified on the same medium and designated χ4247 (798) and χ4262 (UK-1) which both have the genotype pSD110⁺/Δcrp-10 zhc-1431::Tn10.

Virulence of the *S. typhimurium* χ3622, χ3731, χ3737, χ3774, χ3910, χ4063 and χ4071. Table 6 presents data on morbidity and mortality of mice infected perorally with the *S. typhimurium* strains χ3622, χ3731, χ3737, χ3774, χ3910, χ4063 and χ4071. Strain χ3737 was completely avirulent for mice that received $10^4$ times the $LD_{50}$ dose for the wild-type χ3339 parent strain. Mice never appeared ill throughout the 30-day observation period. As a control for this experiment, the crp-773::Tn10 mutation in χ3605 was complemented by pSD110 to the wild-type Crp⁺ phenotype (χ3731) and mice were infected and died. Doses around $1 \times 10^5$ CFU killed 4 of 5 mice p.o. inoculated with χ3731 and χ3774 (pSD110$^{+/\Delta Crp\text{-}11}$). To test the virulence of strains with the Cys⁻ and Arg⁻ phenotypes independently, strains χ3910 (cysG::Tn10), χ4063 (arg::Tn10) and χ4071 (arg::Tn10) were p.o. administered to BALB/c mice. χ3910, χ4063 and χ4071 killed mice when similar or lower doses were p.o. administered. Therefore, the avirulence associated with the Δ[crp-cysG]-10 mutation was not solely due to deletion of the crp gene and was not conferred by deletion of either the argD or cysG loci. Rather, another gene necessary for *S. typhimurium* virulence must be localized to the region of chromosome near the crp gene.

TABLE 6

Virulence of *S. typhimurium* SL1344 Δ[crp-cysG]-10, Crp⁺/crp::Tn10 and Crp⁺/Δ[crp-cysG]-10, arg::Tn10, cysG::Tn10 mutants in BALB/c mice 30 days after peroral inoculation

| Strain number | Relevant genotype | Inoculating dose (CFU) | Survival live/total | Mean day of death[a] | Health[b] |
|---|---|---|---|---|---|
| χ3339 | wild-type | $6 \times 10^4$ | 2/5 | 7 | scruffy |
| χ3622 | Δ[crp-cysG]-10 | $6 \times 10^8$ | 5/5 | — | healthy |
| χ3731 | pSD110⁺ crp-773::Tn10 | $1 \times 10^5$ | 1/5 | 9 | scruffy |
| χ3737 | pSD110+ Δ[crp-cysG]-10 | $5 \times 10^8$ | 5/5 | — | healthy |
| χ3774 | pSD110⁺ Δcrp-11 | $3 \times 10^4$ | 3/5 | 12 | scruffy |
| χ3910 | cysG::Tn10 | $1 \times 10^7$ | 0/2 | 12 | scruffy |
| χ4063 | arg::Tn10 | $1 \times 10^9$ | 0/2 | 8 | scruffy |
| χ4071 | arg::Tn10 | $1 \times 10^9$ | 0/2 | 9 | scruffy |

[a]of animals that died
[b]healthy—no noticeable signs of disease; moderate—moderately ill; scruffy—noticeably ill.

Effectiveness of immunization with χ3622, χ3737, χ4247 and χ4262. Data on the ability of χ3622, χ3737, χ4247 and χ4262 to induce immunity to subsequent p.o. or i.p. challenge with $10^4$ times the $LD_{50}$ doses of fully virulent wild-type *S. typhimurium* cells are presented in Table 7. All mice given excessive doses of the wild-type parent strain never appeared ill throughout the 30-day duration of the experiment. Therefore the Δ[crp-cysG]-10 mutation deletes at least two genes both of which render *S. typhimurium* completely avirulent and highly immunogenic.

TABLE 7

Effectiveness of immunization with avirulent *S. typhimurium* Δ[crp-cysG]-10 mutants in protecting against challenge with wild-type virulent parent strains

| Strain number | Relevant genotype | Dose (CFU) of immunizing strain | Route of immunization | Dose (CFU) of wild-type strain | Survival live/total |
|---|---|---|---|---|---|
| χ3622 | Δ[crp-cysG]-10 | $6.2 \times 10^8$ | PO | $3.6 \times 10^8$ | 5/5 |
| | | $1.5 \times 10^9$ | PO | $3.2 \times 10^8$ | 5/5 |
| | | $4.2 \times 10^8$ | PO | $8.8 \times 10^8$ | 5/5 |
| | | $9.0 \times 10^6$ | IP | $1.4 \times 10^4$ | 2/2 |
| | | $9.0 \times 10^4$ | IP | $1.4 \times 10^4$ | 3/3 |
| | | $9.0 \times 10^2$ | IP | $1.4 \times 10^4$ | 3/3 |
| χ3737 | pSD110⁺ Δ[crp-cysG]-10 | $5.8 \times 10^8$ | PO | $8.4 \times 10^8$ | 5/5 |
| χ3955 | pSD110⁺ Δ[crp-cysG]-14 | $6.8 \times 10^8$ | PO | $8.4 \times 10^8$ | 2/2 |
| χ4247 | pSD110⁺ Δ[crp-cysG]-10 | $2.0 \times 10^9$ | PO | $9.8 \times 10^8$ | 2/2 |
| χ4262 | pSD110⁺ [crp-cysG]-10 | $1.5 \times 10^9$ | PO | $5.4 \times 10^8$ | 3/3 |

Isolation of *S. typhimurium* strain with the Δcrp-14 mutation. Since an imprecise excision event of crp-773::Tn10 generated the deletion of genes extending from argD through cysG, another strategy was designed to locate the position of the gene conferring avirulence in the region adjacent to crp. Twenty independent deletion mutants of χ3910 (cysG::Tn10) were selected on fusaric acid-containing medium and screened for tetracycline-sensitivity and maltose-negative phenotype. One of twenty fusaric acid-resistant derivative of χ3910 had the genotype Δ[crp-cyG]-14 and conferred auxotrophy for histidine and cysteine, but not arginine. This strain, designated χ3931, was, transduced with a P22HTint lysate grown on χ3670 to introduce pSD110 carrying the wild-type crp⁺ gene. An ampicillin-resistant, maltose-positive transductant was picked and purified on the same medium and the resulting strain was designated χ3955.

Virulence of *S. typhimurium* pSD110⁺/Δ[crp-cysG]-14 χ3955. Table 7 shows morbidity and mortality of mice infected perorally with *S. typhimurium* χ3955. Strain χ3955 was completely avirulent for mice that received approximately $10^9$ CFU. Mice never appeared ill throughout the 30-day period.

Effectiveness of immunization with χ3955. Table 7 shows the ability of χ3955 to induce immunity to subsequent p.o. challenge with $10^4$ times the $LD_{50}$ dose of fully virulent wild-type *S. typhimurium* cells. Mice given excessive doses of the parent strain never appeared ill throughout the 30-day duration of the experiment.

Colonization of intestinal tract, GALT and spleen by χ3622(Δ[crp-cysG]-10) and χ3737 (pSD110⁺ Δ[crp-cysG]-10) relative to the wild-type strain χ3339. *S. typhimurium* χ3622 and χ3737 were grown and prepared for oral inoculation of 8-week-old female BALB/c mice as described in Example 1. Animals were sacrificed 1, 3, 5 and 7 days after p.o. inoculation with $9.4 \times 10^8$ CFU (χ3622), $1.2 \times 10^9$ CFU (χ3737) or $1.1 \times 10^9$ CFU (χ3339). Three mice per group were randomly selected, euthanized and tissue samples collected. The spleen, Peyer's patches, a 10-cm section of the ileum and the small intestinal contents from each mouse were placed in polypropylene tubes with BSG, homogenized with a Brinkmann tissue homogenizer and placed on ice. Undiluted or diluted samples (100 µl) were plated directly on MacConkey agar+1% lactose+50 µg streptomycin/ml (χ3339 and χ3737) and MacConkey agar+1% maltose+50 µg streptomycin/ml (χ3622) and the plates were incubated for 26 h 37° C. Titers in the perspective tissues were determined for each time period and the geometric mean calculated for 3 mice per group at each time of sampling.

The additional attenuating mutation in χ3622 and which is still manifested in the Crp⁺ (pSD110⁺) derivative χ3737 very much diminishes the ability to effectively colonize deep tissues. The responsible gene which is deleted by the Δ[crp-cysG]-10 mutation has therefore been designated cdt. The Cdt⁻ phenotype of χ3622 and χ3737 is also manifested by the absence of any splenomegaly which is observed following p.o. inoculation of mice with S. typhimurium χ3623 which has the Δcrp-11 mutation or with various other strains with combined Δcrp and Δcya mutations (Curtiss and Kelly, 1987). Strain χ3737 grew more rapidly than χ3622. The additional attenuating mutation in χ3622 does not decrease growth rate as does the crp mutation.

Based on isolation and analysis of deletion mutations for phenotypes conferred, the order of genes in the S. typhimurium chromosome is inferred to be argD crp cdt cysG.

It is evident that inclusion of the Δ[crp-cysG]-10 or Δ[crp-cysG]-14mutations which are also Δcdt mutations would enhance the safety of live attenuated Salmonella vaccine strains while not diminishing their immunogenicity. This might be particularly important for host-adapted invasive Salmonella species such as S. typhi, S. paratyphi A (S. schottmuelleri), S. paratyphi B (S. hirshfeldii), S. paratyphi C (all infect humans), S. choleraesuis (infects swine), S. dublin (infects cattle), S. gallinarum, and S. pullorum (both infect poultry), as well as non-host specific, invasive Salmonella species such as S. typhimurium and S. enteritidis.

EXAMPLE 4

This example describes the construction of avirulent microbes by the introduction of deletion mutations affecting cAMP synthesis and utilization and an adjacent gene which also governs virulence of Salmonella by affecting colonization of deep tissues and the characterization of strains with two deletion mutations for stability of phenotype, complete avirulence and high immunogenicity.

Bacterial strains. The *Escherichia coli* and *Salmonella typhimurium* strains used are listed in Table 1.A. and B. The maintenance and storage of these strains are as described in Example 1.

Media. Complex media for routine cultivation, enumeration and identification of bacteria are as described in Example 1.

Transduction and fusaric acid selection for loss of Tn10. The media and methods are as described in Example 1.

Construction of S. typhimurium strains with Δcya-12 and Δ[crp-cysG]-10 deletion mutations. The best vaccine strains in terms of efficacy are likely to result from the attenuation of highly virulent strains that display significant colonizing ability and invasiveness. The criteria for selection of these highly pathogenic S. typhimurium wild-type strains such as SL1344 (χ3339), UK-1 (χ3761) and 798 has been described in Example 2.

The wild-type, virulent S. typhimurium strains SL1344, 798 and UK-1 were genetically modified as described below, using classical genetic methods similar to those described in Curtiss and Kelly, 1987. The strategy consists of mobilizing deletions of crp and cya genes that have been isolated and characterized in S. typhimurium SL1344 (as described in Example 1) by placing the transposon Tn10 (encoding tetracycline resistance) nearby the Δcya-12 or Δ[crp-cysG]-10 mutation and transducing the linked traits into the highly virulent S. typhimurium strains UK.-1 χ3761, 798 and SL1344 χ3339 via P22HTint-mediated transduction with selection for tetracycline resistance and screening for a maltose-negative phenotype. The zhc-1431::Tn10 linked to Δ[crp-cysG]-10 and zid-62::Tn10 linked to Δcya-12 were used for this purpose. Neither insertion alone affects the virulence of S. typhimurium.

Transduction of the gene deletions with the linked transposon was facilitated by first making a high-titer bacteriophage P22HTint lysate on the S. typhimurium strain χ3712 containing the Δ[crp-cysG]-10 and zhc-1431::Tn10 mutations and another lysate on the S. typhimurium strain χ3711 containing the Δcya-12 and zid-62::Tn10 mutations. The resulting P22HTint lysates were then used to transduce the genetic traits into the wild-type recipient strains χ3339, 798 and χ3761.

P22HTint propagated on S. typhimurium χ3712 (Δ[crp-cysG]-10 zhc-1431::Tn10) was used to transduce the virulent strains to tetracycline resistance with screening for Mal⁻. The phage-bacteria infection mixtures were incubated for 20 min at 37° C. before 100 µl samples were spread onto MacConkey agar (Difco Laboratories, Detroit, Mich.) containing 1% maltose (final concentration) supplemented with 12.5 µg tetracycline/ml. After approximately 26 h incubation at 37° C., tetracycline resistant Mal⁻ transductants were picked and purified onto the same medium. The resulting 798 derivative was designated χ3777 and the UK-1 derivative was designated χ3779. Strains χ3712, χ3777 and χ3779 all have the genotype Δ[crp-cysG]-10 zhc-1431::Tn10 (Table 1.B.). χ3777 and χ3779 were grown in L broth+12.5 µg tetracycline/ml and each were diluted 1:10 into buffered saline with gelatin (BSG), 100 µl of each were spread onto fusaric acid-containing (FA) media (Maloy and Nunn, 1981) and the plates were incubated approximately 36 h at 37° C. Fusaric acid-resistant colonies of each strain were picked into 0.5 ml BSG and purified onto FA medium. Purified fusaric acid-resistant colonies were picked into L broth and grown at 37° C. to turbidity and checked for loss of Tn10 (tetracycline sensitivity), presence of complete LPS and auxotrophy. The new strains were designated χ3784 (UK-1) and χ3806 (798) which both have the genotype Δ[crp-cysG]-10 Δ[zhc-1431::Tn10]. χ3622 (SL1344 Δ[crp-cysG]-10) was originally isolated as described in Example 1) (Table 1B).

Since the phenotype of Cya⁻ and Crp⁻ mutants are the same (Mal⁻, Stl⁻, Mtl⁻, etc.), the plasmid, pSD110, carrying the cloned crp⁺ gene and conferring ampicillin resistance (Schroeder and Dobrogosz, J. Bacteriol 167:616–622 (1986)), was used to temporarily complement the Δacrp mutation in the chromosome enabling the identification of the Δcya mutation when introduced via transduction. L broth grown cultures of χ3622, χ3784 and χ3806 were transduced with P22HTint propagated on S. typhimurium χ3670, which contains the plasmid pSD110 (Table 1). Selection was made on MacConkey agar+1% maltose+100 µg ampicillin/ml. After 26 h, an ampicillin-resistant, Mal⁺ colony of each strain was picked and purified on MacConkey agar+1% maltose agar+100 µg ampicillin/ml and designated χ3901 (798) and χ3945 (UK-1) which both have the genotype Δ[crp-cysG]-10 Δ[zhc-1431: :Tn10] pSD110⁺ and χ3706 (SL1344) which has the genotype Δ[crp- cysG]- 10 pSD110⁺.

Strains χ3706, χ3901 and χ3945 were grown in L broth+ 100 μg ampicillin/ml and were each independently transduced with P22HTint propagated on χ3711 to introduce the linked Δcya-12 and zid-62::Tn10 mutations. The transduction mixtures were plated on MacConkey agar+1% maltose+ 100 μg ampicillin/ml+12.5 μg tetracycline/ml. Ampicillin-resistant (pSD110⁺), tetracycline-resistant (zid-62::Tn10), Mal⁻(Δcya) colonies were picked and purified on MacConkey agar+1% maltose+100 μg ampicillin/ml+12.5 μg tetracycline/ml. Purified colonies were picked into L broth, grown to turbidity and the strains checked for complete LPS and auxotrophy. The resulting strains were designated χ3902 (798) and χ3956 (UK-1) which both have the genotype Δ[crp-cysG]-10 Δ[zhc-1431::Tn10] pSD110⁺ Δcya-12 zid-62::Tn10 and χ3722 (SL1344) which has the genotype Δ[crp-cysG]-10 pSD110⁺ Δcya-12 zid-62::Tn10. Cultures of χ3722, χ3902 and χ3956 were grown in L broth+100 μg ampicillin/ml+12.5 μg tetracycline/ml to turbidity, diluted 1:10 into BSG, and 100 μl samples of each culture spread onto fusaric acid-containing media and incubated approximately 36 h at 37° C. Fusaric acid-resistant colonies of each strain were picked and purified onto FA medium. Purified FA-resistant colonies were picked into L broth, grown to turbidity and then checked for loss of Tn10. (tetracycline sensitivity), complete LPS and auxotrophy. The pSD110 plasmid was usually lost spontaneously from the strains during this process to result in ampicillin sensitivity, except for the SL1344 and UK-1 derivatives which involved two steps to eliminate pSD110. The final strains were designated χ3958 (UK-1) and χ4038 (798) which both have the genotype Δ[crp- cysG]- 10 Δ[zhc-1431::Tn10] Δcya-12 Δ[zid-62::Tn10] and χ3724 (SL1344) which has the genotype Δ[crp-cysG]-10 Δcya-12 Δ[zid-62::Tn10] (Table 1.B.).

Genotypic and phenotypic stability of avirulent mutants. Methods for determining stability of genetic traits are as described in Example 1. All genotypic and phenotypic traits due to the Δcya Δcrp mutations were completely stable except motility. Although synthesis of functional flagella and display of motility is dependent on wild-type cya and crp gene functions, a suppressor mutation in the cfs (constitutive flagellar synthesis) gene can easily be selected to cause flagella synthesis and motility to be independent of cya and crp gene functions. In S. typhimurium Δcya Δcrp strains, motile variants were readily selected during the strain construction process. Since immunity to flagellar antigens may be protective, motile variants of all vaccine strains were selected.

S. typhimurium group B O-antigen synthesis was confirmed by slide agglutination with antisera (Difco Laboratories, Detroit, Mich.) and by P22HTint bacteriophage sensitivity by the Luria soft agar overlay technique.

Fermentation of sugars and growth on various carbon sources of the double mutant strains were identical to strains with only Δcya or Δcrp as listed in Table 2. The phenotypes were as expected based on published reports of the requirement for cyclic AMP and the cyclic AMP receptor protein for catabolic activities.

At each step in the construction following select on of a fusaric acid-resistant tetracycline-sensitive derivative, an investigation as to whether tetracycline-resistant revertants/mutants could be recovered at frequencies higher than could be observed for the tetracycline-sensitive wild-type parental strain was conducted. In all cases, such tetracycline-resistant revertants/mutants were not observed.

EXAMPLE 5

Construction of Recombinant Avirulent Salmonella Expressing Human LDH-C

Figure 3:
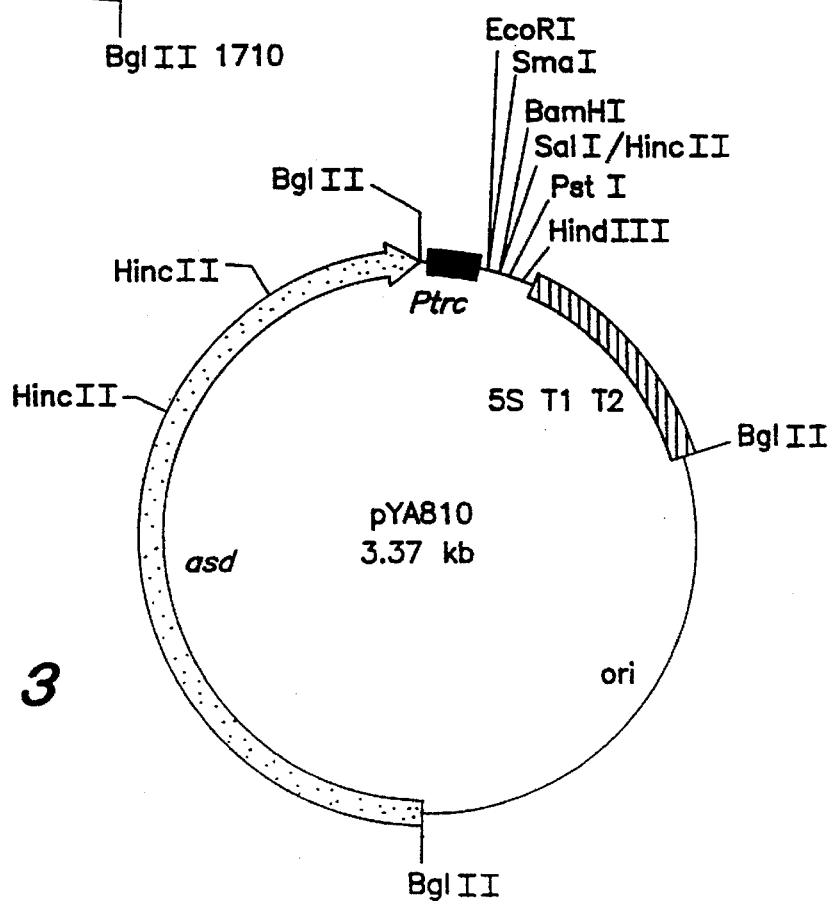
FIG. 3 is a diagram of the Asd$^+$ cloning vector pYA810. The vector contains the trc promoter, a multiple cloning site, the rrnB transcription terminator and the p15a origin of replication. Cloning into the multiple cloning site allows for expression under control of the trc promoter.
Figure 5:
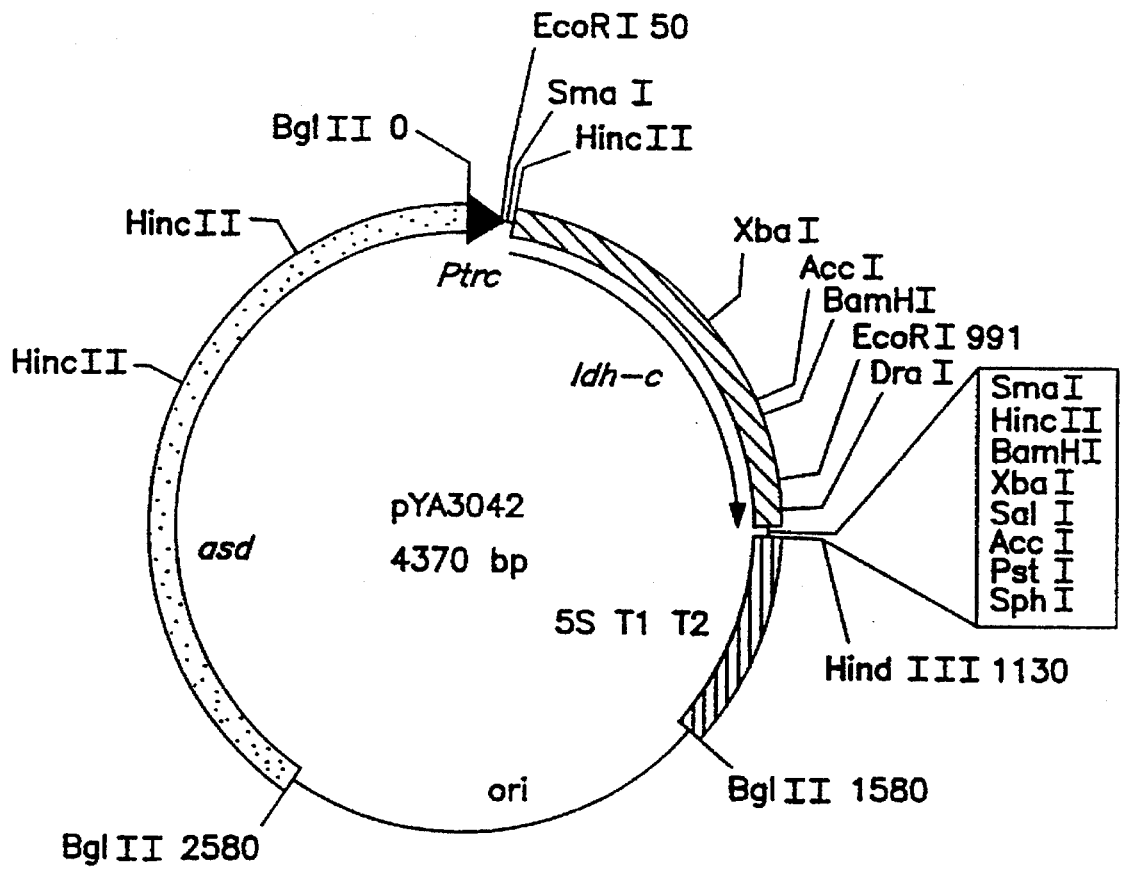
FIG. 5 is a diagram of the Asd$^+$ vector pYA3042 which contains the gene encoding human sperm-specific LDH-C, driven by the trc promoter of pYA810. The figure shows the eight amino acids added to the nucleotide sequence (SEQ ID NO:13) encoding amino acid sequence, SEQ ID NO:58 LDH-C gene (in bold) obtained from pHum-LDH-C inserted into the SmaI-HindIII sites of pYA810.
Figure 6:
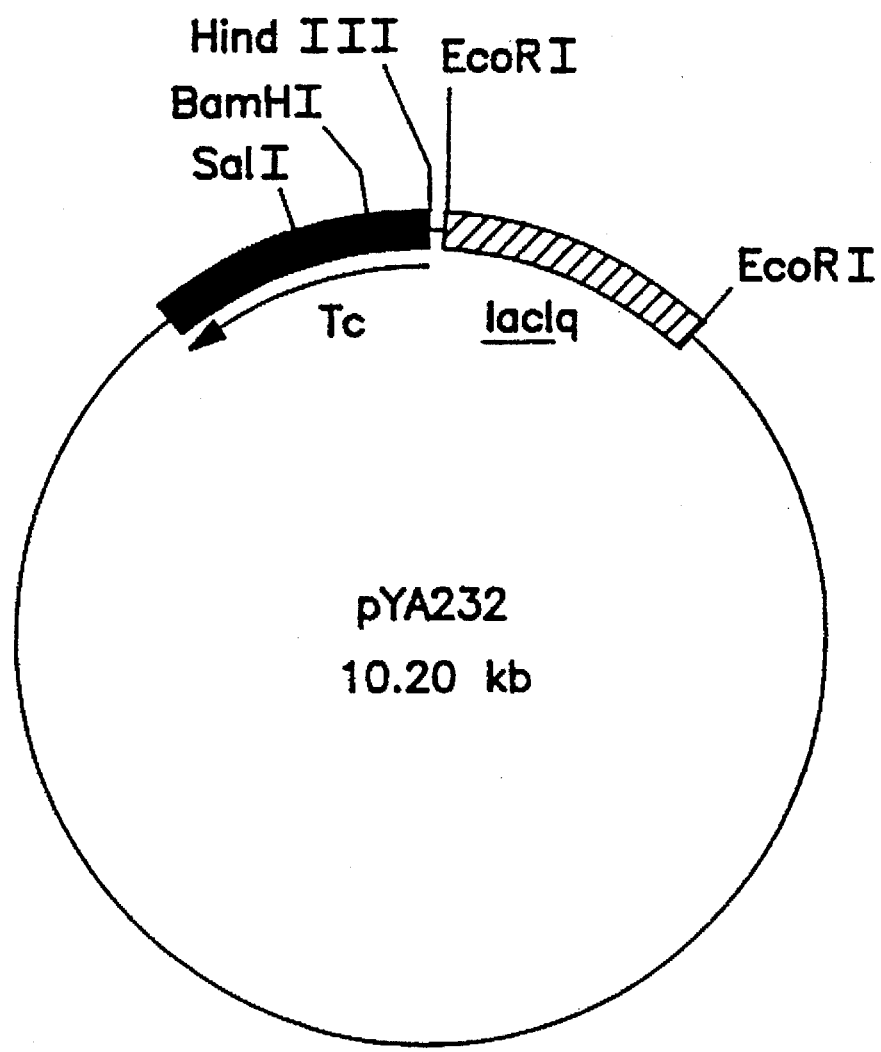
FIG. 6 depicts the lacI$^q$ repressor plasmid pYA232, containing the lacI$^q$ gene on a pSC101 replicon, allowing controlled expression of constructs under the control of Ptrc and related promoters on the p15A replicon used in the balanced-lethal host-vector system.

A. pYA3042 pYA810 (FIG. 3) is an asd⁺ cloning vector suitable for use with Δcya Δcrp Δasd avirulent Salmonella vaccine strains. This plasmid is a derivative of pYA292 (FIG. 2). The multiple cloning site in pYA810 (FIG. 4) affords several strategies for introducing cloned sequences whose expression will be under the control of the constitutively expressing trc promoter. A representative recombinant plasmid which has been constructed using pYA810 is pYA3042 (FIG. 5). This plasmid contains the human sperm-specific LDH-C sequence and was constructed as a protein fusion driven by the trc promoter of pYA810. The insert was obtained as a SmaI-HindIII fragment from pHUM-LDH-C and inserted into the SmaI-HindIII site of pYA810. pYA3042 was originally isolated by transforming the ligated fragments described above into χ6212 (Δ(argF-lacZYA) U169 glnV44 λ⁻φ80d/lacZΔM15 gyrA96 recA1 relA1 endA1 Δzhf-z::Tn10 hsdR17) containing pYA232 (FIG. 6), which provides the lacI$^q$ repressor on a pSC101 replicon. Two clones in this E. coli host containing inserts of the appropriate size (1kb) in the correct orientation were shown by Western blot analysis to produce a protein reacting with polyclonal antisera raised against mouse LDH-C provided that the strains were grown in the presence of the inducer IPTG to overcome lacI$^q$ repression of the trc promoter. One of these isolated recombinant clones, designated pYA3042 (FIG. 5), was then electroporated directly into the Δcya Δcrp Δasd S. typhimurium strain χ3987. Western blot analysis again confirmed the production of a protein reacting with the polyclonal antimouse LDH-C antisera. Such an immunologically reactive protein was undetectable in χ3987 containing the cloning vector pYA810 alone.

Figure 7:
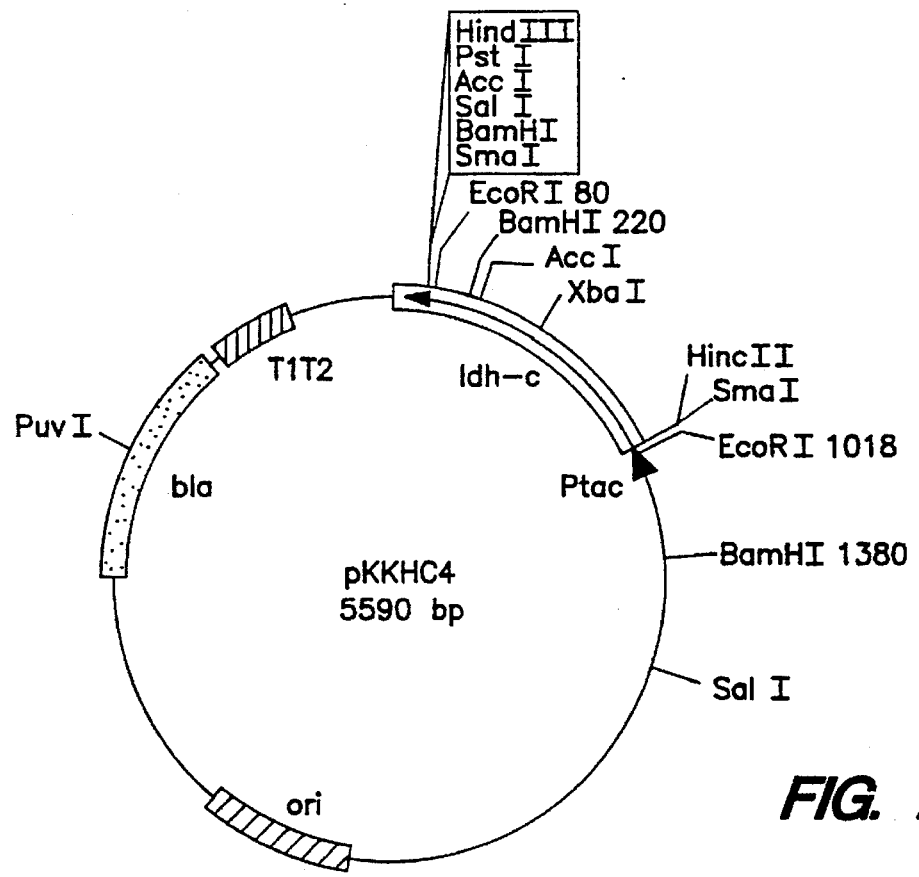
FIG. 7 is a diagram of plasmid pKKHC4 which contains a 966 base pair open reading frame encoding human sperm-specific LDH-C.

B. pYA3054 pKKHC4 (FIG. 7 and LeVan and Goldberg, 1991) is a plasmid containing a 966 base pair open reading frame encoding human sperm-specific LDH-C. The LDH-C cDNA was cloned from a λgt11 human testis cDNA expression library by screening with rabbit antisera and monoclonal antibodies against mouse LDH-C₄ (Millan et al., 1987). The open reading frame was cloned into the XmaI site of pKK233-3 (Pharmacia) by digestion with HincII and DraI, and ligation of XmaI linkers onto both ends.

Figure 8:
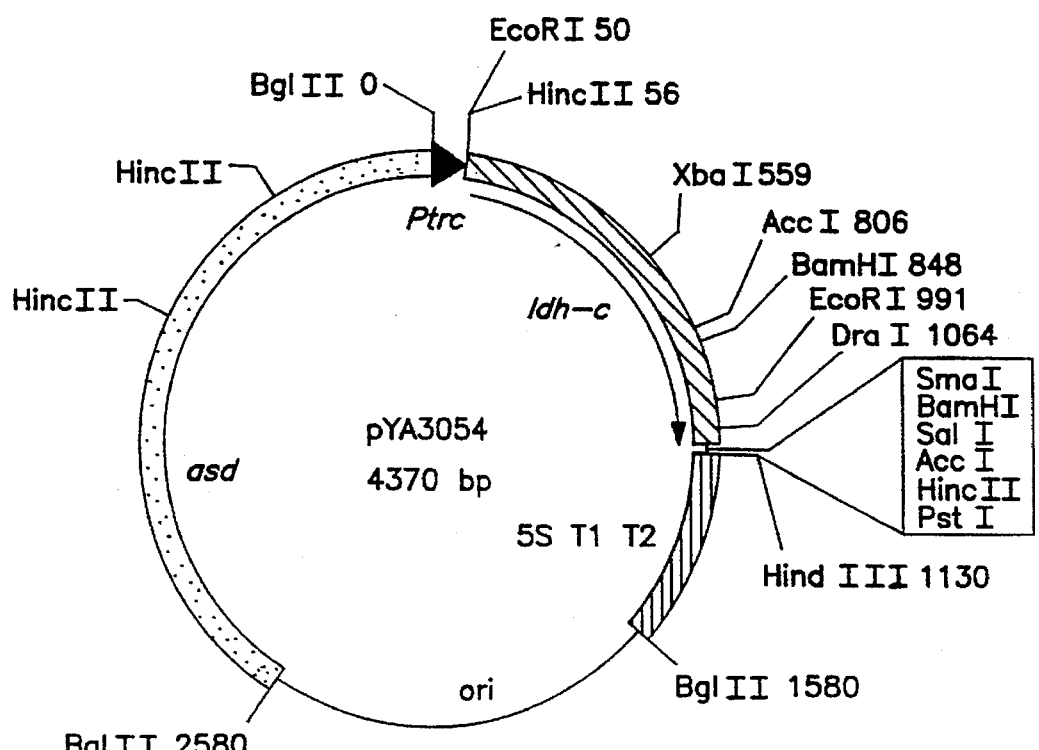
FIG. 8 is a diagram of plasmid pYA3054 with the LDH-C gene cloned as a 1.1 kb EcoRI-HindIII fragment from pKKHC4 into the EcoRI-HindIII site of pYA810.

The fragment containing the LDH-C gene was obtained as a 1.1 kb EcoRI-HindIII fragment following an EcoRI partial-HindIII complete digestion of pKKHC4. This fragment was then inserted into the EcoRI-HindIII sites of pYA810 with expression of LDH-C, with no additional amino acids, driven by the trc promoter as shown in FIG. 8. The LDH-C clone, pYA3054, obtained following electroporation of the ligation mixture into the E. coli host χ6212 (pYA232, specifying LacI$^q$ (FIG. 6)), produced a band of approximately 35 kDa, following IPTG induction, which reacted with rabbit LDH-C (murine) antisera on Westerns, while producing a functionally active LDH-C tetramer as determined by LDH assays on non-denaturing acrylamide gels. This pYA3054 functional LDH-C clone was then electroporated directly into χ3987 (Δcya Δcrp Δasd) to produce an S. typhimurium vaccine strain resulting in constitutive expression of LDH-C.

Prior to immunization of mice with this strain, phenotype, growth rate and plasmid stability were compared relative to the vaccine strain with vector only, χ3987(pYA810). Both χ3987(pYA810) and χ3987(pYA3054) were tested for phage P22 sensitivity (smooth LPS), growth on defined media (protptrophy), inability to ferment maltose (Δcya Δcrp Mal- phenotype), plasmid content (presence of 90 kb virulence plasmid and 4.4 kb pYA3054) and tetracycline sensitivity (Tc$^s$, indicating no lacI$^q$ repressor plasmid, pYA232). Isolated electroporants for both the vector, pYA810, and the LDH-C clone, pYA3054 exhibiting the correct phenotype: P22$^s$, Prot, Mal$^-$, Tc$^{s;}$ were checked for growth rate in Lenox broth and plasmid structural and segregational stability in Lenox broth+diaminopimelic acid (DAP 50 μg/ml) for 60 generations. Plasmid segregational and structural stability of both pYA810 and pYA3054 were determined after approximately 60 generations of growth in Lenox broth containing DAP, without aeration, by both plasmid DNA analysis on agarose gels and functional LDH protein gel assay. These tests revealed that 10/10 isolates of χ3987(pYA3054) contained a 4.4 kb plasmid and produced active LDH-C, while replica plating colonies from LA+DAP (50 μg/ml) to LA—revealed 99.2% of the χ3987 (pYA3054) and more than 99.3% of the χ3987(pYA810) population contained an Asd$^+$ plasmid. Based on this information it was determined that χ3987(pYA3054) would be acceptable for inoculation of mice.

The pYA3054 construct can now be introduced into other Δcya Δcrp Δasd vaccine strains, such as those derived from *S. typhi* described above, to impart human host specificity. Additional constructs producing LDH-C (human) at higher and lower levels, as periplasmic or surface components or fused to the B subunit of the labile toxin (LT) specified by enterotoxigenic *E. coli*, can be made as needed for comparisons.

EXAMPLE 6

Construction of Recombinant Avirulent Salmonella Expressing Human LDH-C with the *E. coli* Heat Labile Toxin B-Subunit (LT-B)

A. pYA3095 and pYA3097

Two constructs, expressing both LDH-C and LT-B, were made as coexpression constructs utilizing the LT-B vector pYA3048 (described below). The B subunit of LT-B serves as an oral adjuvant and also binds to agarose and GM-1 ganglioside, thus facilitating the purification of proteins fused thereto.

pYA3048 (FIG. 9A) is a derivative of pYA810 that includes the LT-B sequence and possesses a multiple cloning site plus two translation termination codons in different reading frame (FIG. 9B) at the terminus of LT-B.

pYA3095 was constructed using pKKHC4 and pYA3048 as depicted in FIG. 10. The construction resulted in the LDH-C gene from pKKHC4 with the tac promoter downstream of the LT-B gene with its trc promoter. Although this clone at first did not appear to hinder growth of the *E. coli* host containing the lacI$^q$ repressor on pYA232 (FIG. 6), χ6212(pYA232), upon induction with 0.5 mM IPTG, poor growth was observed. Poor growth was also observed when this clone was electroporated into χ3987. When Westerns were run to determine if both LT-B and LDH-C were being produced by χ3987(pYA3095), only low levels of LT-B could be detected.

An alternative construct, pYA3097, was made, as depicted in FIG. 10. This plasmid was constructed by inserting the 1.6 kb BglII fragment of pYA3054, which contains the LDH-C coding region with the trc promoter and the 5S T1T2 terminator, into a BglII site of pYA3048. Plasmid pYA3097, obtained from this ligation, resulted in LDH-C with the trc promoter oriented counter-clockwise. This clone did not appear deleterious upon induction with IPTG. When transferred into χ3987, growth rates were slower and recombinational events took place early in the segregational stability tests eliminating the LDH-C portion of the clone. These LDH$^-$ isolates became prominent in the population and represented greater than 90% of the population based on activity assays and plasmid size analysis of 10 isolates.

B. Other LDH-C/LT-B Constructs

Constructs having a single promoter can be made as follows. To produce an operon fusion of LT-B and LDH-C under control of the trc promoter, a synthetic primer can be constructed containing a ribosomal binding site (RBS) 10–15 bp before the LDH-C start. The polymerase chain reaction can then be used to produce the LDH-C coding region with the appropriate BamHI and PstI sites for cloning into pYA3048.

LDH-C/LT-B fusion constructs can also be made as depicted in FIG. 11. The 0.9 kb EcoRI (Mung Bean Nucleased) -PstI LDH-C coding region is isolated from pYA3054 or pKKHC4 and ligated into the MluI (Klenowed) -PstI pYA3048 or pYA3082 LT-B vector. This provides an LT-B-LDH-C protein fusion.

EXAMPLE 7

Construction of Recombinant Avirulent Salmonella Expressing Murine LDH-C

A murine LDH-C clone was constructed utilizing an EcoRI fragment from a murine cDNA clone containing the LDH-C gene. This was cloned into pBS (Stratagene, La Jolla, Calif.) to yield plasmid pBSmLDH. Although the sequence of murine LDH-C is known, very little is known about the LDH-C cloned into the EcoRI site of the vector pBS. Assuming that the cloning would have left the start of LDH-C with a ribosome binding site or in the correct position to allow utilization of an external ribosome binding site, cloning was attemptedby isolating an approximately 1.3 kb EcoRI fragment from pBSmLDH and ligating it into the EcoRI site of pYA810. The correct orientation of the LDH-C insert in these clones was determined by digestion with PvuII and HindIII to reveal an approximately 1.0 kb fragment; however, no functional LDH was detected. The uncertain nature of the 5' end of the murine LDH-C clone requires that a primer be designed based on the sequence data available, to allow direct cloning of murine LDHoC into pYA810 to produce functional LDH-C. This is readily accomplished using standard techniques.

EXAMPLE 8

Purification of Human LDH-C

LDH-C can be purified and used as a coating antigen in ELISAs for monitoring the immune response in immunized subjects. LDH-C can be isolated from any of the expression constructs using standard techniques. However, some of the plasmids containing the LT-B fusions to LDH-C produce an LDH-C which remains fused to LT-B. Accordingly, an alternative construct allowing the isolation of LDH-C without LT-B was made using pMAL vectors supplied by New England Biolabs (FIG. 12). This system involves fusing the protein of interest to the maltose binding protein (MBP) followed by purification of the fusion protein on an amylose column and elution with free maltose.

The pYA3094 construct in *E. coli* χ6101 resulted in a high yield of the MBP-LDE-C fusion, as well as a substantial portion of partial translation products and MBP alone, all of which bind the amylose column. The construct produces a MBP-LDH-C fusion with a Factor Xa site near the start of LDH-C. (Factor Xa recognizes the sequence Ile-Glu-Gly-Arg (SEQ ID NO:52), which is not present in human LDH-C.) The product was cleaved with Xa. Cleavage with this protease results in an LDH-C having three additional amino acids. The digest was then run over another amylose column. Low levels of LDH-C and LDH-C partial products were isolated. Therefore, a MBP-LDH-C fusion mixture was used as the coating antigen for ELISAs. The fusion protein bound to ELISA plates and was capable of giving a maximal response to a 1:1,000 dilution of the rabbit αLDH-C (murine) sera with a 10 µg/ml concentration of fusion protein, while no cross-reaction with murine αχ3987 (pYA810) sera was detected. Accordingly, the fusion is suitable for use in ELISAs.

An alternative C-terminal LDH-C-6XHis fusion construct can be made which utilizes the QIAGEN nickle binding system to isolate full-length LDH-C.

EXAMPLE 9

Animal Immunization

Any of the above recombinant plasmids, expressing LDH-C, can be introduced into other suitable avirulent microbes, such as a Δcya Δcrp Δasd S. typhimurium strain derived from a highly invasive S. typhimurium strain capable of effective colonization of the intestinal tract, especially the GALT. Attenuation of highly invasive strains results in a superior vaccine in terms of the elicited immune responses. χ4072 and χ3987 are examples of such strains. In these strains, the stability of the constructs is evaluated by growing in medium with and without diaminopimelic acid (DAP) and the amount, stability (by employing pulse-chase methodology) and location within the bacterial cell of LDH-C is determined. It should be noted that the fusions to LT-B are likely to be transported across the cytoplasmic membrane into the periplasm. Selected recombinants can be tested to verify that the plasmids have the expected molecular architecture and protein extracts analyzed by polyacrylamide gel electrophoresis using native gels and staining for LDH activity (Goldberg, 1964). Antibody to LDH-C can also be used in Western blot analysis (Towbin et al., 1979) which is important if enzyme activity is undetected.

Finally, strains are grown to log phase in L broth, sedimented by centrifugation, concentrated in buffered saline plus gelatin and used for oral administration.

A. Immunization of Mice

The LDH-C constructs were tested in mice utilizing χ3987(pYA3054) expressing human LDH-C, relative to χ3987(pYA810) containing the vector only. The experiment revealed the colonization ability of the vaccine strain expressing LDH-C and the stability of the construct in vivo. The first strain of mice, C57B16, was selected based on reports that mice of this histocompatability group respond well to LT-B, thus providing a good model for later comparisons with the LT-B and LDH-C constructs. Frozen stocks of χ3987(pYA810) and χ3987(pYA3054), which exhibited the correct phenotype and has been utilized in the stability tests, were used to start 2–3 ml cultures in Lenox broth without aeration at 37° C. These cultures were then diluted 1:20 into warm Lenox Broth and grown with aeration to an optical density of approximately 1.0 $ABS_{600}$, prior to pelleting of the cells and resuspension in buffered saline gelatin. Twelve 8 week old C57B16 female mice were orally inoculated, according to standard protocols, with $1.2 \times 10^9$ colony forming units (CFU) of χ3987(pYA810), while another twelve were inoculated with $9.6 \times 10^8$ CFU of the LDH-C (human) vaccine strain, χ3987(pYA3054). Ten days after the first inoculation, the 6 mice in each group selected for immunological study were given a booster of $1.5 \times 10^9$ CFU of χ3987(pYA810) and $8.6 \times 10^8$ CFU of χ3987 (pYA3054) following the procedures used for administration of the first inoculum. The colonization of both strains was monitored by sacrificing 3 mice from each primary inoculation group on days 7 and 14.

Figure 13:
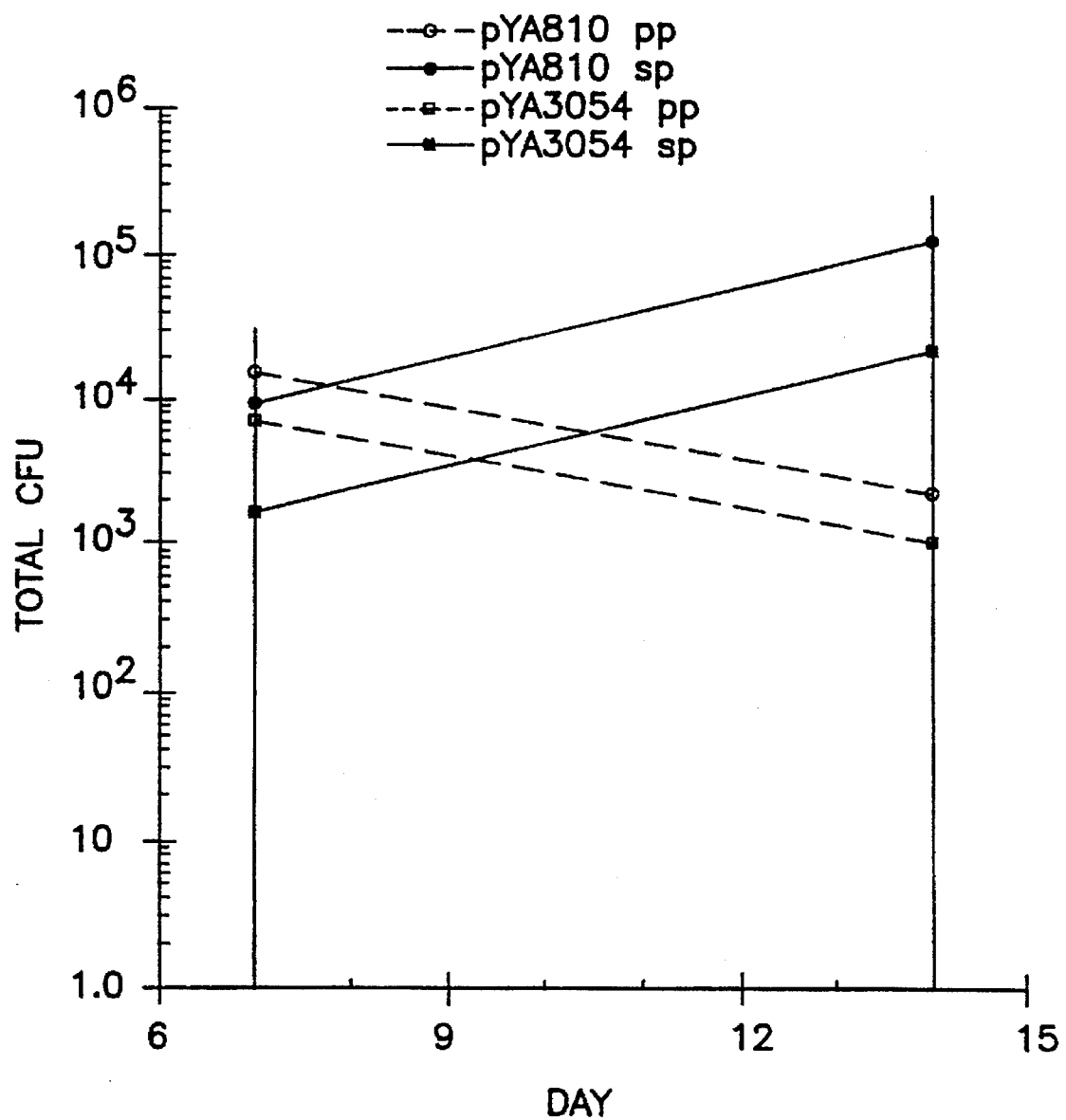
FIG. 13 shows the number of colony forming units (CFU) of recombinant Salmonella expressing LDH-C recovered from mice, as described in Example 9.
Figure 14:
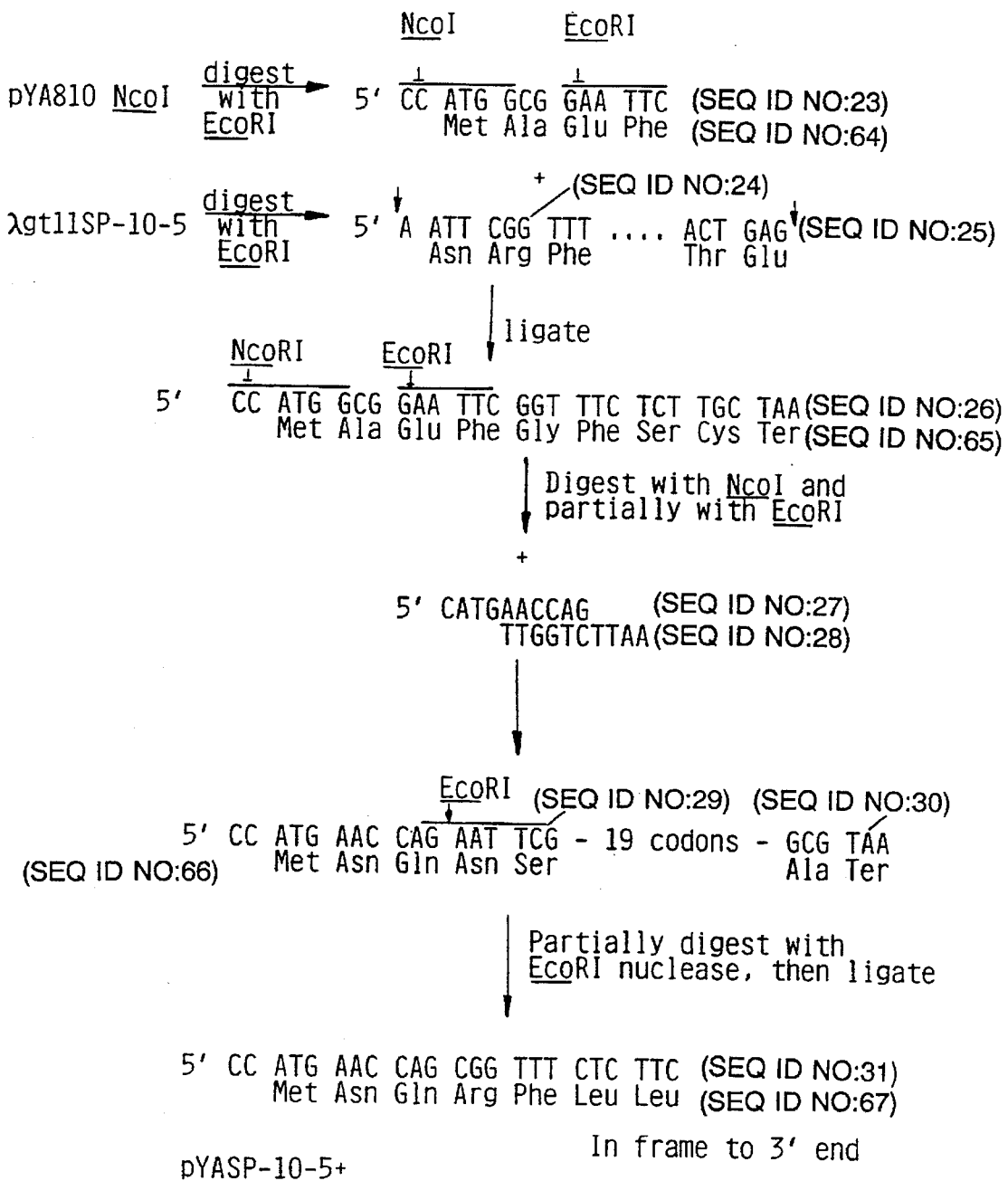
FIG. 14 shows the construction of pYASP-10-5+. The non-SP-10 specified amino acid sequence 3' to the EcgRI site can be eliminated to yield pYASP-10-5ter by insertion of a polynucleotide specifying two aspartate residues followed by a termination codon.

The total numbers of CFU recovered from Peyers patches (pp) and spleens (sp) are depicted in FIG. 13 and in Table 8, revealing that χ3987(pYA3054) was present in slightly lower numbers (although one animal was not colonized for χ3987(pYA3054) on day 7 and not included). The animals appeared healthy externally throughout the study, however, when the mice were dissected on day 14 they exhibited enlarged spleens and livers, suggesting that the dose given may be higher than desired for this strain of mice. The structural stability of pYA3054 in vivo was determined by picking five isolated colonies obtained from the spleens of three different animals on day 14 and testing for functional LDH activity. All 15 isolates screened produced functional LDH-C according to the LDH activity gel, indicating that more than 93% of the population reaching the spleen was expressing LDH-C 14 days after oral immunization. While one group of mice had been used for tracking, the other group was monitored for immune responses by collection of sera via retriorbital bleeds one week and collection of saliva and vaginal secretions the next week beginning on week 4, following the primary immunization and continuing through week 8, after which time male C57B16 mice were introduced to the females (1 male/2 females).

The immune responses of both groups of mice are evaluated by ELISA for both serum IgG and sIgA response and the mice monitored for indications of reduced fertility.

TABLE 8

Recovery of χ3987(pYA810) or χ3987(pYA3054) from the Peyers Patches and Spleens of C57 Black Mice

| | Mean Total CFU ± SD* Day | |
|---|---|---|
| Clone (tissue) | 7 | 14 |
| pYA810 (pp) | $1.6 \times 10^4 \pm 1.3 \times 10^4$ | $2.5 \times 10^3 \pm 1.7 \times 10^3$ |
| pYA810 (sp) | $9.4 \times 10^3 \pm 1.2 \times 10^4$ | $1.4 \times 10^5 \pm 8.8 \times 10^4$ |
| pYA3054 (pp) | $6.3 \times 10^3 \pm 5.3 \times 10^3$ | $1.2 \times 10^3 \pm 7.4 \times 10^2$ |
| pYA3054 (sp) | $1.7 \times 10^3 \pm 1.7 \times 10^3$ | $1.8 \times 10^4 \pm 1.0 \times 10^4$ |

*Mean data obtained from three mice per time point.

Immunization of Rabbits. Most studies on induction of a generalized secretory immune response have examined sIgA titers in saliva, intestinal washings, tears and sometimes in milk. There has been very minimal work done on the production of sIgA in the reproductive tract as a consequence of antigen delivery to the GALT. In order to do so, five female rabbits are immunized and the secretory and humoral immune responses investigated as noted above for mice. In addition, vaginal secretions are collected by lavage for the quantitation of sIgA against LDH-C. These experiments are particularly informative in that rabbits are outbred and some differences in immune response can be anticipated if there are significant differences in immune response to LDH-C dependent upon histocompatibility and immune response genotype. If such variability is encountered, a vaccine expressing several sperm-specific antigens will be useful.

EXAMPLE 10

1. Construction of Recombinant Avirulent Salmonella Expressing SP-10

A. Modification of pYA810 Vector by Site-Directed Mutagenesis. The λgt11 clones SP-10-5 and SP-10-10 (Wright et al., 1989) can be excised from the λgt11 vectors with EcoRI (see FIG. 1). However, cloning the SP-10-5 sequence into the EcoRI site in the pYA810 vector would yield an out of frame fusion and would place amino acids at the N-terminal end which would likely decrease secretion of the protein across the cytoplasmic membrane of *E. coli* and *S. typhimurium*. Thus, an NcoI site (CCATGG) is created in pYA810 by site-directed mutagenesis so that the sequence CC ATG CCG GAA TTC (SEQ ID NO:3) encoding the amino acids Met Pro Glu Phe (SEQ ID NO:53) are changed to CC ATG GCG GAA TTC (SEQ ID NO:2) encoding Met Ala Glu Phe (SEQ ID NO:54). This vector is useful in that it creates another usable cloning site since NcoI does not cut pYA810. The correct nucleotide sequence in the mutated pYA810 is determined by sequencing and also by demonstrating the existence of the new NcoI site with retention of the EcoRI site.

B. Construction of a Vector With the N-terminal SP-10 Sequence. This construction is diagrammed in FIG. 14. The pYA810-NcoI vector is cleaved with EcoRI and the 635 base pair EcoRI fragment excised from the λXgt11 clone SP-10-5 (FIG. 1) (i.e., base pairs 62 to 696) is inserted by ligation. The recombinant constructs are transformed or electroporated into the recA hsdR Δasd *E. coli* host χ6212 which has a plasmid-encoded lacI$^q$ gene so that expression of any sequence under the control of the trc promoter is dependent on the presence of the inducer IPTG. Recombinant clones with the correct orientation of the SP-10-5 sequence are identified by digesting DNA with SmaI (cutting once in the vector; see FIG. 4) and XhoII (which cuts about 40 bp from the 5' end of the 635 base pair SP-10 coding sequence (see FIG. 1) and with SmaI and BclI (which cuts about 45 bp from the 3' end of the SP-10 coding sequence (see FIG. 1). A clone with the correct orientation is selected and it is verified that no protein is synthesized that reacts with anti-SP-10 antibody (a stop codon is reached after eight amino acids are polymerized into a polypeptide; see FIG. 15).

DNA from this plasmid is then cut to completion with NcoI and partially with EcoRI (sometimes this will lead to excision of the SP-10-5 sequence just inserted but sometimes not; see FIG. 10). The following hybridized linker is added to the mixture:

```
5' CATGAACCAG 3' (SEQ ID NO: 4)
    3'    TTGGTCTTAA 5' (SEQ ID NO: 5)
```

This is ligated to the cleaved vector to result in insertion of codons for the amino acids, asparagine and glutamine after the ATG Met codon. (The N-terminal end can be made more basic to see if secretion is improved by subsituting the lysine codon/LAG for either the AAC asparagine codon or the CAG glutamine codon. In either case, the EcoRI site is regenerated.) This construct should still not synthesize SP-10 protein antigen and this will be confirmed. The plasmid so generated is partially cut with EcoRI. The 5' single-stranded extensions are removed by nuclease treatment followed by blunt-end ligation to delete four base pairs. The recombinant plasmids are transformed or electroporated into the *E. coli* strain χ6212 and transformants screened for production of SP-10 antigen by colony immunoblotting. The positive recombinant clones are analyzed for correct location of various restriction enzyme cleavage sites (see FIGS. 1 and 4). The only difference at the N-terminal end compared to the amino acid sequence of SP-10 is the insertion of a glutamine as the third amino acid. At the C-terminal end there is no immediate termination codon in the vector and thus the protein produced will have twenty-nine additional amino acids since the first in frame transcription stop signal is specified in the rrnB sequence in the pYA810 vector. (This is the basis for the + in the designation of this recombinant vector pYASP-10-5$^+$.)

Preliminary experiments are conducted to see how well the cells grow with and without IPTG and whether in the presence of DAP the recombinant plasmid is selectively lost. It is also determined whether the SP-10 protein is efficiently transported to the periplasmic space by fractionating cells using cold osmotic shock. Based on this, it is determined whether the additional amino acid sequence at the C-terminal end is beneficial, harmful or neutral. If harmful, pYASP-10-5$^+$ DNA will be cut with EcoRI and the following linker inserted:

```
5' AATTCTGACGATT 3' (SEQ ID NO: 6)
    3'    GACTGCTAATTAA 5' (SEQ ID NO: 7)
```

This will result in codons for the C-terminal amino acid sequence Asn, Ser, Asp, Asp followed by a TAA termination codon. The plasmid generated in this manner is termed pYASP-10-5ter.

C. Insertion of C-Terminal SP-10 Sequence Into pYASP-10-5$^+$. Another way to terminate translation and eliminate non-SP-10 amino acid sequences at the C-terminus is to insert the EcoRI to XbaI SP-10 sequence (approximately 162 base pairs) obtained from the Xgt11 clone SP-10-10 (see FIG. 1). This construction to generate pYASP-10ter is depicted in FIG. 16. This fragment is isolated and ligated to pYASPT10-5$^+$ DNA that has been digested to completion with EcoRI and SmaI. Following ligation, the Klenow fragment of DNA polymerase is added to fill in the complement to the single-stranded 5' overhang for the XbaI site followed by ligation to the blunt ended SmaI site. This generates full-length SP-10 with the C-terminal Ile codon followed by a TAG stop codon. The protein synthesized in the presence of IPTG should be the same as the SP-10 protein except for the additional glutamine as the third amino acid. The protein will therefore have 266 amino acids.

D. Construction of SP-10 Fusion to LT-B. The pYASP-10ter plasmid (FIG. 16) is digested to completion with AlwI and the cut vector treated with Klenow to blunt-end the AlwI site followed by digestion with PstI and recovery of the 769 base pair fragment (see FIG. 1). The LT-B fusion vector pYA3048 (FIG. 9A) is digested with ApaLI (FIG. 9B), treated with Klenow to fill in the complements to the 5' single-stranded overhangs and then digested to completion with PstI. The two molecules are ligated together and the recombinant molecules electroporated into *E. coli* χ6212. The construction of the resulting plasmid, pYALT-B-SP-10, is depicted in FIG. 11. The synthesis of the LT-B-SP-10 fusion will be dependent upon IPTG induction. This is evaluated by performing Western blot analysis using antisera to both LT-B and SP-10. It is also determined whether the fusion product is in the periplasmic space by conducting cell fractionation studies using cold osmotic shock and Western blot analysis. If so, it is determined whether the fusion forms a pentamer in the periplasm. LT-B pentamers are stable to 60° C. in 0.1% SDS and do not react with antibodies to LT-B monomers following SDS polyacrylamide gel electrophoresis. The pentameric LT-B disassociates at 70° C. or above in the presence of 0.1% SDS to yield monomeric molecules which now strongly react with the antisera against the LT-B subunit. Thus, testing immunogenicity following treatment at different temperatures can reveal whether pentamers do or do not form.

E. Characterization of Recombinant Clones. A diversity of comparative tests are conducted with pYASP-10-5$^+$, pYASP-10-5ter, pYASP-10ter and pYALT-B-SP-10 in *E. coli* χ6212 and in the *S. typhimurium* Δcya Δcrp Δasd strains χ4072 and χ3987. Growth rates are examined with and without IPTG, quantitative levels of expression determined using either ELISA or quantitative Western blot analysis employing a Molecular Dynamics densitometer. The location of the expressed gene product is determined by cell fractionation employing cold osmotic shock. Cultures are grown over a substantial period of time to determine whether there is any genetic instability. Computer analysis of the SP-10 nucleotide sequence (FIG. 1) reveals both extensive direct repeats and partial inverse repeats. The direct repeats could lead to increases or decreases in the length of the coding sequences as a consequence of recombination between progeny chromosomes during plasmid replication. If such genetic instability is revealed, recA avirulent Salmonella strains cannot be used since recA further attenuates Salmonella. Rather, mutants with a recF mutation are used since it blocks inter- and intraplasmidic recombination (James et al., 1982) and may not have an adverse effect on the virulence of Salmonella by hyperattenuating the vaccine strains.

Whether the plasmids are maintained or not in the presence or absence of DAP during growth over 50 to 100 generations is determined. The stability of the protein using pulse chase methodology is also determined. Finally, for the LT-B-SP-10 fusion, the binding to GM-1 gangliocide and/or agarose is determined as a procedure for purification of the fusion protein.

2. Alternative Construction of a Recombinant Avirulent Salmonella Expressing SP-10

A. Construction of Asd$^+$ Vector Specifying the N-Terminal SP-10 Sequence

An Asd$^+$ vector, pYA3098, with an NcoI site immediately downstream from the Shine-Dalgarno sequence was constructed (FIG. 20). This vector will very much facilitate making a series of constructs specifying all or part of the SP-10 antigen. PCR amplification of the SP-10 sequence specifying the N-terminal 163 amino acids starting with the Gly immediately preceding the usual cleavage site of the SP-10 signal sequence (FIG. 1) is used. Oligonucleotides are synthesized to prime the synthesis of this fragment. The 5' end is the oligo 5'-GACCATGGGAACATCAAGTCAG-3' (SEQ ID NO:8). All but the first seven nucleotides, which encompass the NcoI site, are present in the coding sequence for SP-10. The oligonucleotide for the 3' end is 3'-GTCCACGTGGTTAAAGTTCGCTTAAGGG-5' (SEQ ID NO:9). This oligonucleotide contains an EcoRI site at the C-terminal end of the coding sequence. In order to prevent synthesis of a polypeptide on the end of the SP-10 sequence that is not derived from SP-10, an oligonucleotide is inserted between the EcoRI and BamHI sites in pYA3098 (FIG. 20) in order to have stop codons in each of the three reading frames. The oligonucleotide 5'-TTAAGTAGGTAAATAG (SEQ ID NO:10) and its complement, 3'-CATCCATTTATCCTAG-5' (SEQ ID NO:11) are synthesized. After hybridization, this sequence is inserted into pYA3098 previously cut with EcoRI and BarnHi. This will cause the insertion of TAG, TAA, and TAG translation stop, codohs in each of the three reading frames. This new vector is termed pYA3098 stop. The PCR-amplified SP-10 coding sequence will be digested to completion with NCoI and EcoRI and the insert ligated into pYAB3098 stop digested with NcoRI and EcoRI. The recombinant vector will be electroporated into *E. coli* χ6212, a derivative of DH5a with pYA232 containing the lacI$^q$ gene. Expression of the SP-10 fragment from the trc promoter in the pYA3098stop vector (FIG. 20) will therefore be dependent upon addition of IPTG. The resulting construct should specify a polypeptide of 167 amino acids. Other cloning strategies can be used such as placing a stop codon immediately after the Ser present in SP-10. This recombinant clone will be designated pYASP-10Nter. This fragment of DNA, when present in *E. coli* strains, appears to specify high-level production of the SP-10 polypeptide. It is also known from other studies that this sequence contains all of the amino acid sequences in the polymorphic forms of SP-10 found in human sperm.

B. Construction of an Asd$^+$ Vector with the C-Terminal SP-10 Sequence

The SP-10 sequence contains an ApaLI site at nucleotide 587 and an XbaI site that overlaps the C-terminal termination codon TAG. The SP-10 sequence is initially cleaved with ApaLI and the single-stranded tails digested with mung bean nuclease. This results in a blunt end with the first codon specifying Pro. The DNA is then cut with XbaI and the Klenow fragment of DNA polymerase used to fill in to result in a blunt-ended fragment ending with the TAG termination codon. pYA3098 is digested to completion with NcoI and the Klenow fragment used to fill in the complement to the 5'-ended overhang. The two modified DNA molecules are blunt-end ligated and electroporated into χ6212 containing pYA232. The desired construct with the correct orientation should specify a product of 119 amino acids with the 118 amino acids following the initial Met being exactly as specified by SP-10. This protein fragment will overlap that specified in pYASP-10Nter by four amino acids. This new construct will be designated pYASP-10Cter.

C. Construction of Fusions Between LT-B and the N-Terminal Portion of SP-10

As above, the LT-B fusion vectors, pYA3048, which possesses a signal sequence so that the product is transported to the periplasm and pYA3082, which lacks the signal sequence and will cause the product to remain in the cytoplasm, can be employed. The procedures for both vectors are the same. pYASP-10Nter, constructed as described above, is cut with NcoI followed by treatment with Klenow fragment to fill in the complement to the 5' overhang. The sequence is then cut with PstI in order to include the previously inserted termination stop codons in pYA3098stop. The pYA3048 and pYA3082 vectors are cleaved with ApaLI and digested by mung bean nuclease to result in blunt-ended molecules. The vectors are cut to completion with PstI. The insert and vector molecules are ligated together and introduced into χ6212 containing the lacI$^q$ gene on pYA232. The constructs are designated pYALT-B-SP-10NterPer and pYALT-B-SP-10NterCyt. The ability to synthesize a protein that reacts with antibodies to SP-10 and LT-B following IPTG induction is investigated, as well as the viability of cells grown continuously in the presence of IPTG. The construct with the fusion that permits stable, high-level expression with stability of the plasmid insert is used in subsequent studies. If the construct with the signal sequence is viable when grown in the presence of IPTG, cold osmotic shock and Western blot analysis are used to verify that the LT-B/SP-10 fusion is in the periplasmic space. It is then determined whether the fusion forms a pentamer in the periplasm. LT-B pentamers are stable up to 60° C. in 0.1% SDS and do not react with anti-LT-B antibody following SDS polyacrylamide gel electrophoresis. The pentameric LT-B disassociates at 70° C. or above in the presence of 0.1% SDS to yield monomeric molecules which now readily react with antisera against the LT-B monomer subunit. Thus, testing antigenicity following treatment at different temperatures can reveal whether pentamers do or do not form.

D. Characterization of Recombinant Clones

As above, a diversity of comparative studies, with the four types of constructs described when present in E. coli χ6212 which contains the lacI$^q$ plasmid pYA232 and in the S. typhimurium Δcya Δcrp Δasd strain χ3987 which does not have the lacI$^q$ gene, are conducted. Growth rates with and without IPTG are examined and the quantitative levels of SP-10 synthesis determined using ELISA and quantitative Western blot analysis. Depending on the results of these tests, it is decided whether to construct vectors delivering the SP-10Nter and SP-10Cter proteins to the periplasm of E. coli and S. typhimurium. This can be readily accomplished using the LT-B fusion vector pYA3048 since there is a very convenient SacI site that cleaves just after the first amino acid in the mature processed LT-B, thus leaving the entire LT-B signal sequence intact. Construction of these recombinants employing PCR technology and various restriction sites present in existing constructs is straightforward.

The location of the expressed gene product is determined by cell fractionation employing cold osmotic shock. Cultures are grown in a substantial period of time to determine whether there is any genetic instability. Computer analysis of the SP-10 nucleotide sequence (FIG. 1) reveals both extensive direct repeats and partial inverse repeats. The direct repeats could lead to increases or decreases in the length of the coding sequences as a consequence of recombination between progeny chromosomes during plasmid replication. If such genetic instability is revealed, recA avirulent Salmonella strains could not be used since recA further attenuates Salmonella. Rather, the use of mutants with a recF mutation is investigated since it blocks inter- and intraplasmidic recombination.

It is determined whether or not the plasmids are maintained in the presence or absence of DAP during growth over 50 to 100 generations. The stability of the protein is investigated using pulse chase methodology. Lastly, for the LT-B/SP-10 fusion, binding to GM-1 ganglioside and/or agarose is evaluated for purification of the fusion protein.

3. Purification of SP-10

After optimizing the level of production of the LT-B-SP-10 fusion proteins in the recombinant avirulent Salmonella, the fusion proteins are purified. In order to avoid contaminating LPS, the Δcrp Δasd S. typhimurium LT-2 derivative χ4153 which has a galE mutation to eliminate LPS core and O antigen production is used. Tn10 insertions in the genes for flagella and Type I pili are also introduced in the strain to avoid contaminating the antigen preparation with pilus and flagellar antigens. Cold osmotic shock is employed as the first step in the purification of the fusion protein. This generally gives a 15- to 20-fold purification over total cellular protein. Either a GM-1 affinity column (Tayot et al., 1981) or agarose (Clements and Finkelstein, 1979) is used, depending upon which gives the better affinity and reversibility of attachment to the fusion protein. The purity of the fusion protein is tested during development of the purification protocol measuring total proteins by standard methods and the fusion protein by quantitative ELISA. Purified fusion protein are lyophilized for long-term storage.

4. Animal Immunization

Animals are immunized and studied as described above in Example 9.

5. Synthesis of SP-10 Sequences With Optimal Codon Usage for High Level Expression There is a distinct bias in the codons used in genes that are highly expressed in E. coli and S. typhimurium as opposed to the codons that are used in genes that are expressed at low level (Ikemura, 1985, Gouy and Gautier, 1982). A computer analysis of the coding sequence for SP-10 (FIG. 1) reveals that of the 265 codons, eight are essentially never used in genes expressed at high level in E. coli and 43 others are only used at frequencies of one to four percent in highly expressive genes. Thus, oligonucleotide synthesis is used to synthesize 40 mers to 50 mers with optimal codon usage for high level expression in E. coli and S. typhimurium. These oligomers are then fused to LT-B using a derivative of pYA3048 (FIG. 9A and 9B) or pYA3082. The vector can be cleaved with either MluI and PstI or ApaLI and PstI so the single-stranded molecule can be cloned with enzymatic synthesis of the complementary strand using Klenow fragment DNA polymerase. Prior to doing this, however, it is necessary to modify the sequence between the PstI and HindIII sites in pYA3048 (see FIG. 9B) to insert translation stop signals in each of the three reading frames. This will be called vector pYA3048 ter.

In order to facilitate epitope mapping, a set of constructs is made with overlapping fragments. The result is approximately 30 recombinant clones where the SP-10 polypeptide is fused to the LT-B sequence.

The ability of each of these clones to specify a polypeptide that reacts with antisera against SP-10 is analyzed. Antisera from vasectomizedmales or males or females with other fertility impairments that may have immunological basis are also used.

Epitopes that are highly reactive with antibody are also used in a recombinant avirulent S. typhimurium vaccine strain to determine whether they are highly immunogenic in eliciting antibody response against SP-10 or human sperm after the acrosome reaction.

6. Assembly of a Synthetic SP-10 Coding Sequence for Maximal Expression, Stability and Immunogenicity Based on the results of the experiments described above, an intact SP-10 molecule or possibly larger segments of it are assembled in the clones described in Section 4 of Example 10 above.

Upon completion of the construction of these variants, the experiments described in Sections 2 and 3 are conducted and the purified SP-10 molecule used for secondary immunization and for quantitative ELISA analysis of antibody titers to SP-10 in the human population including individuals with and without impairment of fertility functions.

EXAMPLE 11

Construction of Recombinant Avirulent Salmonella Expressing Murine ZP3

Figure 18:
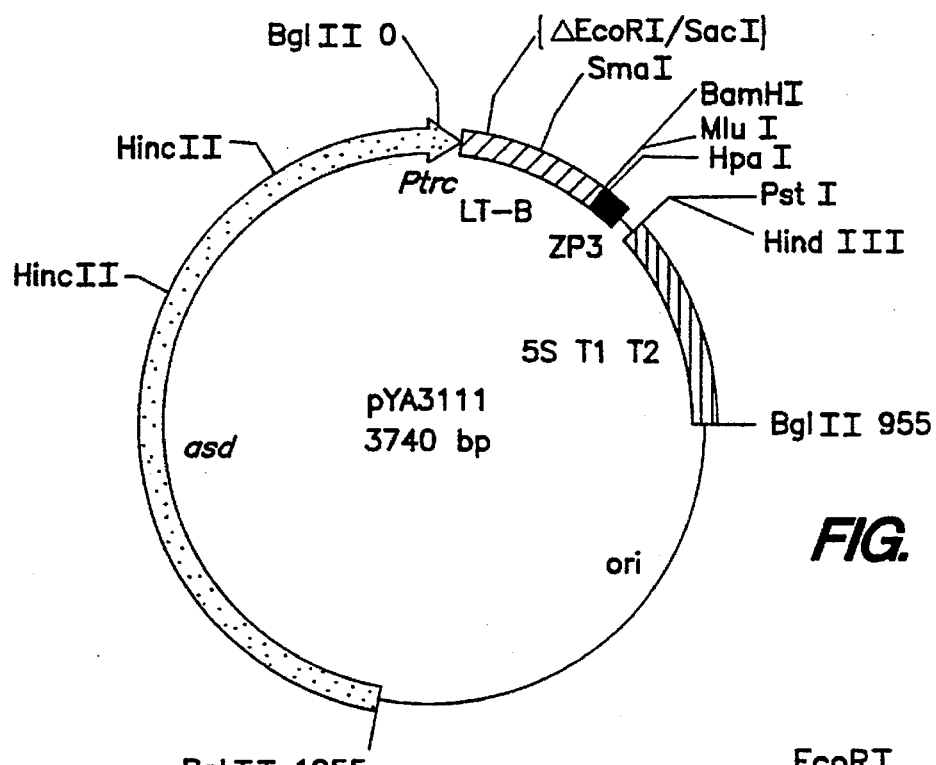
FIG. 18 shows the pYA3111 LT-B-ZP3 cytoplasmic fusion construct obtained by ligating the anealed 50 bp synthetic oligomers into the MluI site of pYA3082.
Figure 19:
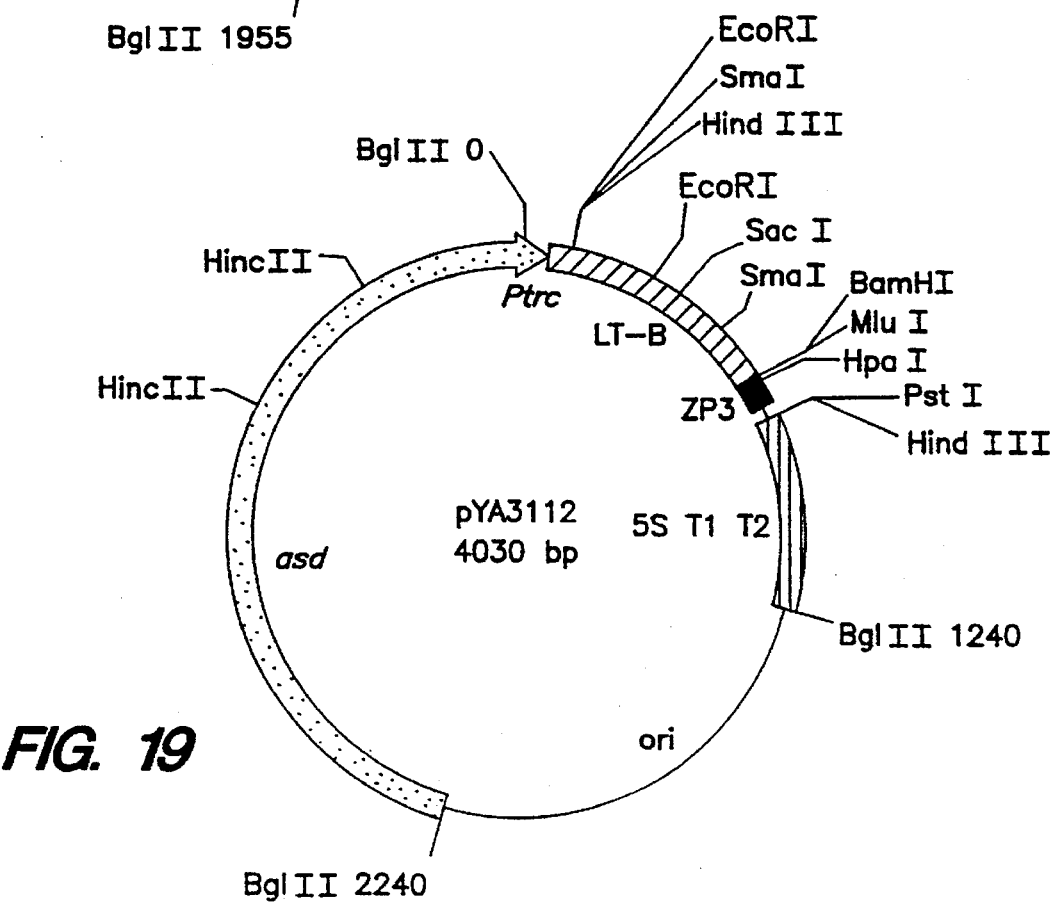
FIG. 19 depicts the LT-B-ZP3 periplasmic protein fusion construct, pYA3112, obtained by ligating the ClaI-PstI fragment of pYA3111 into the ClaI-PstI site of pYA3048.
Figure 20:
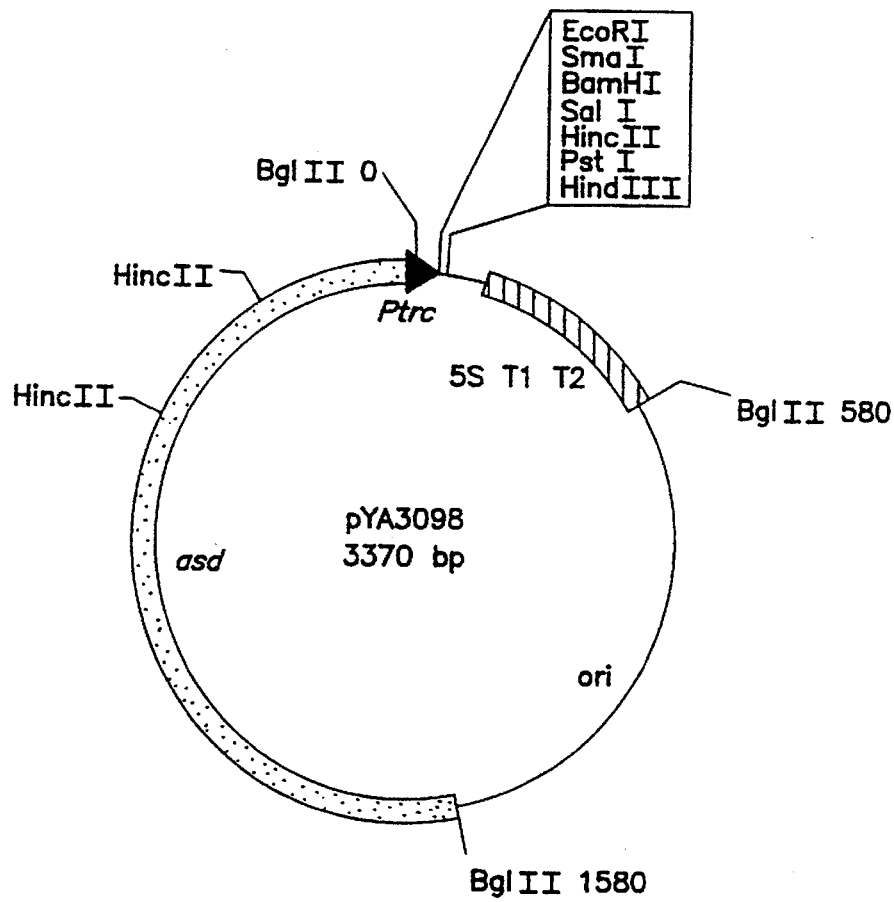
FIG. 20 depicts the asd+ expression vector pYA3098 used in the construction of pYASP-10Nter and pYASP-10Cter.

An LT-B-ZP3 fusion was made as diagrammed in FIG. 17, by ligating the annealed synthetic ZP3 50 bp oligomers into the MluI site of pYA3082 to yield plasmid pYA3111 (FIG. 18). Colony immunoblot screening of approximately 800 colonies with mouse αZP3 (murine) sera revealed three positive clones. These three clones were confirmed to produce an approximately 14 kMW protein which reacted with αZP3 on a Western and to contain a HpaI site within the insert. The approximately 0.3 kb ClaI - PstI fragment of pYA3111, FIG. 18, containing the ZP3 peptide coding region, was then introduced into the ClaI - PstI sites of pYA3048 to yield pYA3112 (FIG. 19), which provides an LT-B-ZP3 fusion protein with a twenty-two amino acid signal sequence. Although both of these ZP3 clones express LT-B fusion proteins of approximately 14 kMW which react with mouse αZP3 sera, the LT-B fusion protein containing the signal sequence can be deleterious to cell growth when fully induced. Therefore, pYA3112 was introduced into χ3987 with the lacI$^q$ repressor plasmid pYA232. When pYA3112 is present in cells without any repressor, viable cells appear with rearrangements of the LTB-ZP3 fusion, however when present in χ3987 with the lacI$^q$ repressor on pYA232, the fusion is expressed with a size, approximately 14 kDa, similar to that for the LT-B-ZP3 fusion of pYA3111.

As indicated in FIG. 17, the region of ZP-3 that contains the immunodominant B-cell epitope, as well as the overlapping epitope which induces autoimmune oophoritis in B6AF1 female mice, is contained within a DNA fragment that can be conveniently replaced by digesting any ZP-3 insert with NcoI and substituting an oligonucleotide specifying any desired amino acid sequence. For example, the sequence encoding the six amino acids Asn Ser Ser Ser Ser Gln (SEQ ID NO:55) can be deleted. This construct can then be used as described above.

Confirmation of phenotype and stability are done prior to inoculation of mice with the selected constructs.

Animal immunization is accomplished as described above.

Commercial Utility

The avirulent microbes provided herein are suitable for use in the preparation of anti-fertility compositions. These compositions are useful for diminishing or preventing fertility in a subject to which they are administered. The avirulent microorganisms which include genes encoding for gamete-specific antigens are also useful for the production of antibodies, both monoclonal and polyclonal, against antigens which are expressed in the avirulent microbe.

References Cited

Anderson, D. J., et al., *J Reprod Immunol* (1987) 10:231.

Benjamin, D. C., et al., *Ann Rev Immunol* (1985) 2:67.

Blanco, A., et al., *Biochem J* (1976) 153:165–172.

Bleil, J. D. and Wassarman, P. M., *Proc Natl Acad Sci U.S.A.* (1990) 87:5563.

Bronson, R. A., et al., *Fertil Steril* (1982a) 58:724–729.

Bronson, R. A., et al., *Am J Reprod Immunol* (1982b) 2:222–224.

Bronson, R., et al., *Fertil Steril* (1984) 42:171–183.

Challacombe, S. J., *Ann NY Acad Sci* (1983) 409:177–193.

Chen, C., and Jones, W. R., *Fertil Steril* (1981) 35:542–545.

Clements, J. D., and Finkelstein, R. A., *Infect Immun* (1979) 24:760–769.

Curtiss, R., III, and Kelly, S. M., *Infect Immun* (1987) 55:3035–3043.

Dor, J., et al., *Fertil Steril* (1981) 35:535–541.

Elson, C. O., *Curr Top Microbiol Immunol* (1988) 146:29–34.

Feuchter, F. A., et al., *Biol Reprod* (1981) 24:1099.

Erickson, R. P., et al., *Exptl Cell Res* (1975) 91:1–5.

Goldberg, E., *Ann NY Acad Sci* (1964) 121:560–570.

Goldberg, E., *J Biol Chem* (1972) 247:2004.

Goldberg, E., *Science* (1973) 181:458–459.

Goldberg, E., *Curr Top Biol Med Res* (1987) 14:103–122.

Goldberg, E., et al., *Fertil Steril* (1981) 35:214–217.

Gouy, M., and Gautier, C., *Nucleic Acids Res* (1982) 10:7055–7074.

Herr, J. C., et al., *Biol Reprod* (1990) 42:377.

Herr, J. C., et al., *Biol Reprod* (1986) 35:773.

Hogrefe, H. H., et al., *J Biol Chem* (1987) 262:13155–13162.

Hogrefe, H. H., et al., *J Biol Chem* (1989) 264:10513–10519.

Holmgren, J., et al., *Curr Top Microbiol Immunol* (1988) 146:197–204.

Ikemura, T., *Mol Biol Evol* (1985) 2:13–34.

Ingerslev, H. J., and Ingerslev, M., *Fertil Steril* (1989) 33:514–520.

James, A. A., et al., *J Mol Biol* (1982) 160:411–430.

Jones, G. W., et al., *Infect Immun* (1982) 338:476–486.

Keren, D. F., et al., *Infect Immun* (1988) 56:910–915.

Kille, J. W. and Goldberg, E., *J Reprod Immunol* (1980) 2:15.

Kremer, J., and Jager, S., *Int J Androl* (1980) 3:143–152.

Kummerfeld, H. L., and Foote, R. H., *Biol Reprod* (1976) 14:300–305.

Leyton, L. and Saling, P., *Cell* (1989) 57:1123.

Lee, C. Y., et al., *J Reprod Immunol* (1984) 6:227.

Lerum, J., and Goldberg, E., *Biol Reprod* (1974) 11:108–115.

LeVan, K. M., and Goldberg, E., *Biochem J* (1991) 273:587–592.

Liu, M. S., et al., *Mol Reprod Dev* (1990) 25:302.

Mahi-Brown, C. A., et al., *J Exptl Zool* (1982) 222:89.

Menge, A. C., et al., *Biol Reprod* (1979) 20:931–937.

Menge, A. C., et al., *Fertil Steril* (1982) 38:439–446.

Mettler, L., et al., *Am J Reprod Immunol* (1984) 6:227.

Millan, J. L., et al., *Proc Natl Acad Sci U.S.A.* (1987) 84:5311–5315.

Miller, S. E., et al., *Science* (1989) 248:935.

Montamat, E., et al., *Biochem J* (1988) 255:1053–1056.

Moore, H. D. M., et al., *J. Reprod Immunol* (1987) 11:157.

Munoz, M. G., and Metz., C. B., *Biol Reprod* (1978) 18:669–678.

Naz, R. K., et al., *Biol Reprod* (1983) 28:249.

Naz, R. K., et al., *Science* (1984) 225:342.

Naz, R. K., *J Clin Invest* (1987) 80:1375–1383.

Naz, R. K., *Am J Reprod Immunol* (1988) 16:21–27.

Primakoff, P., et al., *J Cell Biol* (1985) 101:2239–2244.

Primakoff, P., et al., *Biol Reprod* (1988a) 38:921–934.

Primakoff, P., et al., *Nature* (1988b) 335:543–546.

Samuel, T., et al., *Clin Exp Immunol* (1978) 33:252.

Shaha, C., et al., *Int J Androl* (1990) 13:17.

Shigeta, M., et al., *Clin Exp Immunol* (1980) 42:458.

Towbin, H., et al., *Proc Natl Acad Sci U.S.A.* (1979) 76:4350–4354.

Tung, K. S. K., et al., *J Reprod Immunol* (1979) 1:145–158.

Tung, K. S. K., et al., *FASEB J* (1991) 5:1088.

Wasserman, P. M., *Science* (1987) 235:553.

Wolf, D. P., et al., *Biol Reprod* (1983) 29:713.

Wood, D. M., et al., *Biol Reprod* (1981) 35:439.

Wright, R. M., et al., *Biol Reprod* (1990) 42:693.

Yan, Y. C., et al., *Fertil Steril* (1984) 42:614.

We claim:

1. An avirulent microbe derived from a pathogenic gram negative microorganism selected from the group consisting of Salmonella, Escherichia, and Salmonella-Escherichia hybrids comprising a recombinant expression system which encodes at least one gamete-specific antigen that is displayed on the surface of gametes exposed during the process leading to fertilization, wherein the avirulent microbe, upon administration to an individual, is capable of colonizing a lymphoreticular tissue and eliciting a mucosal immune response.

2. An avirulent microbe according to claim 1, wherein the avirulent microbe lacks a functioning native chromosomal gene encoding beta-aspartate semialdehyde dehydrogenase (Asd), and further wherein the microbe comprises a recombinant gene encoding a functional Asd polypeptide, the recombinant gene being linked to one or more genes encoding one or more gamete-specific antigens.

3. An avirulent microbe according to claim 1, wherein the avirulent microbe comprises a mutated cya gene such that the microbe is substantially incapable of producing functional adenylate cyclase.

4. An avirulent microbe according to claim 1, wherein the avirulent microbe comprises a mutated crp gene such that the microbe is substantially incapable of producing functional cyclic AMP receptor protein.

5. An avirulent microbe according to claim 2, wherein the avirulent microbe further comprises a mutated cya gene and a mutated crp gene such that the microbe is substantially incapable of producing functional adenylate cyclase and functional cyclic AMP receptor protein.

6. An avirulent microbe according to claim 1, wherein the microbe is *S. typhimurium*.

7. An avirulent microbe according to claim 1, wherein the microbe is an *E. coli*-Salmonella hybrid.

8. An avirulent microbe according to claim 1, wherein the gamete-specific antigen is lactic dehydrogenase-C.

9. An avirulent microbe according to claim 1, wherein the gamete-specific antigen is SP-10.

10. An avirulent microbe according to claim 1 wherein the gamete-specific antigen is ZP-3.

11. An avirulent microbe according to claim 5, wherein the gamete-specific antigen is lactic dehydrogenase-C.

12. An avirulent microbe according to claim 5, wherein the gamete-specific antigen is SP-10.

13. An avirulent microbe according to claim 5 wherein the gamete-specific antigen is ZP-3.

14. A vaccine composition comprising a therapeutically effective amount of an avirulent microbe according to claim 1, in combination with a pharmaceutically acceptable vehicle.

15. A vaccine composition comprising a therapeutically effective amount of an avirulent microbe according to claim 5, in combination with a pharmaceutically acceptable vehicle.

16. A method for inducing an antifertility state in a vertebrate subject, said method comprising administering to said subject an effective amount of a vaccine composition according to claim 14.

17. A method for inducing an antifertility state in a vertebrate subject, said method comprising administering to said subject, an effective amount of a vaccine composition according to claim 15.

18. A method according to claim 16, wherein the gamete-specific antigen is lactic dehydrogenase-C.

19. A method according to claim 16, wherein the gamete-specific antigen is SP-10.

20. A method according to claim 16, wherein the gamete-specific antigen is ZP-3.

21. A method according to claim 17, wherein the gamete-specific antigen is lactic dehydrogenase-C.

22. A method according to claim 17, wherein the gamete-specific antigen is SP-10.

23. A method according to claim 17, wherein the gamete-specific antigen is ZP-3.

24. An avirulent microbe according to claim 1 wherein the gamete-specific antigen is a sperm-specific antigen.

25. An avirulent microbe according to claim 24 wherein the sperm-specific antigen is selected from the group consisting of lactate dehydrogenase-C and SP-10.

26. An avirulent microbe according to claim 1 wherein the gamete-specific antigen is an ovum-specific antigen.

27. An avirulent microbe according to claim 5 wherein the gamete-specific antigen is a sperm-specific antigen.

28. An avirulent microbe according to claim 5 wherein the sperm-specific antigen is selected from the group consisting of lactate dehydrogenase-C and SP-10.

29. An avirulent microbe according to claim 5 wherein the gamete-specific antigen is an ovum-specific antigen.

30. A vaccine composition comprising a therapeutically effective amount of an avirulent microbe according to claim 24, in combination with a pharmaceutically acceptable vehicle.

31. A vaccine composition comprising a therapeutically effective amount of an avirulent microbe according to claim 25, in combination with a pharmaceutically acceptable vehicle.

32. A vaccine composition comprising a therapeutically effective amount of an avirulent microbe according to claim 26, in combination with a pharmaceutically acceptable vehicle.

33. A vaccine composition comprising a therapeutically effective amount of an avirulent microbe according to claim 27, in combination with a pharmaceutically acceptable vehicle.

34. A vaccine composition comprising a therapeutically effective amount of an avirulent microbe according to claim 28, in combination with a pharmaceutically acceptable vehicle.

35. A vaccine composition comprising a therapeutically effective amount of an avirulent microbe according to claim 29, in combination with a pharmaceutically acceptable vehicle.

36. A method according to claim 16, wherein the gamete-specific antigen is a sperm-specific antigen.

37. A method according to claim 36, wherein the sperm-specific antigen is selected from the group consisting of lactate dehydrogenase-C and SP-10.

38. A method according to claim 16 wherein the gamete-specific antigen is an ovum-specific antigen.

39. A method according to claim 17, wherein the gamete-specific antigen is a sperm-specific antigen.

40. A method according to claim 17, wherein the sperm-specific antigen is selected from the group consisting of lactate dehydrogenase-C and SP-10.

41. A method according to claim 17 wherein the gamete-specific antigen is an ovum-specific antigen.

42. The avirulent microbe according to claim 1 wherein said avirulent microbe is capable of eliciting a mucosal immune response to lactic dehydrogenase-C.

43. The avirulent microbe according to claim 1 wherein said avirulent microbe is capable of eliciting a mucosal immune response to SP-10.

44. The avirulent microbe according to claim 1 wherein said avirulent microbe is capable of eliciting a mucosal immune response to ZP-3.

45. A vaccine composition comprising a therapeutically effective amount of an avirulent microbe according to claim 42.

46. A vaccine composition comprising a therapeutically effective amount of an avirulent microbe according to claim 43.

47. A vaccine composition comprising a therapeutically effective amount of an avirulent microbe according to claim 44.

48. A method for inducing an antifertility state in a vertebrate subject, said method comprising administering to said subject an effective amount of a vaccine composition according to claim 45.

49. A method for inducing an antifertility state in a vertebrate subject, said method comprising administering to said subject an effective amount of a vaccine composition according to claim 46.

50. A method for inducing an antifertility state in a vertebrate subject, said method comprising administering to said subject an effective amount of a vaccine composition according to claim 42.

* * * * *